US005770396A

United States Patent [19]
Kinet

[11] Patent Number: 5,770,396
[45] Date of Patent: Jun. 23, 1998

[54] ISOLATION CHARACTERIZATION, AND USE OF THE HUMAN BETA SUBUNIT OF THE HIGH AFFINITY RECEPTOR FOR IMMUNOGLOBULIN E

[75] Inventor: Jean Pierre Kinet, Bethesda, Md.

[73] Assignee: The United States of America as represented by the Department of Health and Human Services, Washington, D.C.

[21] Appl. No.: 869,933

[22] Filed: Apr. 16, 1992

[51] Int. Cl.$^6$ .............................. C12N 5/10; C12N 15/12
[52] U.S. Cl. .................. 435/69.1; 435/252.3; 435/320.1; 536/23.5; 536/24.3
[58] Field of Search ................. 435/69.1, 252.3, 435/320.1; 536/23.5, 24.3

[56] References Cited

U.S. PATENT DOCUMENTS

| | | | |
|---|---|---|---|
| 4,171,299 | 10/1979 | Hamburger | 260/112.5 |
| 4,477,446 | 10/1984 | Jones et al. | 424/244 |
| 4,940,782 | 7/1990 | Rup et al. | 530/387 |
| 4,946,788 | 8/1990 | Delespesse | 435/240.27 |
| 4,962,035 | 10/1990 | Leder et al. | 435/320 |
| 5,091,313 | 2/1992 | Chang | 435/240.27 |

FOREIGN PATENT DOCUMENTS

| | | |
|---|---|---|
| 0 286 700 A1 | 10/1988 | European Pat. Off. . |
| 0 321 601 A1 | 6/1989 | European Pat. Off. . |
| 90/04640 | 5/1990 | WIPO . |

OTHER PUBLICATIONS

P.N.A.S, 84:3792–3796, Jun. 1987, Fong et al. Distinct Forms of the β Subunit of GTP–Binding Regulatory Proteins Identified by Molecular Cloning.

Kurosaki, et al. The β Subunit of the FcεRI is Associated with the FcγRIII on Mast Cells, *J. Exp. Med.* 75:447–451 (1992).

Le Coniat, et al., The Human Genes for the α and γ Subunits of the Mast Cell Receptor for Immunoglobulin E are Located on Human Chromosome Band 1q23, *Immunogenetics*, 32:183–186 (1990).

Howard, et al., CD3 ζ Subunit can Substitute for the γ Subunit of Fc$_ε$ Receptor Type I in Assembly and Functional Expression of the High–Affinity IgE Receptor: Evidence for Interreceptor Complementation, *Proc. Natl. Acad. Sci. USA*, 87:7015–7019 (1990).

Varin–Blank, et al., Surface Expression of Mutated Subunits of the High Affinity Mast Cell Receptor for IgE*, *J. Biol. Chem.*, 265:15685–15694 (1990).

Burton, et al. T *Cell Receptor Variable Gene Expression: Analysisin Ragweed–Sensitive Patients During Allergen Exposure, Int. Arch. Allergy Appl. Immunol*, 306–310 (1990).

Küster, et al. Characterization and Expression of the Gene for the Human Fc Receptor γ Subunit, *The Journal of Biological Chemistry*, 265:6448–6452 (1990).

Metzger, et al., The Receptor with High Affinity for IgE, *Ciba Foundation Symposium*, 147:93–113 (1989).

Ra, et al., Complete Structure of the Mouse Mast Cell Receptor for IgE (FcεRI) and Surface Expression of Chimeric Receptors (Rat–Mouse–Human) on Transfected Cells, *J. Biol. Chem.*, 264:15323–15327 (1989).

Miller, et al., Expression of High–Affinity Binding of Human Immunoglobulin E by Transfected Cells, *Science*, 244:334–337 (1989).

Blank, et al., Complete Structure and Expression in Tranfected Cells of High Affinity IgE Receptor, *Nature*, 337:187–189 (1989).

Nilsson, et al., Enhancement of IgE Synthesis in the Human Myeloma Cell Line U–266 with an IgE Binding Factor from a Human T–Cell Line, *Scand. J. Immunol.*, 34:721–726 (1991).

Kinet, et al., Isolation and Characterization of cDNAs Coding for the β Subunit of the High Affinity Receptor for Immunoglobulin E, *Proc. Natl. Acad. Sci. USA*, 85:6483–6487 (1988).

Hakimi, et al., The α Subunit of the Human IgE Receptor (FcERI) is Sufficient for High Affinity IgE Binding, *J. Biol. Chem.*, 265:22079–22081 (1990).

Ra, et al., A Macrophage Fcγ Receptor and the Mast Cell Receptor for IgE Share an Identical Subunit *Nature*, 341:752–754 (1989).

Metzger, et al., Emerging Picture of the Receptor with High Affinity for IgE, *Int. Arch. Allergy Appl. Immunol*, 14–17 (1989).

Bieber, et al., Human Epidermal Langerhans Cells Express the High Affinity Receptor for Immunoglobulin E (FcεRI), *J. Exp. Med.*, 175:1285–1290 (1992).

Sasada, et al., Secretion of Human EGF and IgE in Mammallian Cells by Recombinant DNA Techniques; Use of a IL–2 Leader Sequence, *Cell Structure and Function*, 13:129–141 (1988).

DDBJ Database Entry Hsigerb, Accession No. D10583; Feb. 25, 1992, K. Maekawa et al.; "Determination of the Sequence Coding for the Beta Subunit of the Human HIgh–Affinity IgE Receptor".

Kinet, J.–P., et al., "Isolation and Characterization of cDNAs Coding for the Beta Subunit of the High–Affinity Receptor for Immunoglobulin E", *Proceedings of the National Academy of Sciences USA*, vol. 85, pp. 6483–6487, Sept. 1988.

(List continued on next page.)

*Primary Examiner*—John Ulm
*Attorney, Agent, or Firm*—Klarquist Sparkman Campbell Leigh & Whinston, LLP

[57] ABSTRACT

The present invention relates to nucleic acid sequences, encoding amino acid sequences of the α, β, and γ subunits of the high affinity receptor for immunoglobulin E, and for amino acid sequences of the subunits. The invention further relates to a method of producing the receptor by expressing cDNA for its α, β, and γ subunits in a host cell simultaneously. Aspects of the invention are methods and compositions to inhibit the function of the human beta subunit, thereby treating or preventing allergic reactions.

20 Claims, 52 Drawing Sheets

OTHER PUBLICATIONS

Küster, H., et al., "Characterization and Expression of the Gene for the Human Fc Receptor γ Subunit", *The Journal of Biological Chemistry*, vol. 265, pp. 6448–6452, Apr. 1990.

Alber, Gottfried, "Structure–Function Relationships in the Mast Cell High Affinity Receptor for IgE", The Journal of Biological Chemistry, vol. 266, pp. 22613–22620, Nov., 1991.

Küster, H., "The Gene and cDNA for the Human High Affinity Immunoglobulin E Receptor Beta Chain and Expression of the Complete Human Receptor", *The Journal of Biological Chemistry*, vol. 267, Jun. 1992.

Maekawa, K., et al., "Determination of the Sequence Coding for the Beta Subunit of the Human High–Affinity IgE Receptor", FEBS LETTERS, vol. 302, pp. 161–165, May 1992.

FIG. 1A

```
TACTAAGAGT CTCCAGCATC CTCCACCTGT CTACCACCGA GCATGGGCCT ATATTTGAAG        60

CCTTAGATCT CTCCAGCACA GTAAGCACCA GGAGTCCATG AAGAAG ATG GCT CCT         115
                                             Met Ala Pro
                                               1

GCC ATG GAA TCC CCT ACT CTA CTG TGT GTA GCC TTA CTG TTC GCT              163
Ala Met Glu Ser Pro Thr Leu Leu Cys Val Ala Leu Leu Phe Ala
 5                      10                      15

CCA GAT GGC GTG TTA GCA GTC CCT CAG AAA CCT AAG GTC TCC TTG AAC          211
Pro Asp Gly Val Leu Ala Val Pro Gln Lys Pro Lys Val Ser Leu Asn
 20                      25                      30                   35

CCT CCA TGG AAT AGA ATA TTT AAA GGA GAG AAT GTG ACT CTT ACA TGT          259
Pro Pro Trp Asn Arg Ile Phe Lys Gly Glu Asn Val Thr Leu Thr Cys
         40                      45                      50

AAT GGG AAC AAT TTC TTT GAA GTC AGT TCC ACC AAA TGG TTC CAC AAT          307
Asn Gly Asn Asn Phe Phe Glu Val Ser Ser Thr Lys Trp Phe His Asn
         55                      60                      65

GGC AGC CTT TCA GAA GAG ACA AAT TCA AGT TTG AAT ATT GTG AAT GCC          355
Gly Ser Leu Ser Glu Glu Thr Asn Ser Ser Leu Asn Ile Val Asn Ala
 70                      75                      80
```

FIG. 1B

```
AAA TTT GAA GAC AGT GGA GAA TAC AAA TGT CAG CAC CAA CAA GTT AAT     403
Lys Phe Glu Asp Ser Gly Glu Tyr Lys Cys Gln His Gln Gln Val Asn
     85                  90                  95

GAG AGT GAA CCT GTG TAC CTG GAA GTC TTC AGT GAC TGG CTG CTC CTT     451
Glu Ser Glu Pro Val Tyr Leu Glu Val Phe Ser Asp Trp Leu Leu Leu
100                 105                 110                 115

CAG GCC TCT GCT GAG GTG GTG ATG GAG GGC CAG CCC CTC TTC CTC AGG     499
Gln Ala Ser Ala Glu Val Val Met Glu Gly Gln Pro Leu Phe Leu Arg
                120                 125                 130

TGC CAT GGT TGG AGG AAC TGG GAT GTG TAC AAG GTG ATC TAT TAT AAG     547
Cys His Gly Trp Arg Asn Trp Asp Val Tyr Lys Val Ile Tyr Tyr Lys
            135                 140                 145

GAT GGT GAA GCT CTC AAG TAC TGG TAT GAG AAC CAC AAC ATC TCC ATT     595
Asp Gly Glu Ala Leu Lys Tyr Trp Tyr Glu Asn His Asn Ile Ser Ile
        150                 155                 160

ACA AAT GCC ACA GTT GAA GAC AGT GGA ACC TAC TAC TGT ACG GGC AAA     643
Thr Asn Ala Thr Val Glu Asp Ser Gly Thr Tyr Tyr Cys Thr Gly Lys
    165                 170                 175

GTG TGG CAG CTG GAC TAT GAG TCT GAG CCC CTC AAC ATT ACT GTA ATA     691
Val Trp Gln Leu Asp Tyr Glu Ser Glu Pro Leu Asn Ile Thr Val Ile
180                 185                 190                 195
```

FIG. 1C

```
AAA GCT CCG CGT GAG AAG TAC TGG CTA CAA TTT TTT ATC CCA TTG TTG    739
Lys Ala Pro Arg Glu Lys Tyr Trp Leu Gln Phe Phe Ile Pro Leu Leu
                200                 205                 210

GTG GTG ATT CTG TTT GCT GTG GAC ACA GGA TTA TTT ATC TCA ACT CAG    787
Val Val Ile Leu Phe Ala Val Asp Thr Gly Leu Phe Ile Ser Thr Gln
            215                 220                 225

CAG CAG GTC ACA TTT CTC TTG AAG ATT AAG AGA ACC AGG AAA GGC TTC    835
Gln Gln Val Thr Phe Leu Leu Lys Ile Lys Arg Thr Arg Lys Gly Phe
        230                 235                 240

AGA CTT CTG AAC CCA CAT CCT AAG CCA AAC CCC AAA AAC AAC TGATATAATT 887
Arg Leu Leu Asn Pro His Pro Lys Pro Asn Pro Lys Asn Asn
    245                 250                 255

ACTCAAGAAA TATTTGCAAC ATTAGTTTTT TTCCAGCATC AGCAATTGCT ACTCAATTGT    947

CAAACACAGC TTGCAATATA CATAGAAACG TCTGTGCTCA AGGATTATA GAAATGCTTC   1007

ATTAAACTGA GTGAAACTGG TTAAGTGGCA TGTAATAGTA AGTGCTCAAT TAACATTGGT   1067

TGAATAAATG AGAGAATGAA TAGATTCATT TATTAGCATT GTAAAAGAGA TGTTCAATTT   1127

CAATAAAATA AATATAAAAC CATGTAAAAA AAAAAAAAAA AAAAAAA               1174
```

```
ACGTTCTGT GTAACAATAT CTTTTATTCC TGGATAGTCC AATTA ATG AAA AAA        54
                                              Met Lys Lys
                                               -3

ATG GAC ACA GAA AAT AAG AGC AGA GCA GAT CTT GCT CTC CCA AAC CCA    102
Met Asp Thr Glu Asn Lys Ser Arg Ala Asp Leu Ala Leu Pro Asn Pro
 1               5                    10                  15

CAA GAA TCC CCC AGC GCA CCT GAC ATT GAA CTC TTG GAA GCG TCC CCT    150
Gln Glu Ser Pro Ser Ala Pro Asp Ile Glu Leu Leu Glu Ala Ser Pro
              20                  25                  30

CCT GCA AAA GCT CTA CCA GAG AAG CCA CCC GCC TCA CCC CCA CAG CAG    198
Pro Ala Lys Ala Leu Pro Glu Lys Pro Ala Ser Pro Pro Pro Gln Gln
          35                  40                  45
```

FIG. 6A(2)

```
ACA TGG CAG TCA TTT TTG AAG AAA GAG TTG CTG GGC GTA ACC    246
Thr Trp Gln Ser Phe Leu Lys Lys Glu Leu Phe Leu Gly Val Thr
     50                   55                  60

CAA GTT CTG GTT GGT TTG ATA TGC CTT TGT TTT GGA ACA GTT GTC TGC    294
Gln Val Leu Val Gly Leu Ile Cys Leu Cys Phe Gly Thr Val Val Cys
 65                  70                  75                  80

TCC ACA CTC CAG ACT TCA GAC TTT GAC GAC GAA GTG CTT TTA TTA TAT    342
Ser Thr Leu Gln Thr Ser Asp Phe Asp Asp Glu Val Leu Leu Leu Tyr
         85                  90                  95

AGA GCA GGC TAC CCA TTC TGG GGT GCA GTG CTG TTT GTT TTG TCT GGA    390
Arg Ala Gly Tyr Pro Phe Trp Gly Ala Val Leu Phe Val Leu Ser Gly
             100                 105                 110

TTT TTG TCA ATT ATG TCC GAA AGG AAA ACA CTG TAT CTG GTG AGA    438
Phe Leu Ser Ile Met Ser Glu Arg Lys Asn Thr Leu Tyr Leu Val Arg
             115                 120                 125

GGC AGC CTG GGA GCA AAC ATT GTC AGC AGC ATC GCT GCA GGC TTG GGG    486
Gly Ser Leu Gly Ala Asn Ile Val Ser Ser Ile Ala Ala Gly Leu Gly
             130                 135                 140

ATC GCC ATA TTG ATT CTC AAT CTG AGC AAC AAC TCC GCT TAT ATG AAC    534
Ile Ala Ile Leu Ile Leu Asn Leu Ser Asn Asn Ser Ala Tyr Met Asn
             145                 150                 155                 160
```

FIG. 6A(3)

```
TAC TGC AAG GAT ATA ACC GAA GAC GAT GGT TGC TTC GTG ACT TCT TTC    582
Tyr Cys Lys Asp Ile Thr Glu Asp Asp Gly Cys Phe Val Thr Ser Phe
                165                 170                 175

ATC ACA GAA CTG GTC GTG TTG ATG TTG CTG TTT CTC ACC ATC CTG GCC TTT    630
Ile Thr Glu Leu Val Val Leu Met Leu Leu Phe Leu Thr Ile Leu Ala Phe
            180                 185                 190

TGC AGT GCC GTG CTG CTC ATT ATC ATC TAT AGG ATT GGA CAA GAA TTT GAG    678
Cys Ser Ala Val Leu Leu Ile Ile Ile Tyr Arg Ile Gly Gln Glu Phe Glu
        195                 200                 205

CGT AGT AAG GTC CCC GAT GAC CGT CTC TAT GAA GAA TTA CAT GTG TAT    726
Arg Ser Lys Val Pro Asp Asp Arg⟨Leu Tyr Glu Glu Leu His Val Tyr
    210                 215                 220

TCA CCA ATT TAC AGT GCG TTG GAA GAC ACA AGG GAA GCG TCC GCA CCA    774
Ser Pro Ile Tyr Ser Ala Leu Glu Asp Thr Arg⟩⟨Glu Ala Ser Ala Pro
225                 230                 235                 240

GTT GTT TCA TAAGAATCAA GGGGCCAGGA CAATCTGATT CCAGTCTAGT    823
Val Val Ser⟩
```

FIG. 6A(4)

```
CTTGAGAGTC GATCTTTTTG CAACATTATG GCAACATTTC TGTTTCCTCC GCACTCTATC    883
AACTTTTCAA TTGGATTGTT CTGTAGATAC CCCTGTTTCA GTTATGATGC CTCTGGTCTT    943
TAATTATCTC CCTTTTTGTG GATATCGTTC AATCCAGTTT TCTTGTTTTG TGTCACAGTC   1003
TCACATACAA CCTTTCTGGA AAGTCATCAA AAACAAGCTA GCTTTTATTG CATGTCTACT   1063
TTCATGAACA AAAGGAAGGA GGAGTTATTT TGAGAGTTTA ACTAAACTTA GATAATCAGG   1123
TAATATTTGA CTCTTAGTTC ATTTTAGAAT TCTCAACAAT ACTTGTGCAT GATATATGCC   1183
CACCATATCA AGCCTTCTAT ATATATTTAA TATGGTATTT ACTTTTCTAT GTAGATAGAT   1243
TTTCCACCCT CAATAATAAT GGGTTTTTCA GAGACATAAA GCTTTATGAA AAGACACATA   1303
```

FIG. 6A(5)

```
TTATCTAATT CATGGGTATA TTCACTAATA CAGTTGTTGC TCAGTGGTGT TTACTACTTG    1363
GTGGGTAGTA GGTAATAGAG AACATTATTA AATCATTCAG TGTAGTGAGA TGCATAGGTA    1423
AAATCAGGGA CACTGTGAGT GTGTATATCT TTTGGTAAGA CATGTGTGAA AATGAAGAAT    1483
AAACTGATGA AGACTTGAGC TGGAAAGTAG TCAATGGGAA TGACAAGAAA TGATTGTGTA    1543
TAACACTTGT AGATAAAATAA CTACCAACAA TTGGTAGAGA TTGCCATGTA TGCCTAAAAT    1603
CTCCCAGCCC AAGGCCAGCC TCTGTTACAC AGTGAGTTAG AGGCCAGTCT GGGCTACACA    1663
AGATCATACA TCAAAGGACG AAAGAAGATG TTGGTTCAAA CTGTTAACAC AGTAAGGGAT    1723
ATTTAAACAA ACAGAAGTTT GACTGATATA TTGAGTGCTT GAGTTTTTAA TAAAACTGAA    1783
TGAATAACAT TGCGGGGGAG GGGAGCAGTG ATGCAGAAGT CTGGATGATG GAGGAGTAGC    1843
AGAATCAGAT GAAACATTGA AACGTATTTC CAGACTTTTG TTCTGAGATG GTTATAAGAG    1903
```

FIG. 6A(6)

```
CAATCACCAT TAAATGAAGA AGGTCAAGAC ACCAAAAGAA TTATTTTGAG ATAGAATTAA    1963
GACAGTCAAA ATCCACATGC CTATACTTAG AAGGTGAAGT AAGGATCAAA AGTAGAAAGC    2023
CTAACGATTA GTTGGAAAAG CATATTACGT TAGGCAGCAG ATGTCTATAG TGGAGAAAAG    2083
TTAAACAAGG AGAAATAAAT AACCACCAGA GACTCTACAT GTTGGTTTGG GAAATAAGAG    2143
AAAATAGCAA TTCTAAACGA ATGCAAACTC TGAAGAAGCA TTTCCCAAAG GGTGTGGGCA    2203
GAGGACCAGA ACATTTGCAA ATGTACCTAG AGAGCAAACC TGAATAGGAG GTAAAATGGG    2263
GGAAAAGCAG CTAAGAAAAT GATTTTGTTG CTGTTATTTA GATTTTAAAA GAAACAAAAA    2323
GAGTCATTAA AAATCTGTTT GCTGGGATCA GTTATTGTGT TCTCTGTGTA TGTCCAAAGT    2383
ACAGGTAACT TTTCTAAATC TTCCCTGTAAG GCTCACCCTCA TATGTCTCTT CACATAGCCA    2443
CACCCTTGAT TCACAGTTAC TCTACCACAG TAGTAAACTG TGCTTGTGGT CTCCCTTATG    2503
TATCTTCACT AGTGTTTATA AAATAAATCA GAATTATTTA AA                        2545
```

FIG. 6B

```
GTG AGA ACA TAT CTG TAATTGTTTC TGAAATGATG CTAACCAGAG ATTTTATTTT      55
Val Arg Thr Tyr Leu
 1               5

AATCAAAGAC AACTAATTTT CTTTTAATCA AGTGCTTATC TCTAGCCTTT CAATAATATC   115
TACAGTTCTT CATTTATATG CACATAGCCA TCTATAAATG TAGTTTCCAA AGCACTCTCT   175
ACATATACTC ATTAACAAGA GCAAATACAC TCACCACAGT TAACTATGGT TTAACCCATT   235
ACTATACTTT TATTGACTGA AAACCTTGAG ACTGTACAAA AAAAAAAAAA A            286
```

FIG. 9

```
AGCGCTGCAGCCCCCGCCCAGG ATG ATC CCA GCG GTG ATC TTG TTC           46
                       M   I   P   A   V   I   L   F           -11

TTG CTC CTT TTG GTG GAA GAA GCA GCT GCC CTA GGA GAG CCG CAG      91
 L   L   L   L   V   E   E   A   A   A   L   G   E   P   Q       5
                                     -1 ↑ +1
CTC TGC TAT ATC CTG GAT GCC ATC CTG TTT TTG TAT GGT ATT GTC     136
 L   C   Y   I   L   D   A   I   L   F   L   Y   G   I   V      20

CTT ACC CTG CTC TAC TGT CGA CTC AAG ATC CAG GTC TAC AAG GCA     181
 L   T   L   L   Y   C   R   L   K   (I   Q   V   Y   R)  (K    A   35

GAC ATA GCC AGC CGT GAG AAA TCA GAT GCT GTC TAC ACG GGC CTG     226
 D   I   A   S   R}  {E   K   S   D   A   V   Y)  T   G   L     50

AAC ACC CGG AAC CAG GAG ACA TAT GAG ACT CTG AAA CAT GAG AAA     271
 N   T   R   (N   Q   E   T   Y   E   T   L   K)  H ↑ E   K     65

CCA CCC CAA TAG CTTTACAACACGTGTTCTCAGCTGCATTCCTTTTCCGCTTTTA     326
 P   P   Q    -                                                  68

ATTCTCTCCTCCGCCCTCATGATTGACGTGGCTACCCTCCGTGCTTCTGGAACTAG       385
CTGACCTTATTCCCAGAACCATGCTAGGCTCTAAATCAATGTCCCATATCCACCAAAG     444
ACTTACTCACTGACATTTCTTCTCCCATCCTCCTTTGCTTCATTCCTCTTTCCTTCC     503
CTGATCCCTCTGTGCTCACTAAACAATGGGAAGGATTACCCCCAATAAAGCTGCCAGA    562
GATCACGCTCAAAAAAAAAAAAA                                       586
```

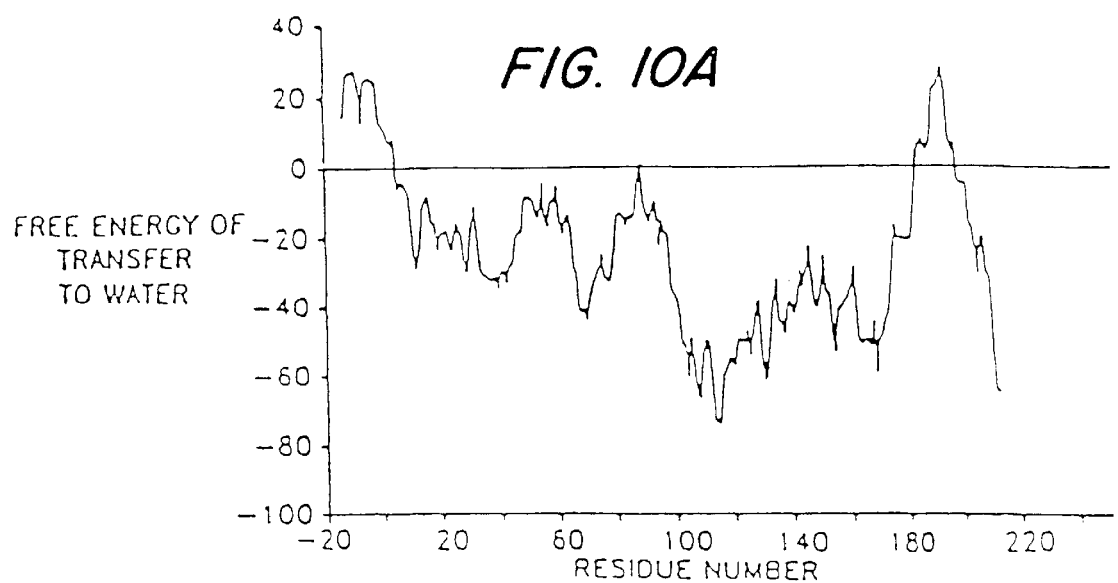
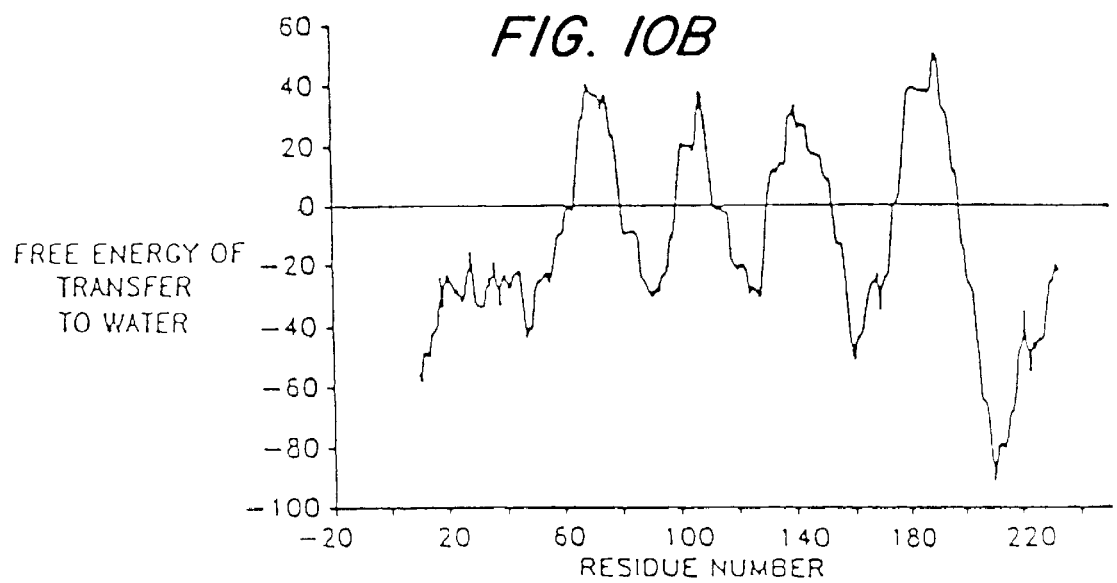
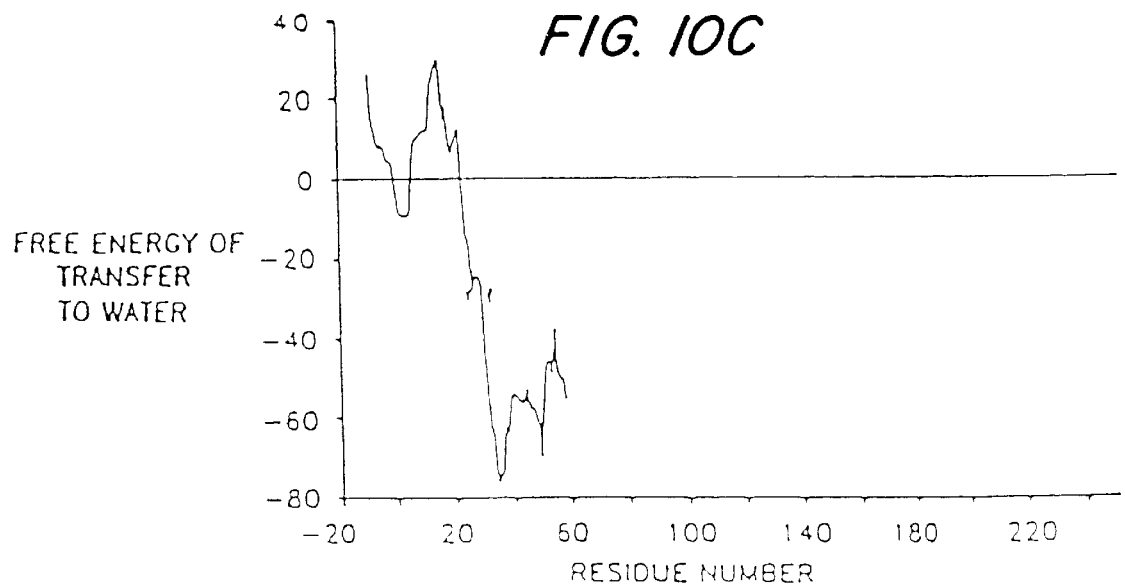

FIG.IIA
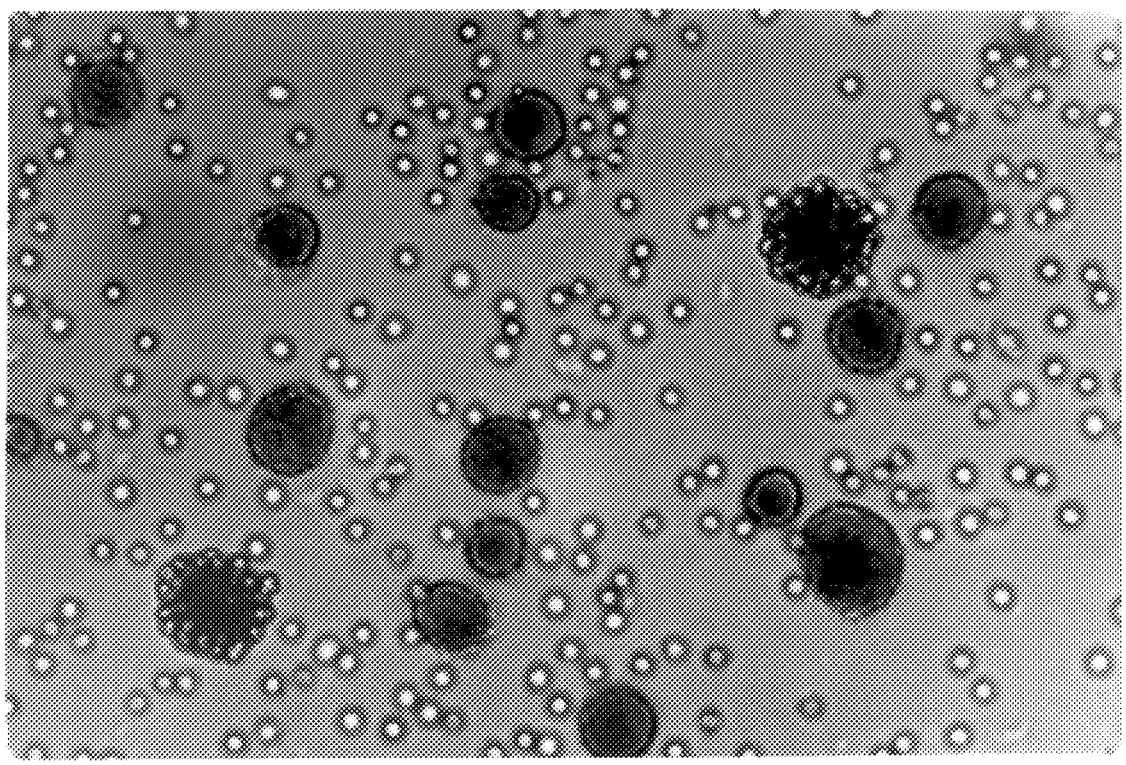

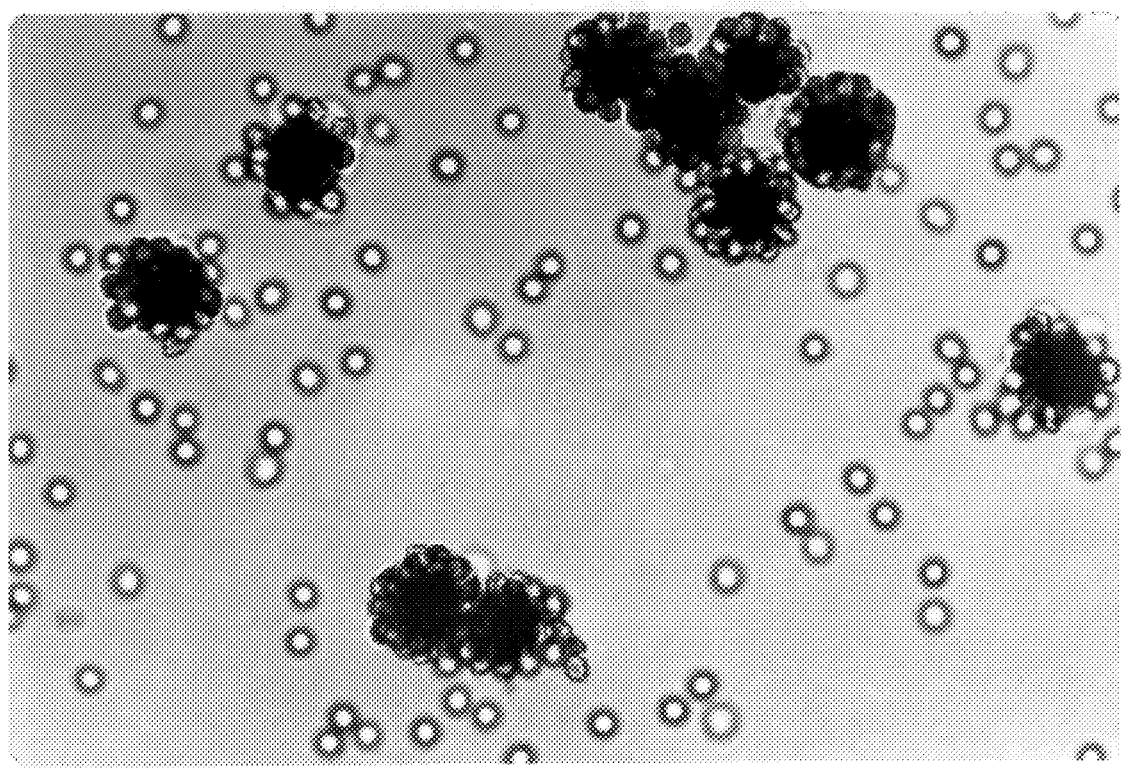
FIG.IIB

| | | | | | |
|---|---|---|---|---|---|
| AAGCTTTTCA | AAGGTGCAAT | TGGATAACTT | CTGCCATGAG | AAATGGCTGA | ATTGGACAC | 60 |
| AAGTGGGGAC | AATTCCAGAA | GAAGGGCACA | TCTCTTTCTT | TTCTGCAGTT | CTTTCTCACC | 120 |
| TTCTCAACTC | CTACTAAAAT | GTCTCATTTT | CAGGTTCTGT | AAATCCTGCT | AGTCTCAGGC | 180 |
| AAAATTATGC | TCCAGGAGTC | TCAAATTTTC | TTATTTCATA | TTAGTCTTTA | TTTAGTAGAC | 240 |
| TTCTCAATTT | TTCTATTCAT | CACAAGTAAA | AGCCTGTTGA | TCTTAATCAG | CCAAGAAACT | 300 |
| TATCTGTCTG | GCAAATGACT | TATGTATAAA | GAGAATCATC | AATGTCATGA | GGTAACCCAT | 360 |
| TTCAACTGCC | TATTCAGAGC | ATGCAGTAAG | AGGAAATCCA | CCAAGTCTCA | ATATAATAAT | 420 |
| ATTCTTTATT | CCTGGACAGC | TCGGTTAATG | AAAAAATGGA | CACAGAAAGT | AATAGGAGAG | 480 |
| CAAATCTTGC | TCTCCCACAG | GAGCCTTCCA | GGTAGGTACA | AGTTATTATT | TTTTTCTACC | 540 |

FIG. 14B

```
CTCAGTCACT TGTGGCAGGG GAAGTCATAG TCACGGTGCT TAGGAGATGA AACTTTATTG    600
ATTTAGGCAT GGATCCATCT AGTTTAATTA ATATATTGGG TATGAGGAAG CTACTTGCTG    660
TACTTTCCAT GTGGTTCTCT CTCCCTGGAG AGGAACATTT TTACTCAGCT TGCAAACTGG    720
AAATAGATTT TCTCACATTA GAAGCTCATT TTCTGGGTAT GAGACAGGAG AGTTCATACT    780
GTGTATGTAG ATCTCTGGCT TCTGGGTCTG ACATGTGCTG AGGGACACAT ATCCTTCACA    840
CATGCTTTTA TAAATACTTG ATAAAGTAAC CTGCTTCTTG ATTGGTCTTT ATAATCCATA    900
AGCTGTGGGA TGCTTCTCTG AAGATGAAAA TAGTAATAGA GTCCCATCTA GCTATTCAAA    960
GCCATTCCTT CATTGTATTC TGTGCACATG AAGTTGGGGT TTGTTACTGA CAAAATATAT   1020
TCAGATACAT TTCTATGTTA AAAGGATTGT GAGATGCATA GGTAAATGTG TTTATTTTCA   1080
GTTTTACTTG TCAACATAGA TGAATGAGAA AGAACACTTG AGTAACACTG GATTAAGAAT   1140
```

FIG. 14C

```
AGGAAAATTT GGCATGGATT TTGCTCCATT TGTCCCATC TAATCACTTG GATAGTGTTC    1200
AGGTGTTCTT GGTCAGTTAC TTGGATGCTC TGAGCTTTAG TTTCTTGGTG ATTACAATGA   1260
AGATTTGAAT TACAGGATGG CTTTGAAAAA ATAAACAAAA CTCCCCTTTC TGTCTGTCGA   1320
GAATGTTGCA CAGGGAGTTA CAGAATGTTC TCATGACTGA ATTGCTTTTA AATTTCACAG   1380
TGTGCCTGCA TTTGAAGTCT TGGAAATATC TCCCCAGGAA GTATCTTCAG GCAGACTATT   1440
GAAGTCGGCC TCATCCCCAC CACTGCATAC ATGGCTGACA GTTTTGAAAA AAGAGCAGGA   1500
GTTCCTGGGG GTGAGTGAGC CTCCTCCAAC TTTGACTAGA GTAAGGGTTG GGTCTAGAAA   1560
AGAATATTGA GTTGCATCAA CTGTTTTCCC ACTTGGATTC ATGAGAGGTG TTAGGTCCTT   1620
TAAAAAACAT GGTAGATAAA GAGTTGACAC TAACTGGGTC CTTTTGGGAA GAGCCAGAAG   1680
CATTCCTCA TAAAGACTTT TCTTTACTTA GACGAGAATG GCCAACAGGA GTGAAGGATT    1740
CATAACTTTA TCTTTACTTA GATGTAAAGA ACAATTACTG ATGTTCAACA TGACTACATA   1800
CATAAAGGCG CATGGAGAAA AGTATTGGCC TTCCATGCAT TAGGTAGTGC TTGTATCAAT   1860
TCTTATAGTG GCTAGGGTAT CCTGGAAAAT CTTACGTGTG GATCATTTCT CAGGACAGTC   1920
TAGGACACTA ACGCAGTTTC TCATGTTTGG CTTCTATTAT TAAAAAATGA TACAATCTCG   1980
```

FIG. 14D

```
GGAAAATTTT TTTGATTTTC ATGAAATTCA TGTGTTTTTC TATAGGTAAC ACAAATTCTG   2040
ACTGCTATGA TATGCCTTTG TTTTGGAACA GTTGTCTGCT CTGTACTTGA TATTCACAC    2100
ATTGAGGGAG ACATTTTTTC ATCATTTAAA GCAGGTTATC CATTCTGGGG AGCCATATTT   2160
GTGAGTATAT ATCTATAATT GTTTCTGAAA TAACACTGAA CATAGGTTTT TCTCTTTCTC   2220
AGATCTAACC AGTTGTTTAT TCCCAGTATT AAGATGATAT TTATAATTCT TAATTATAAA   2280
TATATGTGAG CATATATAAC ATAGATATGC TCATTAACAA CAACAAAAGA TTCTTTTTAC   2340
AATTAACGGT GGGTTAAACA TTTAGCCCAC AGTTTTATCC CATGAGAAAC CTGAATCTAA   2400
TACAAGTTAA ATGACTTGCC TAAGGGCCAC TTGACTAATA GTAATTGAAC CTAAACTTTC   2460
AGAATCCAAC TCCAGGAACA TACTTCTAGC ACTATTCATC AATAAAGTTA TATGATAAAT   2520
ACATACAACT TTATCTGTCA ACTAAAAATA ACAACAGAGG CTGGGCATGG TGGCTCACAC   2580
CCGTAATCCC AGCACTTTGG GAGGCTGAGG CAGGTGGATC ACCTGAGGTC AGGAGTTGA    2640
```

FIG. 14E

```
GACCAGCCTG  ACCAACATGG  TGAAACCTCA  TCTCTACTAA  ATATAAAAAA  TTAGCTGAGT  2700
GTGATAGTGC  ATACCTGTAA  TCCAGCTACT  TAAGAGGCTG  AGGCAGGAGG  CTGTTTGAA   2760
CCTGGAAGGC  AGAGGTTGCA  GTGAGCTGAG  ATTGTGCCAT  TGCACTCCAG  CCTGGGCAAT  2820
AAGTGCGAAC  TCTGTCTCAA  AATAATAATA  ATATAATAAT  AAAATAAAGT  TGTCTTCATG  2880
AAAAATGAGG  AAAGAGATTG  CTGGGGTGAG  AAACATTAAG  ATCAATGGGC  ATATGGTGAC  2940
CTTCTATGCC  CTAGAAACTC  TTTTANGGTA  TTTTCTCCCTG  GTATCTCTTT  TACNCATCGT  3000
TCTATCTGGA  AAAATAGGTG  GATGAGTGAG  ATAATAACGG  TATATACTTT  TTAAAGGTCT  3060
AATTGACATA  TATAAATTGC  AAGTATTTCA  GATGTCAATT  TGCTAACCTT  GACACACATA  3120
GACACACATG  AAAACATCAC  CACATTAATA  CAATGTATGT  ATCCATCATT  CCAAAAGCTT  3180
CCCTGTGTAT  CTTTGTAACT  CTTTCTTCCT  CCCTCCACTC  CTTGTCCCTCT  CGTTCCCAAG  3240
AAAACATTGA  TCTGCTTCCT  GTGAATATAA  ATTAACTTAC  ATTTTTTAGA  GCTTATATA   3300
AGTATGTTCT  CTTTACTGTT  TGTCTTCCTT  CGCTGCACAG  TTATTTTGAG  ATTCTTCAAG  3360
```

FIG. 14F

```
AGTATGTTCT CTTTACTGTT TGTCTTCCTT CGCTGCACAG TTATTTGAG ATTCTTCAAG    3360
TTTTTCTT ATATCGATAC TTCATTCACA AGAATATATT TTAATTCTAG ACTATGTCAC    3420
ATTGACTTTG TCGTCTGCTA AATCCCTTAGT GCTCAGATGA CTTGTTCAGG ACTCTCCCTTG  3480
AACCTGTACC TCTGTTANAT TGAAACTTGT CTCTACTGTC TTTTTATTTC AAACACAGCT   3540
TATTAGGTGT CTCTCAACCC ATCAAACNCA CAATCTGAGT CTTTAGGAGA TTGCTTTGAA   3600
TTTGTGCTAT TGACTTATAT NTATATNAAA TNTGTAAATG TTTGGTAAAA ATATCATCAT   3660
GTACNTTTTC ATAATTACGC TATNTNCACA TGATATATGT CAGACTCTGG AAATATGCAT   3720
GCCACAGACA CGTGTTTCTT GCCTAAAGGG GCTGATGGAA GACNCACATA CNAATAGACG   3780
ATTGCAGTAG AATGAGAGTG GTGGTCTAAN CAGTACATGT CCTGATGTTG CTCGGACAGT   3840
TACTACNCCA AGAGTACCCC CTGCCATTGTC AGGGTTAGCA TCTCCTGGAA GCCTCATGTA   3900
AATGAAGAAT TTCATGCTCC ATCCAGGACC TAATGAATAA GAATCTGCAT TTTAGCAAGA   3960
CCCTCATATG ATTCATATAC ACTTTTTTTT TTTTTTTTA GATGGAGTCT CACTCTGTC    4020
```

FIG. 14G

```
GCCCAGGCTG  GAGTGCAATG  GCATGATCTT  GGCTCACTGC  AACCTCTGCC  TCCCGGGTTC  4080
AAGTGATTCT  CCTGTCTCAG  CCTCCCTAGT  AGCTGGGACT  ACAGGTGCAT  GCCACAGTGG  4140
CTGGCTAATT  TTTGTATTTT  TAGTAGAGAC  AGGGTTTCAC  CATTTTGGTC  AGGCTGGTCT  4200
TGAACTCATG  ACCTCCGGTG  ATTCCCCCGC  CTCGGCTTCC  CAAAGTGCTG  GGATTACAGA  4260
CATGAGCCAC  CACACCCGCC  TTATTCGTAT  ACNCATTTAA  TTCTGAGAAG  CACTCTATAG  4320
AAAATAAGAA  TAAGAAAATA  TTGGGCTCAC  AGGTGACATT  AATAAGTAAC  TTTATCGAGT  4380
ACCCCAAATT  TTACCTATGT  TTGGAAGATG  GGGTTAAAAG  GACACATTGA  AAACAAGAAC  4440
TCATTGTGGC  TTTTTTTTCC  TCCTTTTTGA  ACAGTTTTCT  ATTTCTGGAA  TGTTGTCAAT  4500
TATATCTGAA  AGGAGAAATG  CAACATATCT  GGTGAGTTGC  CCGTTTCTGT  CTTTGTCCAT  4560
CCTTGAAAAG  ATAAGAAGAA  CAGAGTTTTA  AGAGTCTTAA  GGGAAACACA  TCTTTGTCTC  4620
CTATATTACT  TGTGAATGTG  GATATATGAT  TTTGTTTCAA  TCTATTTTGT  GTCCTAAGGC  4680
```

FIG. 14H

```
TTTTGCAAC AGAAGTTGGA TATATCATTA GAAACATAAA TTGTACCATT TAACATACAT   4740
GAAGTTTATG TTTACCTTGA CGTTCTTCTA AAAAGTGTCC TACACCGGCA TTGTCCTTGT   4800
AGGCATATTC ACATGATCAA ATAAAATAAT TAGTTTTCAA TTAAGGAGAA TATTTGAGGA   4860
AAGACCGTAC GTGTTCATGT GGTTCCTGAA GGCAGTCCAG TGAGAAAGTA ATATATGCTT   4920
CATTAAACAA TGCGGACATT TTCAGGGTTT CCCTTTTTAA CCAAAATTTG GAAGCAATGT   4980
GGAATTACT GGATGCATCC AGCCCTGAAA TGAAGATAGG TTTATTGAAT GTGCCAGCAA   5040
GTGCAGGCCC AGGTCTGAGT GTTCTTCATT ATTATCAGGT GAGAGGAAGC CTGGGAGCAA   5100
ACACTGCCAG CAGCATAGCT GGGGGAACGG GAATTACCAT CCTGATCATC AACCTGAAGA   5160
AGAGCTTGGC CTATATCCAC ATCCACAGTT GCCAGAAATT TTTTGAGACC AAGTGCTTTA   5220
TGGCTTCCTT TTCCACTGTA TGTATTTTTT TTTGTGTGGG AAGACTAAGA TTCTGGGTCC   5280
TAATGTAAGT AAGAAGCCCT CTTCCCCTGT TCCATGAACA CCATCCTTTT CTGTAACTTC   5340
```

FIG. 14I

```
TATTACACAG TATAGTGGTT CTGTAAGTTC ACACAGCCCA GGGAGATGCT GGCTGCCCAC    5400
TCCCCTCAAC CCAGGCAAAT TCCTCGGGGT TAAAGTTATC TACTGCAAGT GACGATCTCT    5460
GGGTTTTCT GTGCCTGTGT TTGTGTGTGT GTGTGTGTGT GTGTGTGTGT GTATGTGTCA    5520
CTTTAAAAGG ACTGGTCAGA TGGTAGGGAG ATGAAAACAG GAGATGCTAT AAGAAAATAA    5580
ACTTTTGGGG CGAATACCAA TGTGACTCTT TTTGTTTGTC ATTTGTTGCT GTTCAATAGG    5640
AAATTGTAGT GATGATGCTG TTTCTCACCA TTCTGGGACT TGGTAGTGCT GTGTCACTCA    5700
CAATCTGTGG AGCTGGGGAA GAACTCAAAG GAAACAAGGT AGATAGAAGC CCGATATAAA    5760
ATCTTGAATG ACAGGTTAAC GAATTGGAGC TTTATTCCTT AAAATATGGC CTGGGTTTTC    5820
TGAAACATTT CTTCCAGAAA ATAGTTTCTC CAAGTTTTAT TACTTTGGTT TACAAATCTC    5880
ACATTTAAAT CACATTTTAT ACCATAAGTA GCACACATTT CATAATATTC CTCTGAATGA    5940
GGGTTGGGAT AATAGGACTG ATATGTTAGA AATGCCTTAA AGTGTGTGGA GCATGAGAGA    6000
TGGATGTACA GAAGGCTTGT GAGGAAACCA CCCAGGTATC TGGCCTTGTT TTCTGCCCCA    6060
```

FIG. 14J

```
GAACTAGCCG CCTATTCCTG TTTCTGTTTT ATTCCTTTGT TTCTTGACTT TTCCTTTCCA   6120
ACTTGCTCTA AAACCTCAGT TTTCTTTCCT TTCTGATTCA TGACTACCAA ATGTTTCAC    6180
TTGCCTCACC CGTCCATTAC ACCTTTGATA AGAACCACCA GACCTTGTGC TCATGTACTT   6240
GCCCATGTCT GATGGAAGAA ACATACTCTC TCCATCTGTC CACTTTCCTG AGGCATTCAA   6300
GTCTAGCCAC CTTTTAAAAT CACTCTCCTC CAGGCTGGGC ACGGTGTCAC GCCTGTAATC   6360
TCAGCACTTT GTGAGGCTGA GGAGGGCCGA TCACTTGAAG TCAGGAGTTC AAAACCAGCC   6420
TGGCCAAATG GCAAAACCAA ATCTTCTTCA ATTATAACCA AATCTTAAAC CAAATCTCTA   6480
CTAAAAAATA CAACAAAACA AAACAACAAC AACAAAAACA GAAAAGGAAA CATTAGCCCA   6540
GCGTGGTGGC AGTACCTGA GGTTCCAGAT ACTTGGGAGG CTGAAGCAGG AGAATCGCTT    6600
GAGCCCAAGA GATGGAGGTT GCAGTGAGCC GAGATCATGC CACTGCACCA CAGCCCAGGGT  6660
GACAGAGCCA TACTTCCCAG CACATTGGGA GGCCAAAGCT GAAGAATAAT TTGAGGTGAG   6720
```

FIG. 14K

| | | | | | |
|---|---|---|---|---|---|
| GATTTGGAGA | CCAGCCTGGC | CAACATGGTG | AAACTCCGTC | TGTACTAAAA | ATATAAAACT | 6780
| TAGTGGGGCA | TGGGGGCACA | CACCTGTAAT | TTCAGCTACT | TAGGAGGCTG | AGGCAGGAGA | 6840
| ATTGCTTGAA | CCCGGGAGGC | GGAAGTTGCA | GTGAGCCAAG | ATCGTGGCCA | CTGCACTCCA | 6900
| GCCTGGGTGA | CATAGTGAGA | TTCTGTCTCA | AAAAAAATAA | AAGAAATTTA | AAAAATCACT | 6960
| CTCTTCCAAA | GATAGATAAA | TAAGACAGCA | GATATACTAA | GGAATAACCT | CACCAACTTG | 7020
| TCATTGACTG | ACATGATTTC | TTTTGGCCCA | CTTGGCCAGC | TAGTCTGTT | TGGTTTTCTG | 7080
| GAAATGAAAG | AAATAAATCAG | AGTTTAATGA | CAGAGAGCGT | GAGACCCAGA | AAGACAAAAG | 7140
| TAGATGAGGT | AAGTCTCTTG | AGCGAGACTT | CTAGGGATGG | GAAATTTGTG | GTGATTGATA | 7200
| TGAAATGATT | TTTCCCTTAT | CAGGTTCCAG | AGGATCGTGT | TTATGAAGAA | TTAAACATAT | 7260
| ATTCAGCTAC | TTACAGTGAG | TTGGAAGACC | CAGGGGAAAT | GTCTCCTCCC | ATTGATTTAT | 7320
| AAGAATCACG | TGTCCAGAAC | ACTCTGATTC | ACAGCCAAGG | ATCCAGAAGG | CCAAGGTTTT | 7380

FIG. 14L

| | | | | |
|---|---|---|---|---|
|GTTAAGGGGC|TACTGGAAAA|ATTTCTATTC|TCTCCACAGC|CTGCTGGTTT|TACATTAGAT|7440|
|TTATTCGCCT|GATAAGAATA|TTTGTTTCT|GCTGCTTCTG|TCCACCTTAA|TATGCTCCTT|7500|
|CTATTTGTAG|ATATGATAGA|CTCCTATTTT|TCTTGTTTTA|TATTATGACC|ACACACATCT|7560|
|CTGCTGGAAA|GTCAACATGT|AGTAAGCAAG|ATTTAACTGT|TTGATTATAA|CTGTGCAAAT|7620|
|ACAGAAAAAA|AGAAGGCTGG|CTGAAAGTTG|AGTTAAACTT|TGACAGTTTG|ATAATATTTG|7680|
|GTTCTTAGGG|TTTTTTTTT|TTTTAGCATT|CTTAATAGTT|ACAGTTGGGC|ATGATTTGTA|7740|
|CCATCCACCC|ATACCCACAC|AGTCACAGTC|ACACACACAT|ATGTATTACT|TACACTATAT|7800|
|ATAACTTCCT|ATGCAAATAT|TTTACCACCA|GTCAATAATA|CATTTTTGCC|AAGACATGAA|7860|
|GTTTTATAAA|GATCTGTATA|ATTGCCTGAA|TCACCAGCAC|ATTCACTGAC|ATGATATTAT|7920|
|TTGCAGATTG|ACAAGTAGGA|AGTGGGGAAC|TTTTATTAAG|TTACTCGTTG|TCTGGGGAGG|7980|
|TAAATAGGTT|AAAAACAGGG|AAATTATAAG|TGCAGAGATT|AACATTTCAC|AAATGTTTAG|8040|
|TGAAACATTT|GTGAAAAAAG|AAGACTAAAT|TAAGACCTGA|GCTGAAATAA|AGTGACGTGG|8100|

FIG. 14M

```
AAATGGAAAT AATGGTTATA TCTAAAACAT GTAGAAAAAG AGTAACTGGT AGATTTTGTT   8160
AACAAATTAA AGAATAAAGT TAGACAAGCA ACTGGTTGAC TAATACATTA AGCGTTTGAG   8220
TCTAAGATGA AAGGAGAACA CTGGTTATGT TGATAGAATG ATAAAAAGGG TCGGGGCGGG   8280
AGGCTCACGC CTGTAATCCC AGCCCTTTGG GAGGCCGAGG TGGGCAGATC ACGAAGTCAG   8340
TAGTTTGAGA CCAGCCTGGC CAACATAGTG AAACCCCGTC TCTACTAAAA ATACAAAAAA   8400
AAAATTAGCT GGGTGTGGTG GCAGTCACCT GTAGTCCCAG CTACTTGGGA GGATGAGGCA   8460
GGAGAATCGC TTGAACCTGG GAGGCGGAGG TTGCAGTGAG CCGAGATCGC ACCAGTGCAC   8520
TCCAGCCCTG GTGACAATGG GAGACTCCAT CTCAAAAAAA AAAAAAAAAA AAAAAGATA   8580
AAAAGTCAGA AATCTGAAAA GTGGAGGAAG AGTACAAATA GACCTAAATT AAGTCTCATT   8640
TTTTGGCTTT GATTTTGGGG AGACAAAGGG AAATGCAGCC ATAGAGGGCC TGATGACATC   8700
CAATACATGA GTTCTGGTAA AGATAAAATT TGATACACGG TTTGGTGTCA TTATAAGAGA   8760
```

FIG. 14N

```
AATCATTATT AAATGAAGCA AGTTAACACT CTAAGAGAAT TATTTGAGA TAGAAGTGAA     8820
GCTAAGCTAA ACTTCACATG CCTATAATTG GAGGGAAAAA CTAAGGATAA AATCTAGCCT    8880
AGAAGATACA ATAATTAGTC ATAAACATGC ATTGTGAAAC TGTAGAGAGC AGGTAGCCCA    8940
AAATAGAGAA AGATTAGATA AAGAGAAAAT AAGTATCCAT CAGAGACAGT ATCTCTAGGC    9000
TTGGGCAAGA GAAAAGTCCA CAGTGATAAG CAACTCCACC TAAGGCATGA ATATGCGGCA    9060
GAGAAAACAG CAATAGTGAA TGAATGCAAA AGGTGCTGAG CAAATTCCAC ACATGAGTAT    9120
TGTGCATGAG TAAATGAATA AAACATTTGC AAAGACCTTT AGAGAAAGAG AATGGGAGCA    9180
TATGTGCGAA ATAAGATAGT TGATTATGAA TAGAAGGTAG TGAAGAAAAG CAAGCTAAGA    9240
AAAAATTCTG TTTATAAAAG AAGGAAAAGA TAGTTTATGT TTTTAGCCTA AGTATAAGAG    9300
TCCTACAGAT GGACTGAAAA AAATCAGTCT GAGAGTATTA GTCACAATTA ATGAAATAAT    9360
TACATTTTAT GTATTGAGGA AAAAGGTGAC TGCCAAGATT AAAGGTGAC AGGTAGATGT TAATTCCCT    9420
```

FIG. 140

```
AGATTGTGAA AGTGATCACG ACAATCACAC AACAAATAAT TAAGTGACTT GGTATGCTTT    9480
ATTTAATTGT AGGGCCTGAG GTTTTCCATT CTCATTTTTC TAAAATACAA TTTTGTTTCT    9540
CCAAATTTGA CAGCAGAATA AAAACCCTAC CCTTTCACTG TGTATCATGC TAAGCTGCAT    9600
CTCTACTCTT GATCATCTGT AGGTATTAAT CACATCACTT CCATGGCATG GATGTTCACA    9660
TACAGACTCT TAACCCTGGT TTACCAGGAC CTCTAGGAGT GGATCCAATC TATATCTTTA    9720
CAGTTGTATA GTATATGATA TCTCTTTTAT TTCACTCAAT TTATATTTTC ATCATTGACT    9780
ACATATTTCT TATACACAAC ACACAATTTA TGAATTTTTT CTCAAGATCA TTCTGAGAGT    9840
TGCCCCACCC TACCTGCCTT TTATAGTACG CCCACCTCAG GCAGACACAG AGCACAATGC    9900
TGGGGTTCTC TTCACACTAT CACTGCCCCA AATTGTCTTT CTAAATTCA  ACTTCAATGT    9960
CATCTTCTCC ATGAAGACCA CTGAATGAAC ACCTTTTCAT CCAGCCTTAA TTTCTTGCTC   10020
CATAACTACT CTATCCCACG ATGCAGTATT GTATCATTAA TTATTAGTGT GCTTGTGACC   10080
TCCTTATGTA TTCTCAATTA CCTGTATTTG TGCAATAAAT TGGAATAATG TAACTTGATT   10140
```

FIG. 14P

```
TCTTATCTGT GTTTGTGTTG GCATGCAAGA TTTAGGTACT TATCAAGATA ATGGGGAATT    10200
AAGGCATCAA TAAAATGATG CCAAAGACCA AGAGCAGTTT CTGAAGTCCT CCTTTTCATC    10260
AGCTCTTTAT CAAACAGAAC ACTCTATAAA CAACCCATAG CCAGAAAACA GGATGTAGGA    10320
ACAATCACCA GCACACTCTA TAAACAACCC ATAGCCAGAA AACAGAATGT AAGGACAATC    10380
ACCAGCCATC TTTTGTCAAT AATTGATGGA ATAGAGTTGA AAGGAACTGG AGCATGAGTC    10440
ATATTTGACC AGTCAGTCCT CACTCTTATT TACTTGCTAT GTAAACTTGA GAAAGCTTTT    10500
TTCTCTTTGT GAACCTCAGG TTTTACATCT GAAAATGAGA AATTTGGAAC AAAAGATTCC    10560
TAACTGGTCT TTCTGTTCCC ATATTCTGTG ATTTTTCAAT ATTTAGGATT TTTGGTAATC    10620
ACAATTACTT AGTTTGTGGT TGAGATAGCA ACACGAATCA GAACTATTTG GTGGACATAT    10680
TTTCAAAGGA GTAGCTCTCC ACTTTGGGTA AAGAAGTGAT GCNGGTCGTG GTGGCTCACG    10740
```

FIG. 14Q

```
CCTGTAATCC CAGCCACTTTA GGGAGGCCAA GGCGGGGTGGA TCACGAGGTC AGGAGATCGA   10800
GACCATCCTG GCTAACACGG TGAAACCCCG TCTCTACTAA AAATACAAA AAATTAGCCA     10860
GGCGTGGTGG CGGGCGCCTG TAGTCCCACG TACTCGGGAG GCTGAGGCAG GAGAATGGCA    10920
TGAACCAGGG AGGCGGAGCT TGCCGTGAGC CGAGATAGCG CCACTGCAGT CCCTCCTGGG    10980
CAAAAGAGCA AGACTGCGTC TCAAAAAAAA AAAAAAAAA AAAAAAAGAA GTGTGTGGAG     11040
TAGCAGGACA CCTGCAACAA TAATATTTTT CTAAATCCCT CTGAAAAATG CTAATCAAAG    11100
GGTTTTTTC CTAAAAATTG TCTTAGAAAT AAAATTCCC CTTTGGGAGA CCGAGGCTGG      11160
CAGATCACGA GGTCAGGAGA TAGAGACCAC GGTGAAACCC CGTCTCTACT AAAAATACTA    11220
AAAATTAGCC GGGGNTGGT GGTGGGTACA CCTGTAGTCC CAGCTACTTG GAGGCTGAGG     11280
CTGGAGAATC ACGTGAAC                                                  11298
```

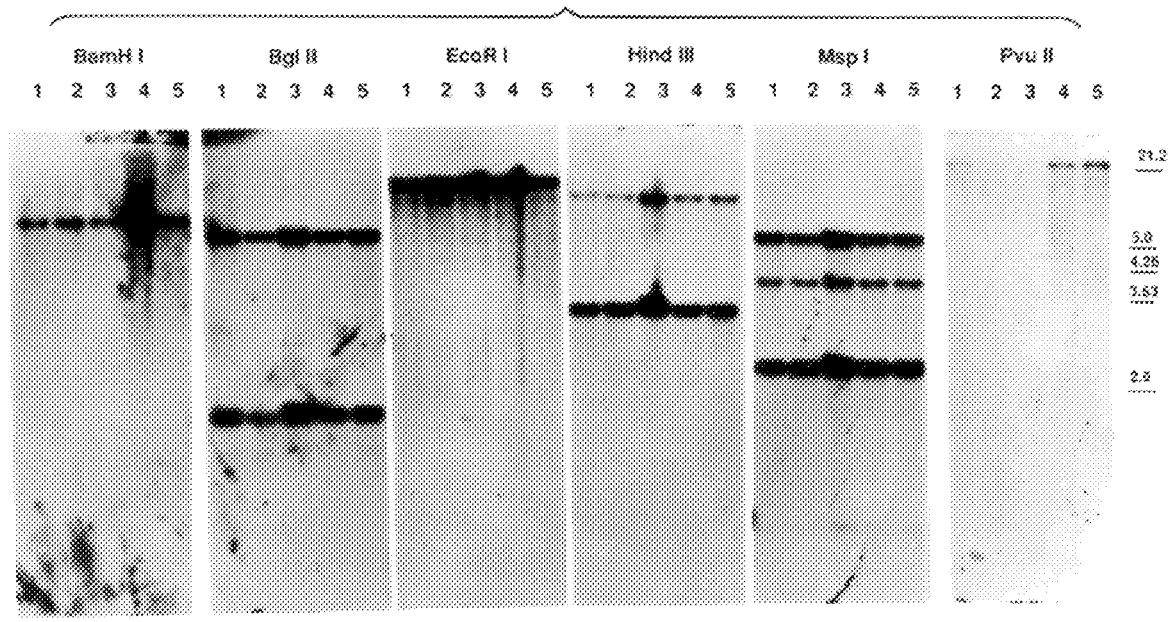

FIG. 19A

```
human MDTES NRRAN LA--L PQEPS SVPAF EVLEI SPQEV SSGRL rat   MDTEn ksRAd LAlpn PQEsp saPdi ElLEa SPp-a kalp-
      ^^^^  .^^^  ^^.^  ^^^.. ^.^.  ^^^^. ^^.-. .^^.-
mouse MDTEn rsRAd LAlpn PQEsS saPdi ElLEa SP---  --a--
      ^^^^  .^^^  ^^.^  ^^^.. ^.^.  ^^^^. ^^--- --.--.

human SVL DISHI EGDIF SSFKA GYPFW GAIFF SISGM LSIIS rat   stL qtsdf ddevl llyrA GYPFW GAvlF vlSGf LSImS
      .^^ .^..^ ..^.^ ...^^ ^^^^^ ^^.^^ ^^^^. ^^^.^
mouse SVL yvSdf deevl llykl GYPFW GAvlF vlSGf LSIIS
      ^^^ .^^.^ .^^^^ ...^. ^^^^^ ^^.^^ ^^^^. ^^^^^ human S CQKFF ETK-C FMASF STEIV VMMLF LTILG LGSAV SLTIC rat   - Ckdit EddgC FvtSF iTElV lMlLF LTILa fcSAV lLilY
      - ^^.^. ^^^.^ ^^.^^ .^^^^ ^^.^^ ^^^^. ^^^^^ ^^.^.
mouse - Cknvt EddgC FvASF tTElV lMMLF LTILa fcSAV lfTIy
      - ^^..^ ^^^.^ ^^^^^ .^^^^ ^^^^^ ^^^^. ^^^^^ ^^^^.
```

FIG. 19B

```
LKSAS SPPLH TWLTV LKKEQ EFLGV TQILT AMICL CFGTV VC
                                                   |
eKpAS pPPqq TWqsf LKKEl EFLGV TQvLv qlICL CFGTV VC
<<<<< <<<<< <<<<< <<<<< <<<<< <<<<< <<<<< <<<<< <<
      .                                   .
-K-A- aPPkq TWrTf LKKEl EFLGa TQILv qlICL CFGTi VC
<<<<< <<<<< <<<<< <<<<< <<<<< <<<<< <<<<< <<<<< <<
      .                                   .

ERRNA TYLVR GSLGA NTASS IAGGT GITIL IINLK KSLAY IHIH
                                                    |
ERkNt lYLVR GSLGA NivSS IAaGl GIaIL IlNLs nnsAY mn-y
<<<<< <<<<< <<<<< <<<<< <<<<< <<<<< <<<<< <<<<< <<<<<
<<<<< .       .     .     .     .     .     .    . .

ERkNt lYLVR GSLGA NivSS IAaGT GIamL IlNLt nnfAY mn-n
<<<<< <<<<< <<<<< <<<<< <<<<< <<<<< <<<<< <<<<< <<<<<
<<<<< .       .     .     .     .     .     .    . .

GAGEE LKGNK VPEDR VYEEL NIYSA TYSEL EDPGE MSPPI DL
                                                  |
riGqE fersK VPdDR lYEEL hvYSp iYSaL EDtrE aSaPv vs
<<<<< <<<<< <<<<< <<<<< <<<<< <<<<< <<<<< <<<<< <<
  .     .     .     .     .     .   .  . .  . .

riGqE LeskK VPdDR lYEEL NvYSp iYSEL EDkGE tSsPv Ds
<<<<< <<<<< <<<<< <<<<< <<<<< <<<<< <<<<< <<<<< <<
  .     .     .     .     .     .     .  . .    .
```

ISOLATION CHARACTERIZATION, AND USE OF THE HUMAN BETA SUBUNIT OF THE HIGH AFFINITY RECEPTOR FOR IMMUNOGLOBULIN E

BACKGROUND OF THE INVENTION

1. Field of the Invention

The present invention relates to DNA segments encoding the $\alpha$, $\beta$, and $\gamma$ subunits of the human high affinity receptor for immunoglobulin E (IgE). The invention further relates to a method of producing the receptor by expressing DNA encoding its $\alpha$, $\beta$ and $\gamma$ subunits in a host cell simultaneously.

2. Related Art Receptors that bind the Fc region of immunoglobulins ("Fc receptors") mediate immunoglobulin transport across membranes, stimulate a variety of cellular activities induced by antigen-antibody complexes, and possibly regulate the biosynthesis of antibodies. Three of the receptors (the receptor for polymeric immunoglobulin (Mostov et al. (1984) Nature (London) 308:37–43), the Fc receptors on macrophages and lymphocytes (Ravetch et al. (1986) Science 234:718–725), and the high affinity Fc, receptor on mast cells and basophils (Kinet et al. (1987) Biochemistry 26:4605–4610; Shimizu et al. (1988) Proc. Natl. Acad. Sci. USA 85:1907–1911; Kochan et al. (1988) Nucleic Acids Res. 16:3584) share a common feature: their immunoglobulin-binding portion contains two or more immunoglobulin-like domains.

The high affinity IgE receptor $Fc_\epsilon RI$ is responsible for initiating the allergic response. Binding of allergen to receptor-bound IgE leads to cell activation and the release of mediators (such as histamine) responsible for the manifestations of allergy. This receptor is a tetrameric complex $\alpha\beta\gamma_2$ which is found on the surface of mast cells and basophils. The $\alpha$ and $\beta$ subunits have not been detected in other hematopoietic cells although the $\gamma$ chains of FceRI are found in macrophages, NK cells and T cells where they associate with the low affinity receptor for IgG ($Fc_\gamma RIII$) or with the T cell antigen receptor.

The genes for $\alpha$ and $\gamma$, both have been localized on human (Le Coniat, 1990) and mouse chromosome 1. (Huppi, 1988; Kinet et al. 1987; Kochan et al. 1988; Shimizu et al. 1988; Ra et al. 1989.) The gene for mouse $\beta$ has been localized on mouse chromosome 19 and is believed to be a single gene (Huppi, 1989). The structures of the $\alpha$ gene in the rat (Tepler, 1989) and of the y gene (Kuster, 1990), but not of the $\beta$ gene have been characterized in the human.

The receptor with high affinity for IgE $Fc_\epsilon RI$ is found exclusively on mast cells, basophils, Langerhans cells, and related cells. Aggregation of IgE occupied $Fc_\epsilon RI$ by antigen triggers both the release of preformed mediators such as histamine and serotonin, as well as stimulation of the synthesis of leukotrienes. It is the release of these mediators that results in the allergic condition.

The most thoroughly characterized $Fc_\epsilon RI$ is that of the rat basophilic leukemia (FEL) cell line. It consists of three different subunits: (1) a 40–50 Kilodalton (Kd) glycoprotein alpha chain which contains the binding site for IgE, (2) a single 33 Kd beta chain and (3) two 7–9 Kd disulfide linked gamma chains (H. Metzger et al., Ann. Rev. Immunol. 4:419–470 (1986)).

Complementary DNA (cDNA) for the rat a subunit has been isolated (J.-P. Kinet et al., Biochemistry 26:4605–4610 (1987)). However, previously there has been no disclosure of the isolation and characterization of the $\beta$ and $\gamma$ subunits nor has it been possible to express IgE- binding by transfected cells (J.-P. Kinet et al., Biochemistry 26:4605–4610 (1987); A. Shimizu et al., Proc. Natl. Acad. Sci. USA 85:1907–1911 (1988)).

Molecular cloning of some of the subunits in rodents and humans has permitted the reconstitution of surface expressed receptor complexes by trasfection. One of the surprising findings from these studies was the differential requirement for surface expression among different species. Cotransfection of the three chains, $\alpha$, $\beta$ and $\gamma$ is required to promote efficient surface expression of the rat (Blank, 1989) or mouse receptor (Ra, 1989). By contrast, some surface expression of the human $\alpha\gamma$ complex can be achieved by cotransfecting $\alpha$ and $\gamma$ alone in fibroblasts suggesting that $\beta$ may not be necessary (Miller, 1989). This result and previous inability to clone the gene for the human $\beta$ subunit raised the possibility that human beta might not exist and that $\alpha\gamma$ complexes might exist naturally in human cells.

The high affinity IgE receptor $Fc_\epsilon RI$ is a tetrameric hetero-oligomer composed of an $\alpha$ chain, a $\beta$ chain and two disulfide-linked $\gamma$ chains (chains and subunits will be used interchangeably herein). The $\beta$ chain contains four transmembrane (TM) segments and long cytoplasmic domains which are thought to play an important role in intracellular signalling. It was very difficult to determine whether a human beta subunit even existed, and if so, to isolate its gene. The present invention has overcome these difficulties and surprisingly provided cDNA clones for the human $\beta$ subunit of $Fc_\epsilon RI$.

The invention still further provides a method of producing the complete human $Fc_\epsilon RI$ receptor, and for inhibiting formation of the receptor or its function, by inhibiting the $\beta$ subunit.

SUMMARY OF THE INVENTION

It is an aspect of this invention to provide nucleic acid segments encoding $Fc_\epsilon RI$ subunits.

It is an aspect of this invention to provide nucleic acid sequences encoding the $\alpha$, $\beta$, and $\gamma$ subunits of $Fc_\epsilon RI$. In particular, this invention relates to DNA sequences. An aspect of the present invention is the structural characterization and the sequence of the complete human $\beta$ gene and cDNA. Successful cloning of the human beta was not expected and was fraught with failures. Attempts to clone the human beta by simply using a rodent beta probe to screen various cDNA libraries failed to isolate a cDNA clone encoding human beta. Only a very short fragment (153 bp) with homology to rodent beta was isolated. However because this fragment may have been a portion of a beta-like molecule such as CD20, known to be homologous to beta in that region, PCR techniques were used to clone the human beta by using the information from the rodent beta sequence. However, although the homologies between human and rodent beta were 69% in the coding region, that was not sufficient for a PCR reaction. Human beta isolated by this method also failed.

The existence of human beta was questioned because human beta was believed not necessary for expression of the alpha-gamma complex. Studies of gene transfer indicated that the transfer by transfection of the three genes for alpha, beta and gamma was necessary for the expression of the rat and mouse receptor. However, transfection of human alpha and gamma was sufficient to promote the surface expression of the human receptor in fibroblasts suggesting that the human beta was not necessary for the surface expression of the human receptor. That result raised the interesting question of the existence of human beta.

Human beta was not necessary for the function of the alpha-gamma complex. Transfection of the cytoplasmic tail of gamma is sufficient for cell activation. Several groups made the observation that the cytoplasmic domain in the gamma chain was sufficient to mediate a number of biochemical signals leading to cell activation. These signals include tyrosine kinase activation, hydrolysis of phosphoinositides, calcium mobilization, production of IL2 in T cells, degranulation of mast cells and cell killing. It was demonstrated that the cytoplasmic domains of gamma contain a motif of 10–12 amino-acid residues responsible for cell activation. This motif is sufficient to trigger many different signals in different cells. It is transferable, and seemed to be interchangeable. Again these findings raised the question of the existence of human beta. If the gamma chain is sufficient for cell activation, perhaps there was no need for a beta.

The inability to clone the human beta or even to detect transcripts for human beta in human cells (by using rat or mouse probes) also raised the question of the existence of human beta.

Cloning required inventive methods and persistence. The 153 bp fragment used to screen further cDNA libraries did not work. However, assuming that the 153 bp could be part of human beta even though the homology was only about 70%, a 25 kb genomic clone was found. Smaller inserts were found which seemed to hybridize specifically with oligonucleotide probes corresponding with rat beta sequences. All these inserts (a total of 11 kb) were sequenced to reconstitute the different exons in the quest for those encoding human beta. Using what should be the beginning of the first exon and the end of the coding sequence in the seventh exon from the putative human beta gene, a putative cDNA human beta sequence was generated by PCR (by using first strand reverse transcripts from human basophils as templates for the PCR reaction.)

It was demonstrated that the gene and cDNA isolated encoded human beta. The isolated gene and cDNA could correspond to a beta-like or CD20-like molecule which is homologous to rodent beta. However, the homology of 69% is not a criteria for the demonstration that these sequences encode human beta. Co-expression of alpha, beta and gamma in transfectants was preferred for the demonstration that the cDNA generated is indeed encoding human beta. However these experiments were not successful for the following reasons:

1. Co-transfection of human alpha and gamma is sufficient for surface expression and functional reconstitution of the receptor on fibroblasts.
2. When human beta cDNA is co-transfected with alpha and gamma, the efficiency of transfection is not increased.

Therefore conditions were used where co-transfection of alpha and gamma does not work to see if human beta and not CD20 could promote expression of the complete complex. This was done by truncation of the cytoplasmic tail of human gamma. In these conditions, co-transfection of human alpha with truncated human gamma does not result in the expression of the complex. However, co-transfection of human beta (but not of CD20) with alpha and truncated gamma resulted in the expression of a functional complex capable of binding IgE. This assay showed that human beta could associate specifically with the two other chains.

The new results demonstrated the previously unsuspected importance of human beta. The two FIGS. 20 and 21 show the results obtained from FACS analysis (IgE binding) of cells transfected as explained herein. In FIG. 21 the transfection of human alpha and gamma in COS-7 cells is shown to be sufficient for expression of the alpha-gamma complex on the surface of the transfectants. It also shows that human beta and not rat beta associate efficiently with human alpha and that therefore, rat beta cannot replace human beta.

In FIG. 20 transfection of alpha-gamma in KU812 showed very little expression of receptors. The level of expression is similar to the level obtained after transfection of beta and gamma. Therefore this level may be attributable to the endogenous alpha (for beta and gamma transfection) or to the endogenous beta (for alpha and gamma transfection). By contrast the level of expression after co-transfection of the three cDNAs is very substantial.

The conclusions are:

1. In mast cells and basophils, what regulates the level of expression of the receptor may be different than in fibroblasts.
2. In human mast cells and basophils, receptor expression requires the presence of alpha, beta and gamma whereas in transfected fibroblasts, human alpha and gamma are sufficient. The human beta subunit gene spans approximately 10 kb and contains seven exons. There is a single transcription initiation site preceded by a TATA box. The first exon codes for the 5' untranslated region and a portion of the N-terminal cytoplasmic tail. Transmembrane (TM) 1 is encoded in exon 2 and 3, TM 2 in exon 3 and 4, TM 3 in exon 5 and TM 4 in exon 6. The seventh and final exon encodes the end of the C-terminal cytoplasmic tail and the 3' untranslated sequence. The human $\beta$ gene appears to be a single copy gene.

Two corresponding transcripts, detected as a doublet around 3.9 kb, are present in cells of mast cell and basophil lineage from different individuals but not in the other hematopoietic cells tested. The human $\beta$ protein is homologous to rodent $\beta$. The consensus amino acid sequences for human, mouse and rat $\beta$ show 69% identical residues.

It is a further aspect of the invention to provide polypeptides corresponding to the $\alpha$, $\beta$, and $\gamma$ subunits of $Fc_\epsilon RI$, more particularly to the human $\beta$ subunit isolated from its natural environment. This may be defined to include the amino acid sequences of the polypeptides either produced by recombinant methods, or synthesized by apparatus known to those of skill in the art, or isolated and purified by protein isolation and purification methods. The polypeptides comprise the entire amino acid sequence, or selected portions thereof, for example, portions (domains) of the human beta subunit that are essential for (1) assembly of the receptor; (2) cell activation, and/or (3) complexing with the alpha and gamma subunits. "Natural environment" may be defined to include the subunits in the cells in which they naturally occur, in the form and with other types of proteins and cellular components generally in structural or functional association with the subunits.

It is another aspect of the invention to provide a recombinant DNA molecule comprising a vector and a DNA segment encoding the $\alpha$, $\beta$, or $\gamma$ subunits of $Fc_\epsilon RI$.

It is a further aspect of the invention to provide a cell that contains the above-described recombinant DNA molecules.

It is another object of the invention to provide a method of producing polypeptides having amino acid sequences corresponding to the $\alpha$, $\beta$, and $\gamma$ subunits of $Fc_\epsilon RI$, both in rodent and human species.

Analysis of the surface expression of transfected receptors in fibroblast-like cells indicates that human $\alpha\gamma$ and $\alpha\beta\gamma$ complexes are expressed with comparable efficiency.

Unexpectedly, assembly rules were different in other human cells. In addition, human β interacts with human α more efficiently than does rat β. By contrast, both rat and mouse β interact with their corresponding α chains much more efficiently than does human β, demonstrating a strong species specificity of the α–β interaction.

It is a further object of the invention to provide a method of producing a functional $FC_\epsilon RI$ receptor.

In one embodiment, the present invention relates to DNA segments that code for polypeptides having amino acid sequences corresponding to the α, β, and γ subunits of $Fc_\epsilon RI$.

In another embodiment, the present invention relates to polypeptides having amino acid sequences corresponding to the α, β, and γ subunits of $Fc_\epsilon RI$.

In a further embodiment, the present invention relates to recombinant DNA molecules comprising a vector and a DNA segment that codes for a polypeptide having an amino acid sequence corresponding to the α, β or γ subunits of $Fc_\epsilon RI$.

In yet another embodiment, the present invention relates to a cell that contains the above-described recombinant DNA molecule.

In a further embodiment, the present invention relates to a method of producing polypeptides having amino acid sequences corresponding to the α, β, and γ subunits of FCERI.

In another embodiment, the present invention relates to a method of producing a functional FCERI receptor comprising introducing into a host cell DNA segments encoding the α, β, and γ subunits of $Fc_\epsilon RI$; and effecting expression of said DNA segments under conditions such that said receptor is formed. Expression of the receptor on the surface of cells COS-7 or CHO is achieved by the present invention when the cDNA for all three subunits of FCERI are simultaneously cotransfected. This success in expression of IgE binding permits detailed analysis of the IgE-receptor interaction and thus enables the development of therapeutically effective inhibitors.

An aspect of the invention is to stem the cascade of allergic responses resulting from aggregation of the high affinity receptor for IgE, by inhibiting the essential participation of the human beta subunit. The beta subunit is the target to inhibit receptor aggregation and/or the function of the translate signal. Such an inhibition has widespread applications for prevention and treatment of allergic diseases because the undesirable events cascading from the receptor-IgE interaction are allergen independent and arise from various cell types: mast cells, basophils, Langerhans cells and the like.

Inhibitors of beta include chemical preparations that attack the structure or function of the chain, anti-sense nucleic acid sequences, amino acid sequences capable of binding to the beta subunit polypeptide, and monoclonal antibodies directed to the subunit.

Effective amounts of the beta subunit inhibitors will be determined after in vitro cell assays, assays in animal models, and clinical trials.

Effective amounts of the inhibitors will be combined with a pharmaceutically acceptable carrier. Because of the variety of cell types in which the allergic response is related to the $Fc_\epsilon RI$, and because the reaction is allergen independent, route of administration may be either systemic or atopic.

Candidate inhibitor substances are tested by methods disclosed herein.

In vitro assays for inhibitor substances are provided through host cells transfected with nucleic acid sequences for encoding the human alpha, beta and gamma subunits, complexed or incubated with inhibitors. Cell activation effected by the $Fc_\epsilon RI$ receptor is triggered and compared in the presence versus absence of inhibitors. Many assays are available.

Further objects and advantages of the present invention will be clear from the following description and examples.

BRIEF DESCRIPTION OF THE DRAWINGS

FIG. 1. The nucleotide sequence (SEQ ID NO:10) and predicted amino acid sequence (SEQ ID NO:11) of human $Fc_\epsilon RI$ alpha cDNA are shown.

FIG. 2. The amino acid sequence homology of rat $Fc_\epsilon RI$ alpha subunit (R, SEQ ID NO:12), human $Fc_\epsilon RI$ alpha subunit (A, SEQ ID NO:13), and mouse $Fc_\epsilon RI$ alpha subunit (M, SEQ ID NO:14) are shown. The regions of identity between the three are boxed. The number one position corresponds to the site of the predicted mature N-terminus of each protein.

FIG. 6A(1)–(6) Nucleotide (SEQ ID NO:22) and deduced amino acid (SEQ ID NO:23) sequences of the cDNA coding for the β subunit. Beginning at the arrowhead (▼), an alternative sequence FIG. 6B was observed in six clones. The putative transmembrane domains are underlined. The tryptic peptides of the β subunit, from which the amino acid sequences were determined directly, are bracked (< >). A putative poly (A) signal near the end is underlined. (FIG. 6B) Continuation of the nucleotide sequence (SEQ ID NO:24) of the deleted form of β cDNA, 3' to the junction indicated in A (▼).

Figure 3:
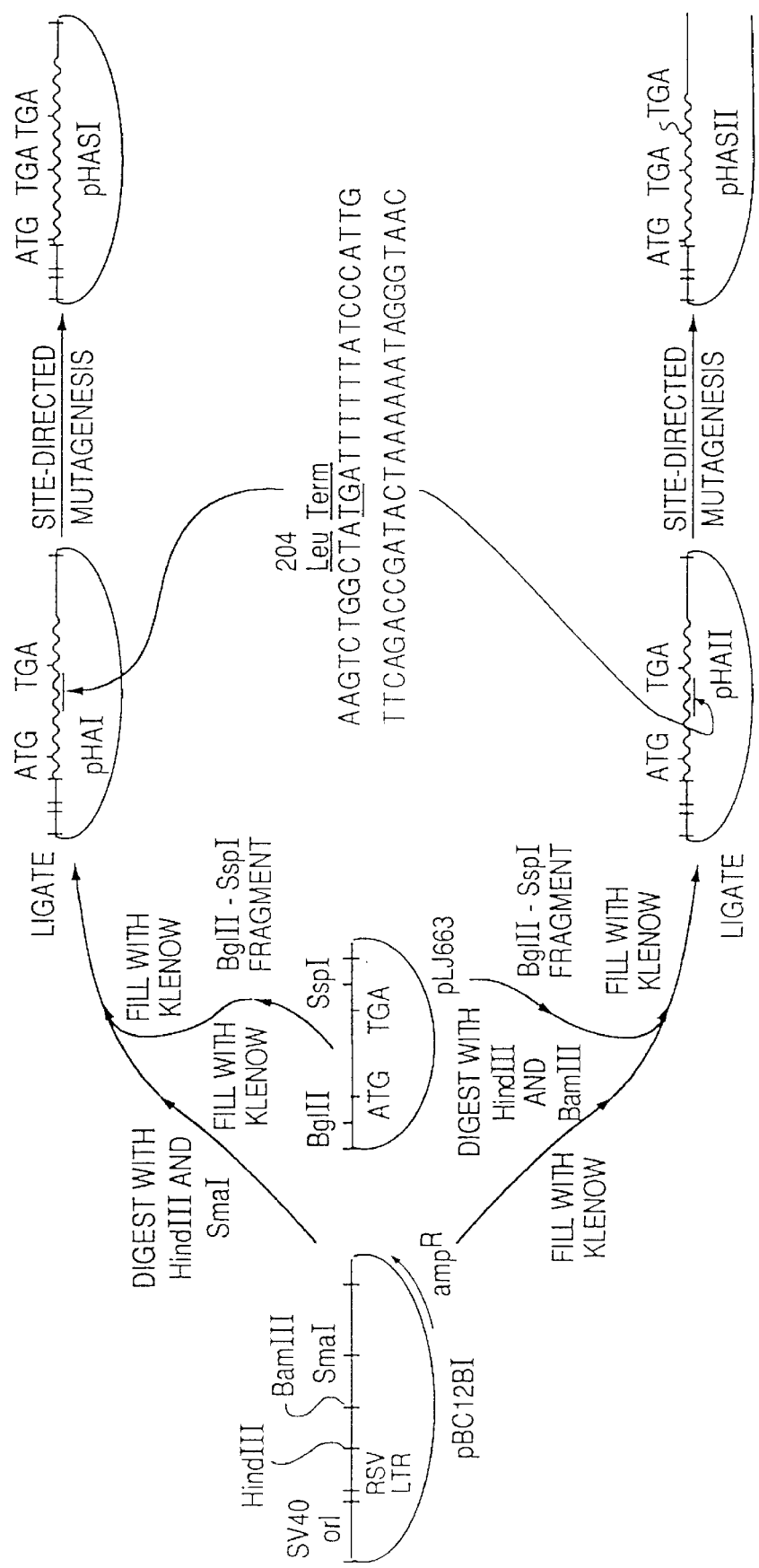
FIG. 3. A flow chart showing the construction of eukaryotic expression vectors which direct the synthesis of a complete biologically active $Fc_\epsilon RI$ alpha chain (pHAI, PHAII) or a soluble, secreted, biologically active $Fc_\epsilon RI$ alpha chain (pHASI, pHASII) is presented. The sequences shown in the pEVA construct are also shown in SEQ ID NOs. 15–17; the sequences shown in the EVHA construct are also shown in SEQ ID NOs. 18 and 19; the sequences shown in the pEVHAS construct are also shown in SEQ ID NOs. 20 and 21.

A control incubation contained no cDNA (lane 4). The mixtures were allowed to react with monoclonal antibodies to the β subunit after a clearing immunoprecipitation. The specific washed precipitates were dissolved in sample buffer and electrophoresed: lanes 2 and 4, mAbβ(JRK); lane 3, mAbfl(NB); lane 5, irrelevant monoclonal antibody [mAbβ (LB)]. An autoradiograph of the 12.5% polyacrylamide gel on which the specimens were analyzed under reducing conditions is shown. (B) Localization of one epitome to the NH$_2$-terminal peptide of the β subunit. A β cDNA-containing vector was digested with HhaI before transcription using T7 polymerase. The resulting mRNA was translated to generate an NH$_2$-terminal peptide of the β subunit β(amino acid 1–21) labeled with [$^{35}$S]methionine. The mixture was allowed to react with mAbβ(JRK) (lane 1) and the irrelevant mAb(LB) (lane 2). The precipitates were analyzed on a 17% gel under nonreducing conditions. (C) Expression by E. coli of a COOH-terminal fragment of the B subunit. A HinfI fragment, containing nucleotides 499–787, was subcloned into an E. coli expression vector (Crowl et al. (1985) Gene 38:31–38) and extracts were prepared. The proteins were electrophoresed as in A and transferred to nitrocellulose paper. The latter was allowed to react sequentially with monoclonal antibody mAbB(NB), developed with alkaline phosphatase-conjugated goat anti-mouse IgG (Fc), and developed in the usual way (Rivera et al. (1988) Mol. Immunol.). An enlargement of the lower half of the immunoblot is shown. Lane 1, extract from transformant without insert; lane 2, extract from transformant with insert in wrong direction; lane 3, extract from transformant with insert correctly oriented. (D) Reactivity of β subunits with polyclonal antibodies induced by E. coli-expressed HinfI fragments. Purified IgE-receptor complexes were electrophoresed, transferred to nitrocellulose paper, and allowed to react with antibodies and subsequently with an appropriate alkaline phosphatase-conjugated anti-immunoglobulin antibody. Lane 1, mAbβ(JRK); lane 2, mAbβ(NB); lane 3, immune serum to fragment A; lane 5, immune serum to fragment B; lanes 4 and 6, preimmune sera corresponding to the immune sera in lanes 3 and 5, respectively; lanes 7 and 8, second antibody only. This gel was run without molecular weight standards.

Figure 8:
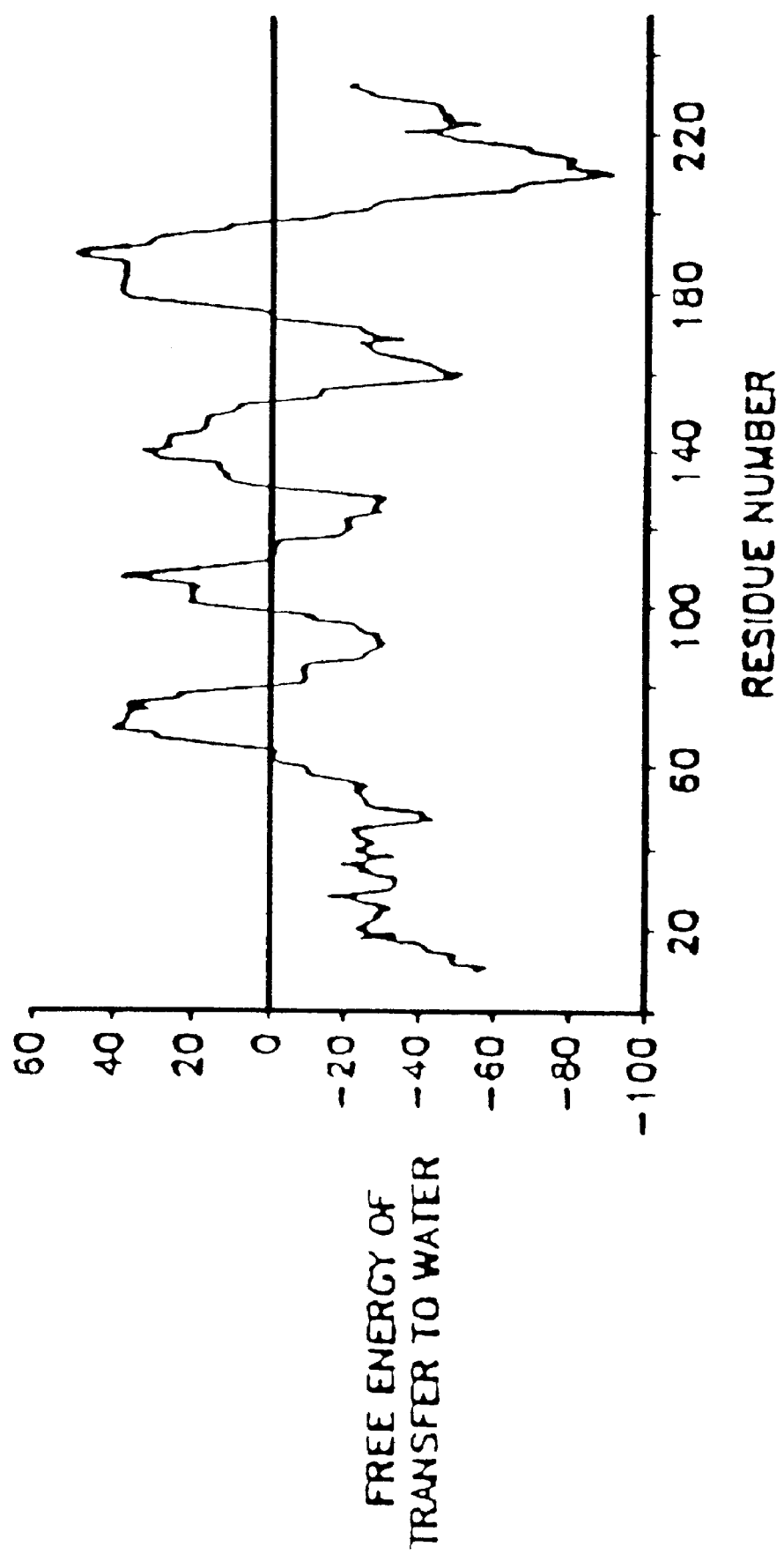

FIG. 8. Hydropathicity plot of predicted sequence for the β subunit. The procedure and hydropathicity scale recommended by Engleman et al. (Engelman et al. (1986) Annu. Rev. Biophys. Biophys. Chem. 15:321–353) was used. The net hydropathicity value for the 20 amino acids for each successive "window" is plotted at the position corresponding to the 10th residue. A net free energy of >20 kcal (1 cal=4.18 J) for transfer to water suggests a transmembrane segment (Engelman et al. (1986) Annu. Rev. Biophys. Biophys. Chem. 15:321–353).

FIG. 9. Nucleotide sequence (SEQ ID NO:26) of the γ subunit of rat Fc$_\epsilon$RI and the amino acid sequence (SEQ ID NO:27) that it predicts. The putative transmembrane domain is underlined. Amino acid resides are numbered starting with the first residue of the mature protein. Residues 5' to residue 1 have negative numbers and include the residues encoding a putative signal peptide according to the criteria of G. von Heijne (Nucleic Acids Res. 14:4683–4690 (1986)). The N-terminal and C-terminal cleavage sites are indicated by an arrow. The four tryptic peptides which were covered and sequenced are bracketed. An asterisk denotes an ambiguous residue in the sequence of the first tryptic peptide.

FIG. 10. Hydropathicity plot of predicted sequences of Fc$_\epsilon$RI α subunit (panel A), β subunit (panel B) and γ subunit (panel C). The hydropathicity scale is according to Engelman et al. (Ann. Rev. Biophys. Biophys. Chem. 15:321–353 (1986)). The summed hydropathicity values for the 20 amino acids in successive "windows" is plotted at the position corresponding to the tenth residue.

Figure 11C:
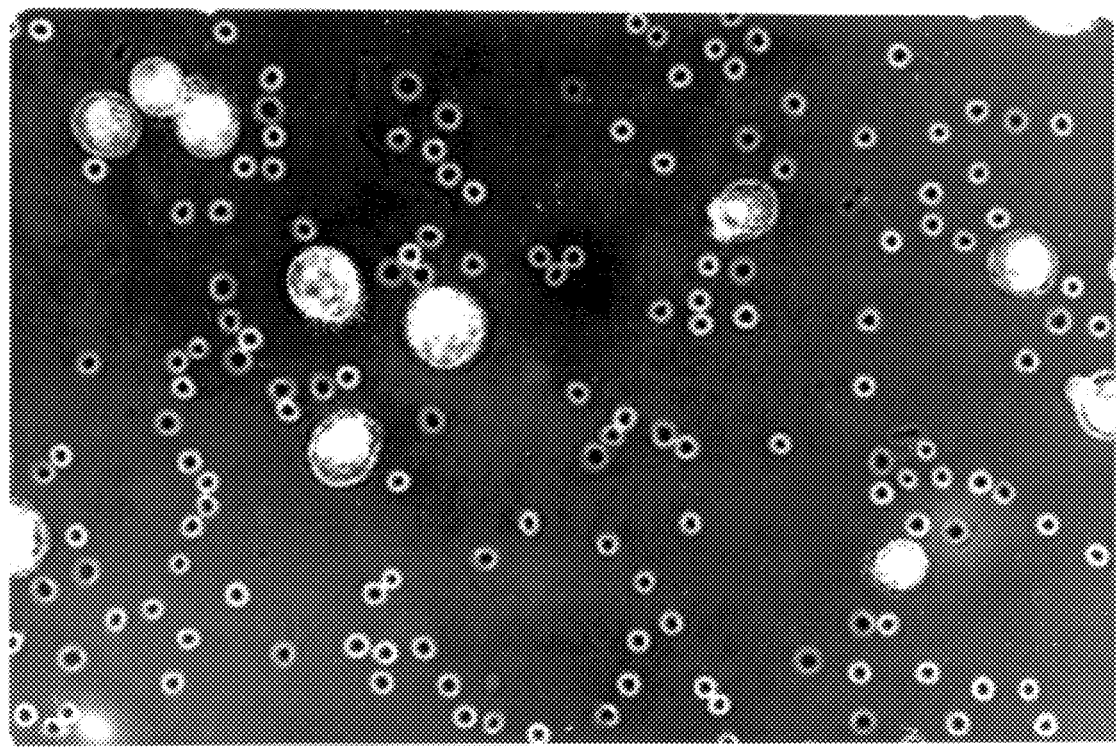
Figure 11D:
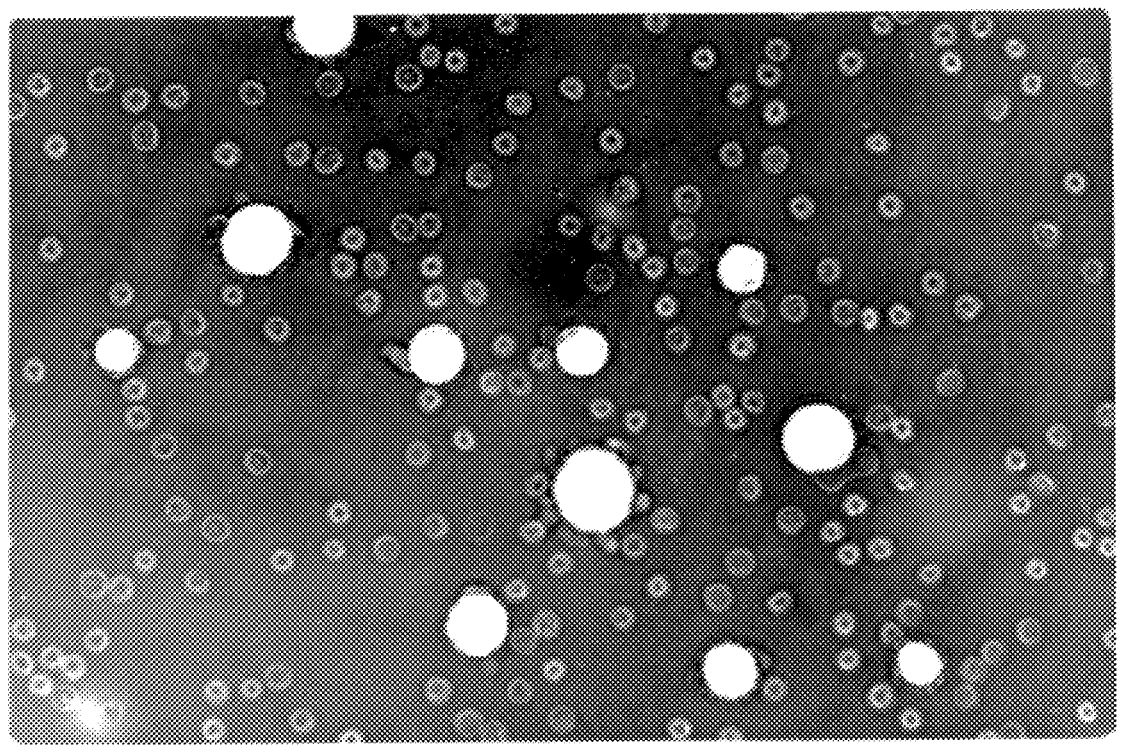
Figure 12A:
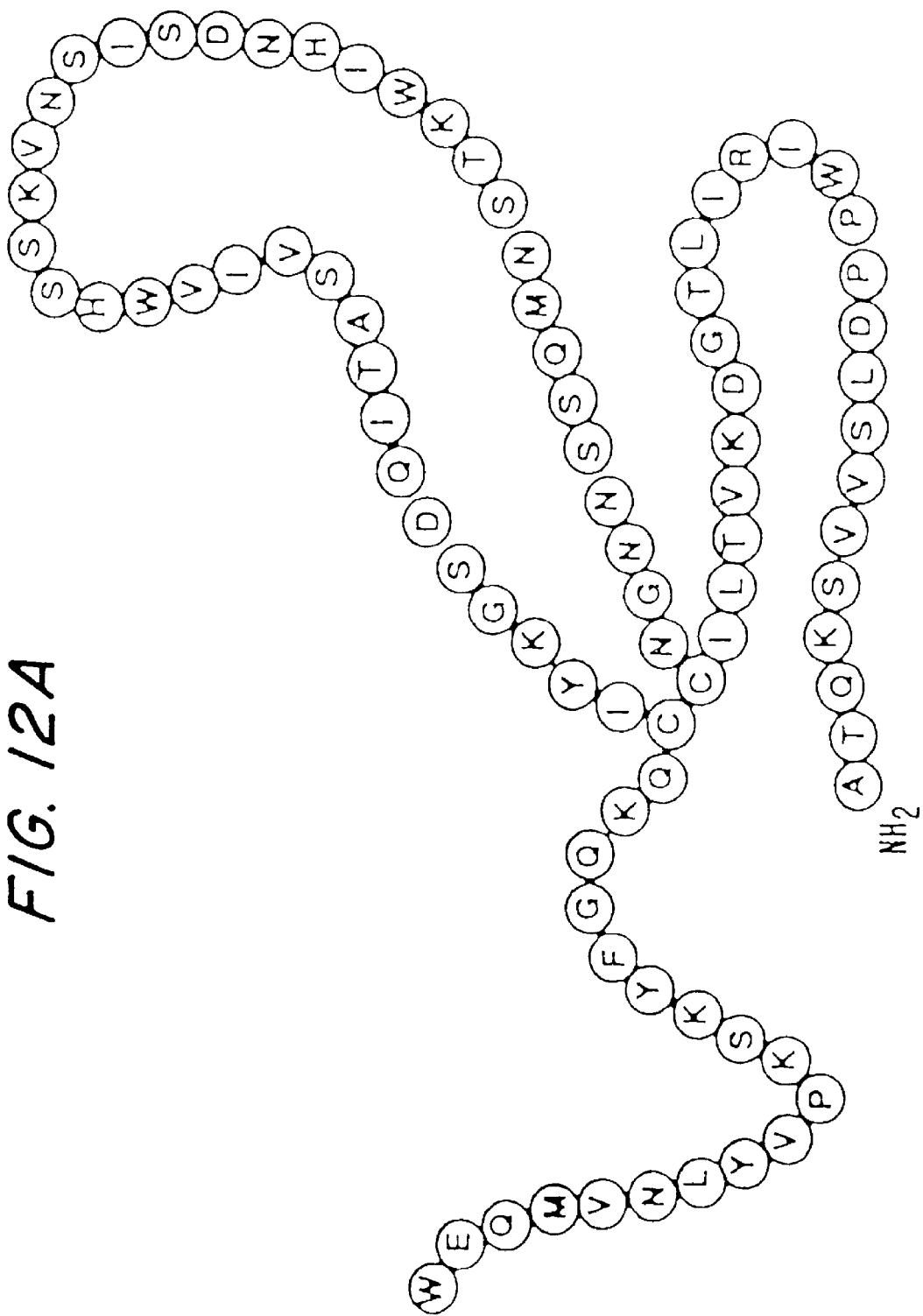
Figure 12B:
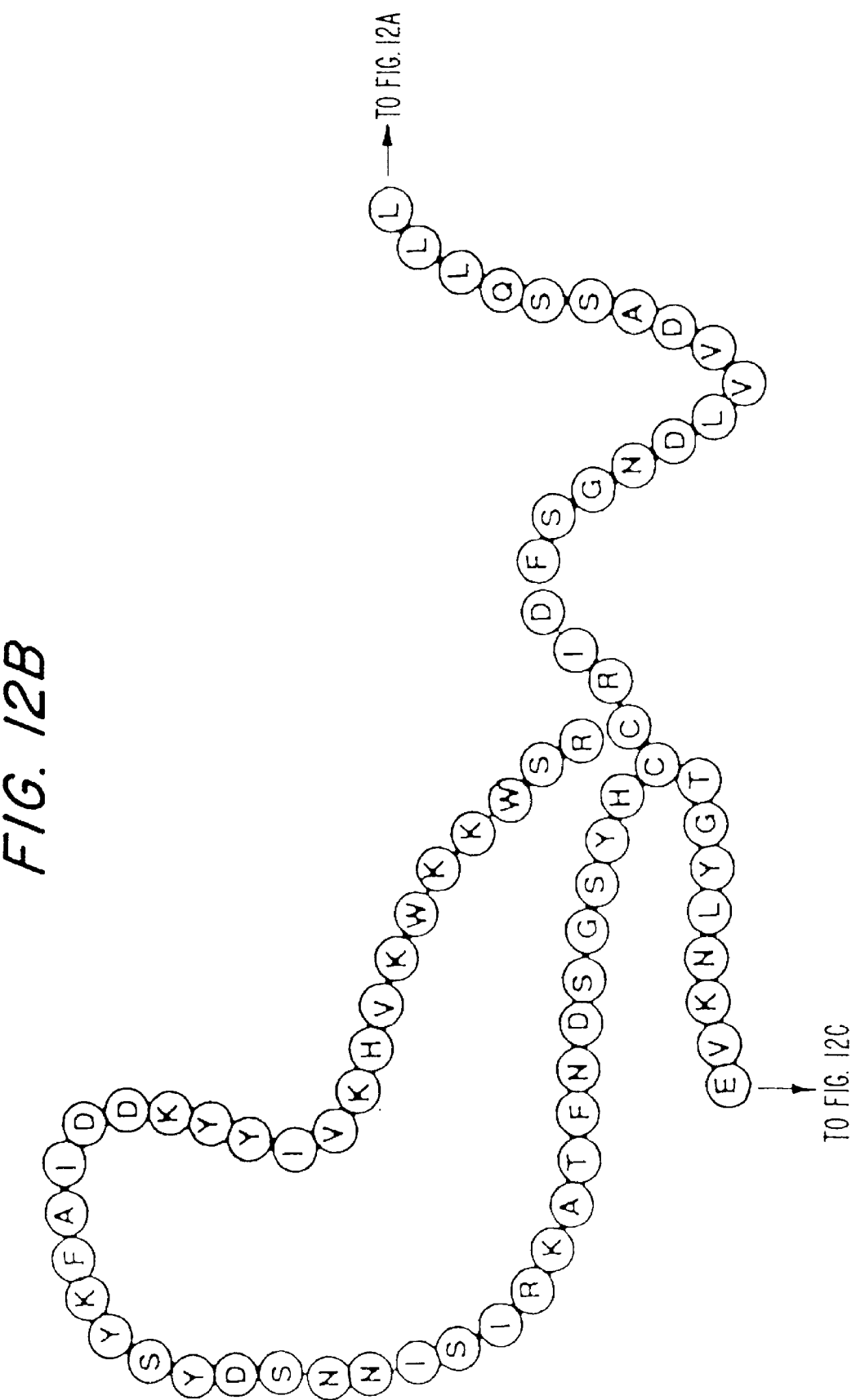
Figure 12C:
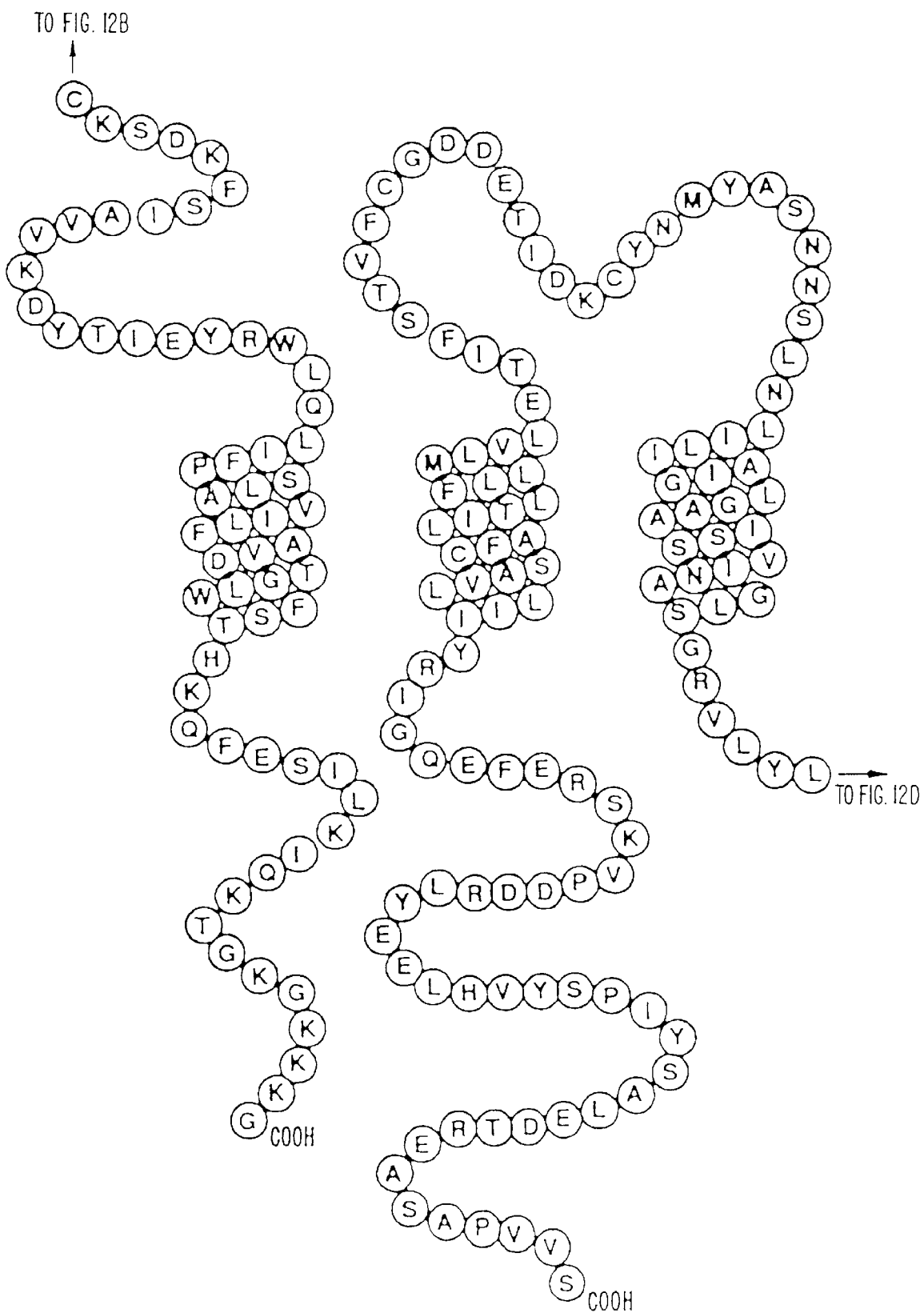
Figure 12D:
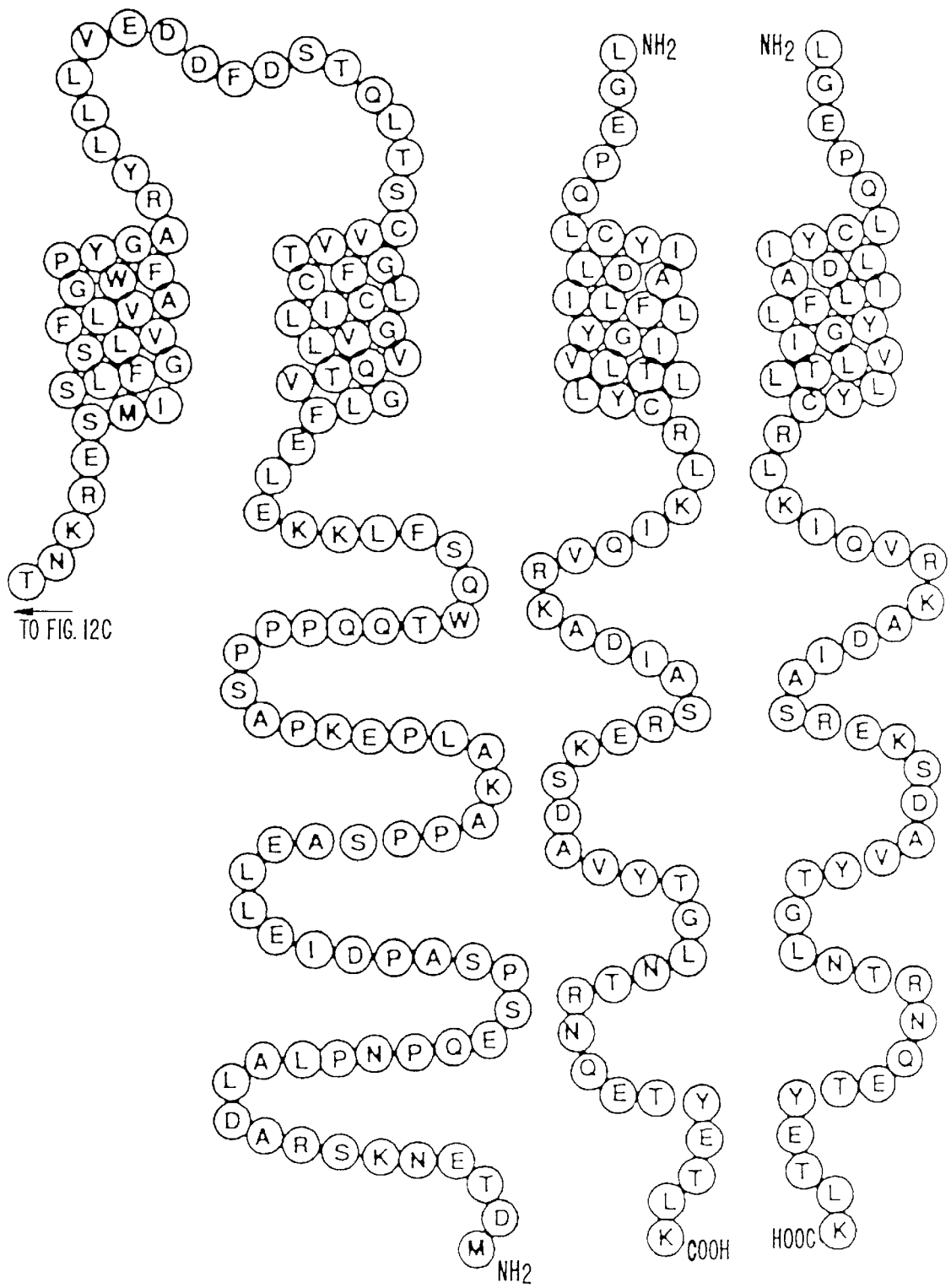

FIG. 11. Formation of IgE rosettes by transfected COS 7 cells and RBL cells. COS 7 cells were cotransfected with the coding portions of α, β and γ cDNAs and sensitized with mouse IgE anti-DNP before being exposed to red cells derivatized with TNP (Panel A). As a positive control, RBL cells were similarly tested for rosette formation (Panel C). The specificity of the resetting assay was assessed by preincubating the cotransfected COS 7 cells (Panel B) and RBL cells (Panel D) with rat IgE (which lacks the anti-DNP activity) prior to the addition of the mouse anti-DNP IgE.

FIG. 12. Model of the tetrameric high affinity receptor for IgE. The polypeptides (SEQ ID NO:28–30) are shown in their fully processed form. The receptor is oriented such that the large extracellular portion of the a subunit is shown at the top and the remainder of the chain on the left. To the right of the α subunit (SEQ ID NO:28) is the β subunit (SEQ ID NO:29) with its four transmembrane segments and to the right of it, the dimer of γ chains (SEQ ID NO:30). Cysteines 26 and 68 and cysteines 107 and 151 in the a chain are paired as they are likely to be disulfide linked, as are the homologous cysteines in the Fcγ receptors (M. Hibbs et al, J. Immunol. 140:544–550 (1988)). The putative transmembrane segments have all been shown as consisting of 21 residues and would be expected to be in an α-helical conformation. The single letter code for amino acids is used (M. Dayhoff et al, in Atlas of Protein Sequence and Structure, Suppl. 3, ed. M. Dayhoff, 363–373, Natl. Biomed. Res. Fndtn., Washington D.C. (1978)). Every 10th residue (starting from the N-terminus) is shaded.

Figure 13:
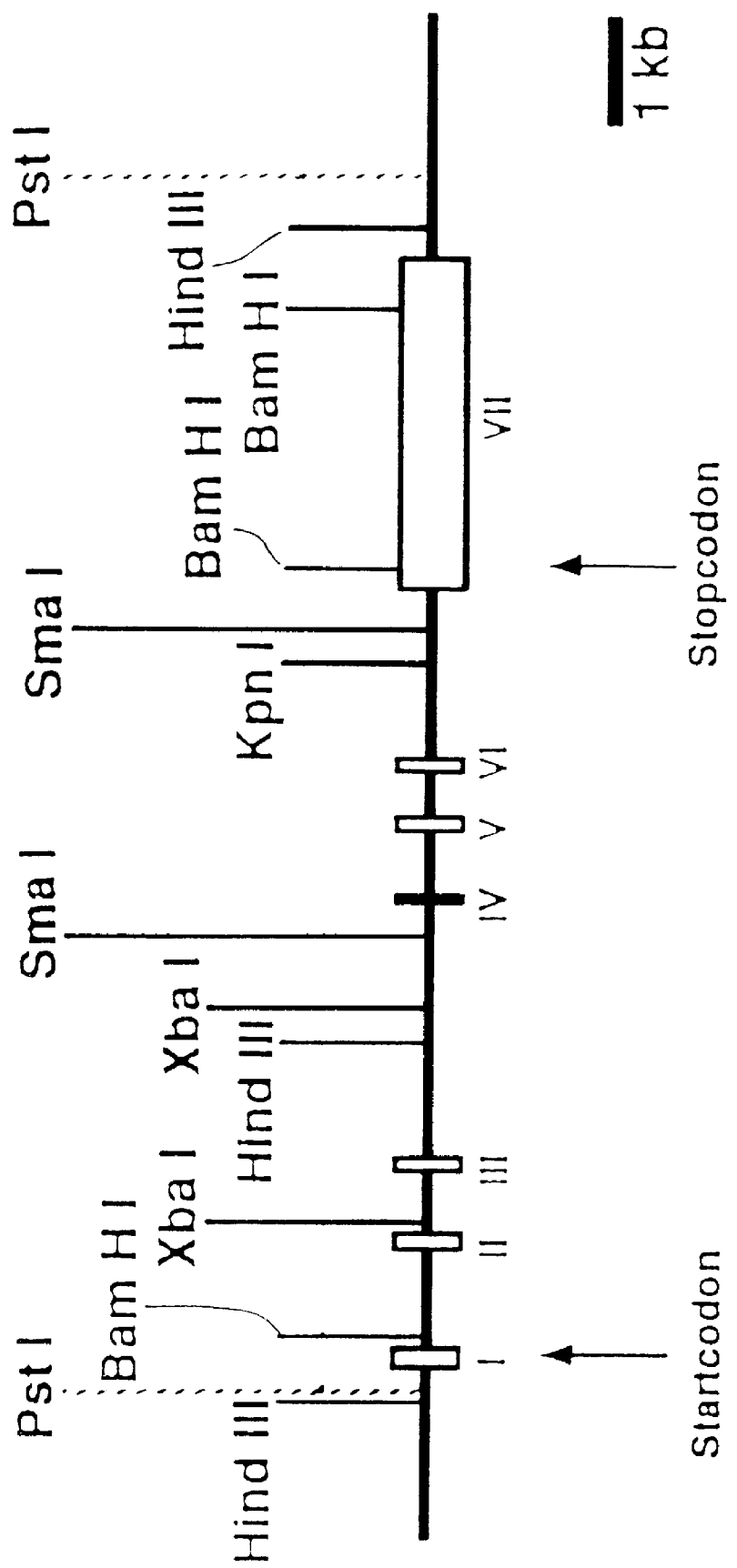

FIG. 13. Restriction map structure of a human β gene and exon-intron are shown. The positions of the 7 exons are depicted by boxes. The location of the start and stop codon is indicated.

FIG. 14A–Q. Nucleotide sequence (SEQ ID NO:31) of human FcεRI β chain gene. The 7 exons are shown in bold. The numbering of nucleotides is relative to the start codon. The TATAA box, translation initiation codon (ATG), termination codon (TAA) and the potential polyadenylation signals (AATAAA) are underlined. Bases which not determined with certainty are denoted as N.

Figure 15:
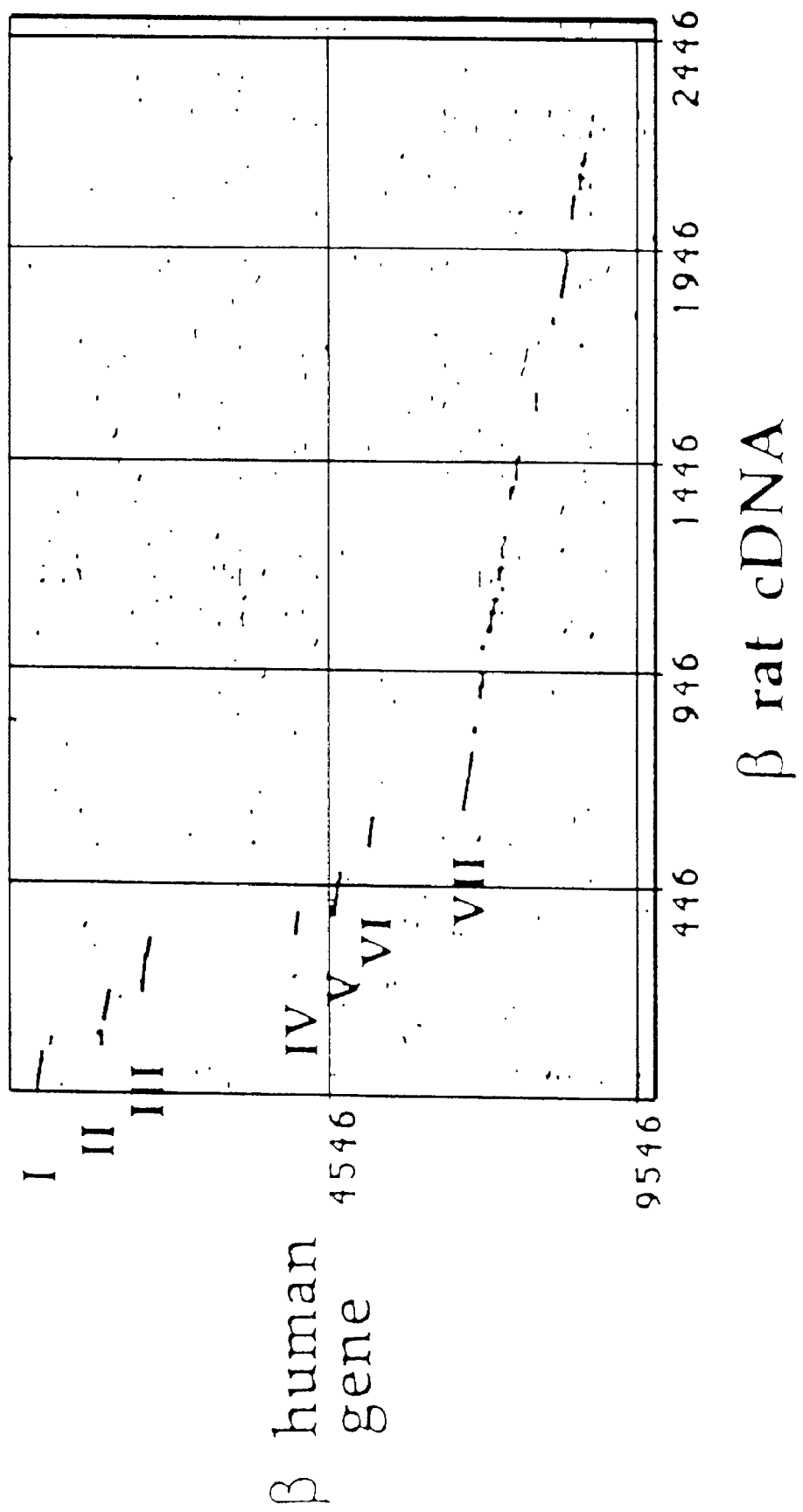

FIG. 15. Comparison of a human β gene and rat β cDNA sequences by a dot matrix blot. The Pustell DNA Matrix of the Macvector program was used with a window of 30 nucleotides and a minimum score of 63%. The Roman numerals indicated on the left correspond to the seven exons.

Figure 16A:
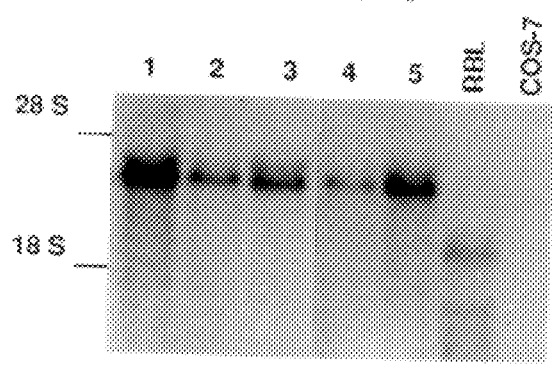

FIG. 16. Presence of transcripts in basophils are shown. Ten micrograms of total RNA from basophil enriched leukocytes and various other cells were fractionated on a denaturing agarose gel before being transferred to Nytran membranes and hybridized with human β cDNA probes (nucleotides +306 to +456 for Panel A and nucleotides −2 to +790 in Panel C). The membrane shown in Panel A was stripped and rehybridized with a full length human α cDNA probe (Panel B).

FIG. 17. Determination of the transcription initiation site. Panel A: RNA from basophils was reverse transcribed, poly A+ tailed at both ends with terminal transferase and amplified with PCR. The amplified product (cDNA) and the genomic DNA (gene) were sequenced with an identical primer and the respective sequencing reactions were run in parallel on a 8% acrylamide gel. The arrow marks the transcription start site. Panel B: RNA from basophils (lane 1) or tRNA (lane 2) were used in the primer extension and the extended products analyzed on a 5% polyacrylamide urea gel in parallel with the sequencing reactions of the genomic DNA. The arrow marks the transcription start site.

FIG. 18. Southern blot analysis of genomic DNA obtained from five different individuals. The DNAs were subjected to distinct restriction endonuclease digestions, blotted and hybridized with the human full length cDNA for the beta subunit. The numbers on the top indicate the different individuals while each panel corresponds to a different restriction digest. Size standards are indicated on the right.

FIG. 19. Amino acid sequence of the FcεRI human β subunit (SEQ ID NO:32) and alignment with rat (SEQ ID NO:33) and mouse (SEQ ID NO:34) β. Identical and non-identical amino acid residues are indicated by capital and lower case letters respectively. The identities and closely related exchanges are marked ^ in the query line while the distantly related exchanges are denoted by a dot. Non-homologous exchanges show no marking in the query line. The gaps are indicated by a hyphen. The transmembrane domains are underlined and the splice sites indicated with vertical bars.

Figure 20:
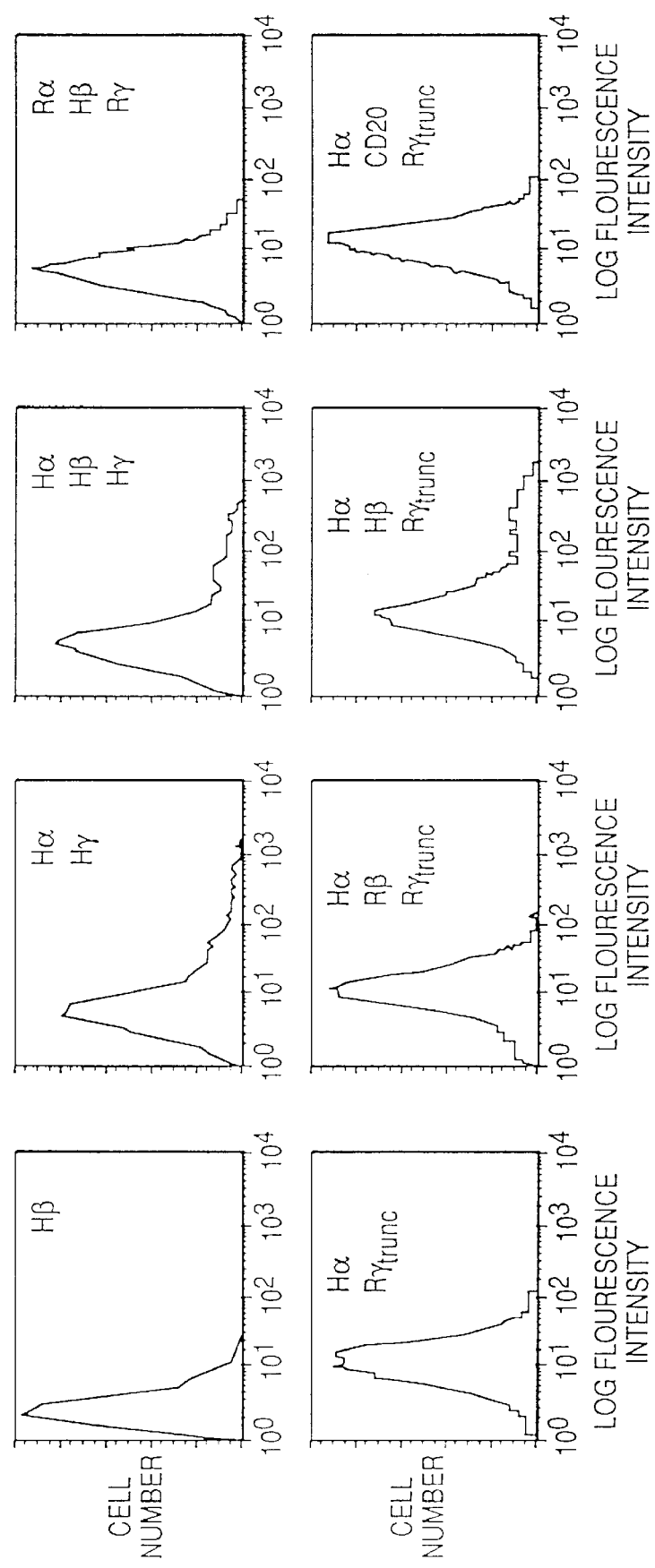

FIG. 20. Results of FACS analysis showing IgE binding in cells of a basophil line (KU812) transfected with various combinations of $Fc_\epsilon RI$ subunits.

Figure 21:
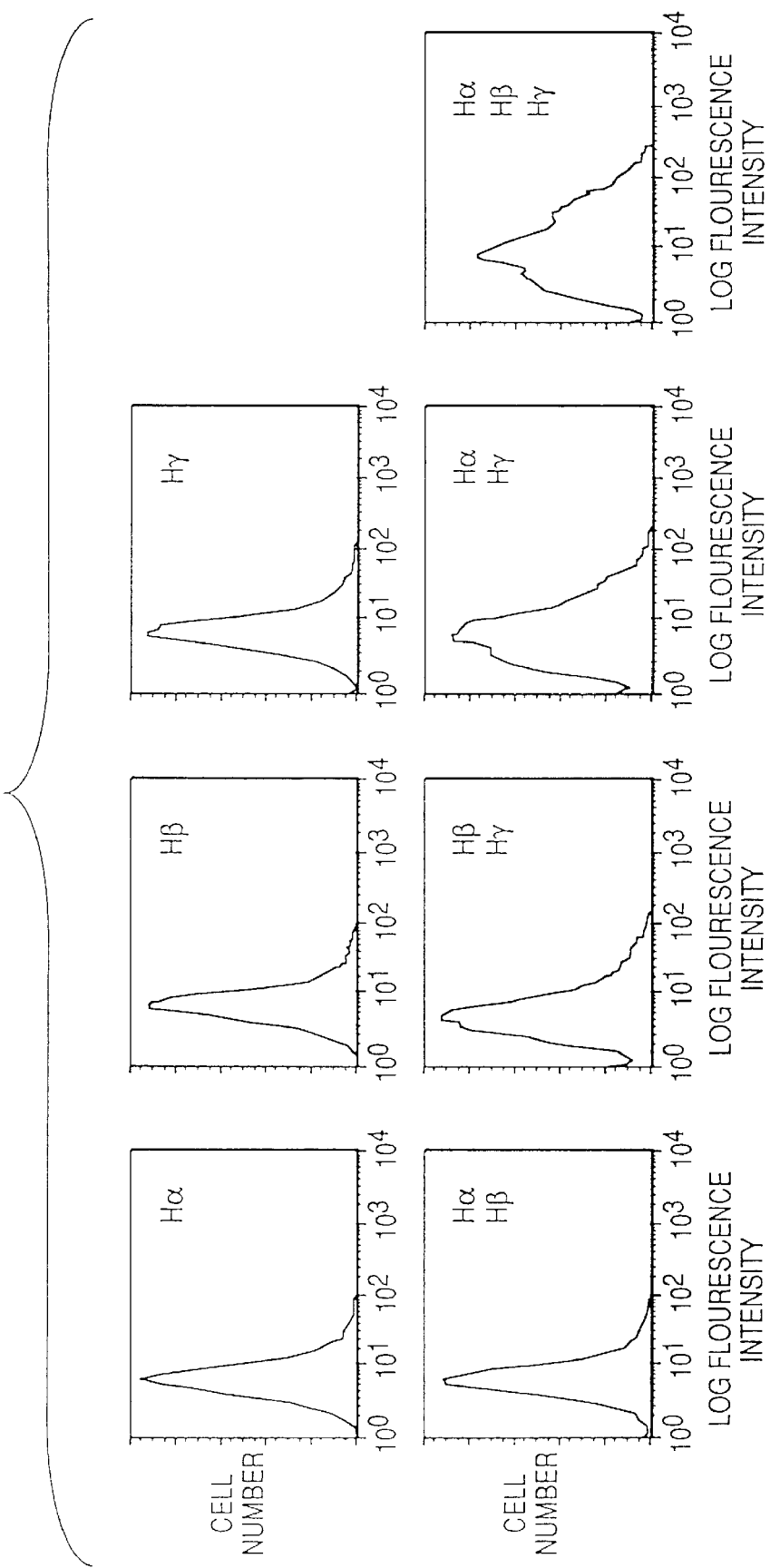

FIG. 21. Results of FACS analysis showing IgE binding in COS-7 cells transfected with various combinations of $Fc_\epsilon RI$ subunits.

DETAILED DESCRIPTION OF THE INVENTION

The present invention relates, in part, to DNA sequences which code for polypeptides corresponding to the subunits of human $Fc_\epsilon RI$.

More specifically, the present invention relates to DNA segments (for example, cDNA molecules) coding for polypeptides having amino acid sequences corresponding to the α,β and γ subunits of $Fc_\epsilon RI$. In one embodiment, the DNA segments have the sequence shown in FIG. 1, 6, 9, or 14 (SEQ ID NOS. 10, 22 and 24, 26 and 31, respectively), allelic or species variation thereof, or a unique portion of such a sequence (unique portion being defined herein as at least 15–18 bases). In another embodiment, the DNA segments encode the amino acid sequence shown in FIG. 1, 6, 9, or 19, (SEQ ID NOS. 11, 23 and 24, 27, and 32–34 respectively), or allelic or species variation thereof, or a unique portion of such a sequence (unique portion being defined herein as at least 5–6 amino acids).

Allelic or species variations are defined as substitutions, deletions, or other alterations in the nucleotide or amino acid sequence that do not eliminate the function of the subunits as defined herein. For some uses, the nucleotide sequence may be deliberately altered to, e.g., test the effects of such alteration on the function of the beta subunit, or to produce subunits which are inactiviated for certain purposes.

In another embodiment, the present invention relates to polypeptides having amino acid sequences corresponding to the α,β and γ subunits of $Fc_\epsilon RI$. In one preferred embodiment, the polypeptides have amino acid sequences as shown in FIG. 1, 6, 9, and 19 (SEQ ID NOS. 11, 23 and 24, 27, and 32–34, respectively or allelic or species variations thereof, or a unique portion of such sequences (unique portion being defined herein as at least 5–6 amino acids).

In another embodiment, the present invention relates to a recombinant DNA molecule comprising a vector (for example-plasmid or viral vector) and a DNA segment coding for a polypeptide corresponding to the α,β or γ subunit of $Fc_\epsilon RI$, as described above. In a preferred embodiment, the encoding segment is present in the vector operably linked to a promoter.

In a further embodiment, the present invention relates to a cell containing the above described recombinant DNA molecule. Suitable host cells include procaryotes (such as bacteria, including *E coli*) and both lower eucaryotes (for example yeast) and higher eucaryotes (for example, mammalian cells). Introduction of the recombinant molecule into the host cell can be effected using methods known in the art.

In another embodiment, the present invention relates to a method of producing the above described polypeptides, comprising culturing the above described host cells under conditions such that said polypeptide is produced, and isolating said polypeptide.

In a further embodiment, the present invention relates to a method of producing a functional $Fc_\epsilon RI$ receptor comprising introducing into a host cell DNA segments encoding the α,β and γ subunits of $Fc_\epsilon RI$ and effecting expression of said segments under conditions such that said receptor is formed.

The nucleic acid sequences and polypeptides according to this invention exhibit a number of utilities including but not limited to:

1. Utilizing the polypeptide or a fragment thereof as an antagonist to prevent allergic response, or as a reagent in a drug screening assay.
2. Utilizing the polypeptide as a therapeutic agent.
3. Utilizing the polypeptide for monitoring IgE levels in patients.
4. Utilizing the nucleic acid sequence to synthesize polypeptides which will be used for the above purposes.
5. Utilizing the nucleic acid sequences to synthesize cDNA sequences to construct DNA useful in diagnostic assays.

The present invention will be illustrated in further detail in the following examples. These examples are included for illustrative purposes and should not be considered to limit the present invention.

EXAMPLE 1

Isolation of cDNA Clones for the Alpha Subunit of Human $Fc_\epsilon RI$

RNA was extracted from FUB12 cells as described by Kishi, *Leukemia Research*. 9,381 (1985) by the guanidium isothiocyanate procedure of Chirgwin, et al., *Biochemistry*, 18,5294 (1979) and poly(A) mRNA was isolated by oligo-dt chromatography according to the methods of Aviv, et al., *P.N.A.S. U.S.A.*, 69,1408 (1972). cDNA synthesis was performed as previously described Kinet, et al, *Biochemistry*. 26,2569 (1987). The resulting cDNA molecules were ligated to EcoRI linkers, digested with the restriction enzyme EcoRI, size fractioned and ligated to λgt11 EcoRI arms as set forth in Young et al, *Science*. 222.778 (1983). The cDNA insert containing λgt11 DNA was packaged into bacteriophage lambda particles and amplified on Y1090. A total of 1.2×106 independent cDNA clones were obtained. The cDNA library was plated onto Y1090 on 150 mm$_2$ plates (10$^5$ per plate) and transferred to nitrocellulase filters. The cDNA library filters were screened by in situ hybridization using a nick translated cDNA fragment as in Kochan, et al, *Cell*, 44,689 (1986). The cDNA fragment was obtained from the rat $Fc_{\epsilon RI\ alpha\ cDNA\ corresponding\ to\ nucleotides}$ 119–781. Positive plaques were identified, purified and the cDNA inserts were subcloned, using standard techniques, into the pGEM vectors (Promega Biotech, Madison, Wis.). The cDNA insert was mapped by restriction enzyme analysis, subcloned into derivatives of pGEM and sequenced using the dideoxynucleotide method of Sanger et al., *P.N.A.S.* 74,5463 (1977) following the GemSeq double strand DNA sequencing system protocol from Promega Biotech (Madison, Wis.). The DNA sequence was determined for both strands of the cDNA clone pLJ663 (nucleotides 1–1151) and for 300 bp of each end of clone pLJ 587 (nucleotides 658–1198). No discrepancy in DNA sequence between the two cDNA clones was observed.

The sequence for the human $Fc_\epsilon RI$ alpha cDNA is presented in FIG. 1 SEQ ID NO:10. The predicted amino acid sequence for the human $Fc_\epsilon RI$ alpha polypeptide is shown below the nucleotide sequence and in SEQ ID NO:11, beginning with methionine at nucleotide 107–109 and ending with asparagine at nucleotide 875–877. The site of the predicted mature N-terminus was determined to be valine at nucleotide 182–184 according to the rules set forth by von Heijne, *Eur. Journal of Biochem:* 137.17; and *Nucleic Acid Research,* 14,4683 (1986).

Figure 2:
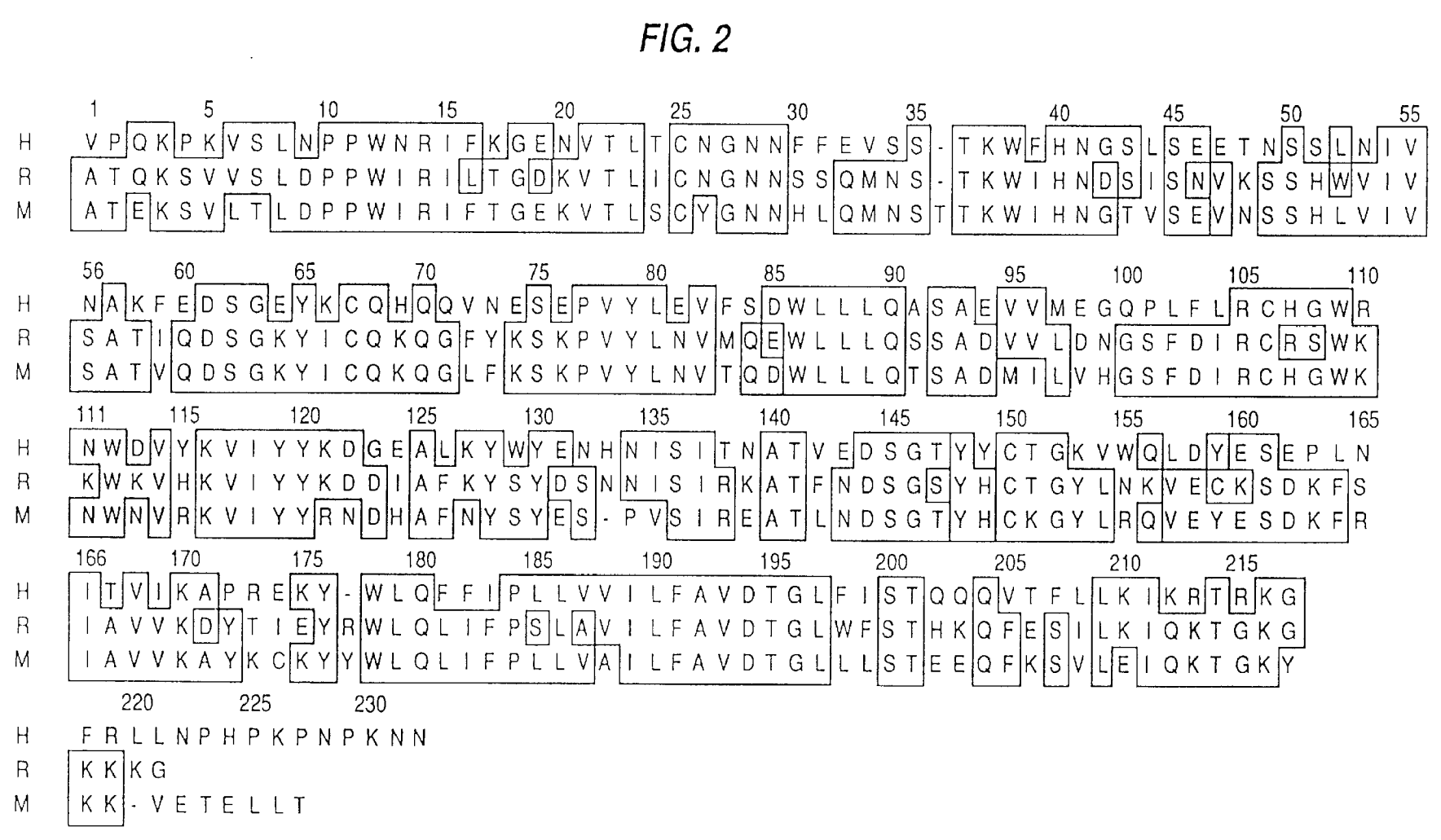

These results predict a 25 amino acid signal peptide. The rest of the cDNA sequence suggests that the human $Fc_\epsilon RI$ alpha chain contains about 179–224 residues with 2 homologous domains (14 out of 25 residues are identical; residues 80–104 and 163–190), a 20-residue transmembrane segment (residues 205–224) and a 33 residue cytoplasmic domain containing 8 basic amino acids. Overall, there is 47% identity between the human and rat $Fc_\epsilon RI$ alpha sequences, and 46% identity between the human FRI alpha and mouse FcGR alpha (FIG. 2). SEQ ID NOS. 12–14. The greatest level of homology is within the transmembrane region where 9 amino acids surrounding the common aspartic acid residue are identical.

EXAMPLE 2

Expression of the Human $Fc_\epsilon RI$ Alpha Complete and Soluble Forms in Eukarvotic Cells Using the recombinant cDNA clone for the human $FC_\epsilon RI$ alpha chain, it is possible to introduce these coding sequences into an appropriate eukaryotic expression vector to direct the synthesis of large amounts of both a complete and soluble form of the alpha chain. For surface expression it may necessary that the alpha subunit be complexed with the beta or gamma subunit whereas for the eukaryotic expression of the secreted form of the alpha subunit this may not necessary. An appropriate vector for the purpose is pBC12BI which has previously been described in Cullen, (1987) *Methods in Enzymology* 152. Academic Press, 684. Construction of expression vectors coding for the complete alpha chain can be isolated as follows (FIG. 3): A unique BqlII-SspI fragment (nucleotides 65–898) is isolated from pLJ663, the BglII end is filled in with DNA polymerase I Klenow fragment and ligated into pBC 2BI which has been restricted with either HindIII-BamHI or HindIII-SmaI (the ends are made blunt by filling in with DNA polymerase I Klenow fragment). The reason for attempting two different constructions is that the former contains a 3' intron while the latter does not. The presence or absence of introns may affect the levels of the alpha protein which are synthesized in cells transfected by these vectors. Construction of expression vectors coding for the soluble form of the alpha chain would be accomplished by introducing a termination codon at nucleotides 719–721 of the coding region in the alpha chain of the expression vectors noted above (pHAI, pHAII, FIG. 3). This would remove the putative transmembrane and cytoplasmic regions resulting in the synthesis of a secreted soluble form of the human alpha chain. Introduction of a termination codon is accomplished by oligonucleotide-directed site specific mutagenesis as outlined by Morinaga et al., *Bio. Tech.,* 2, 636 (1984). The sequence of the oligo-nucleotide will be 5' AAGTACTGGCTATGATTTTTATC-CCATTG 3' (SEQ ID NO:1). The resulting expression vectors are pHASI and pHASII (FIG. 3) and these will direct the synthesis of a truncated alpha protein corresponding to amino acids 1–204. Expression of this protein in eukaryotic cells will result in synthesis of a mature, IgE binding protein encompassing amino acid residues 26–204.

The expression vectors are then introduced into suitable eukaryotic cells such as CHO or COS by standard techniques such as those set forth in Cullen, (1987), *Methods in Enzymology*. Academic Press, NY 152:684, in the presence of a selectable marker such as G418 or Methotrexate resistance. The selectable marker for Methotrexate resistance has an added advantage, since the levels of expression can be amplified by introducing the cells to higher levels of drugs. The synthesis of protein is monitored by demonstrating the ability of human IgE (or rat IgE) to bind to these cells (in the case of the complete alpha chain), or in the case of the soluble form of the alpha chain, to demonstrate that the protein secreted from these cells has the ability to bind IgE in the presence or absence of the beta.

EXAMPLE 3

Figure 4:
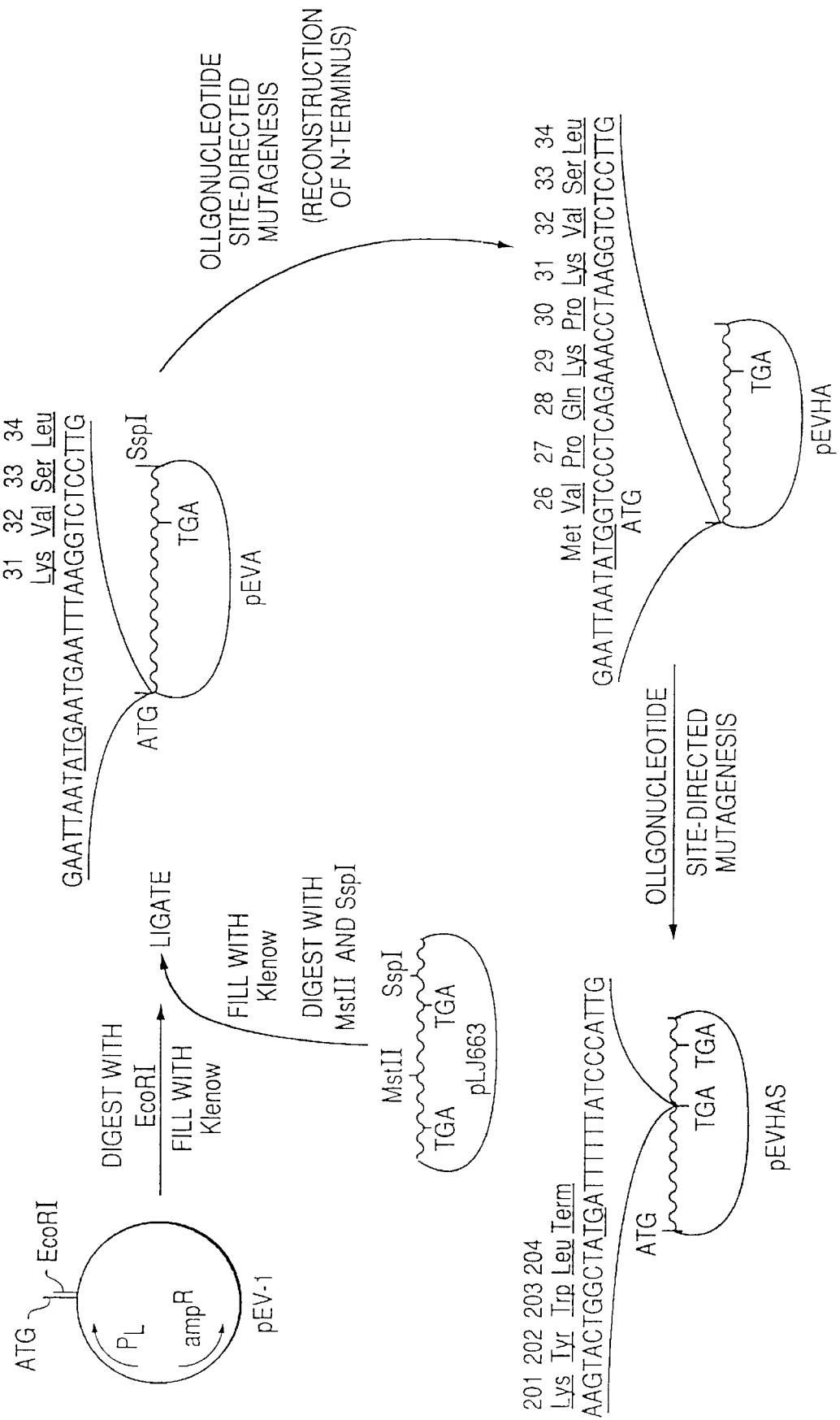
FIG. 4. A flow chart showing the construction of a prokaryotic expression vector which directs the synthesis of a soluble biologically active $Fc_\epsilon RI$ alpha chain (which consists of amino acid residues 26-204) is presented.

Expression of the Human $Fc_\epsilon RI$ Alpha Soluble Form in Prokarvotic Cells Using the recombinant cDNA clone for the human $Fc_\epsilon RI$ alpha chain, it is possible to introduce these coding sequences into an appropriate prokaryotic expression vector to direct the synthesis of large amounts of a soluble (non-membrane bound) IgE binding polypeptide derived from the alpha chain. An appropriate vector for this purpose is pEV-1 which has been described by Crowl, et al, *Gene.* 38, 31 (1985). Construction of an expression vector coding for a soluble alpha chain can be isolated as set forth in FIG. 4: a unique MstlI-SspI fragment (nucleotides 195–898 is isolated from pLJ663, the MstII end is filled in with DNA polymerase I Klenow fragment and ligated into pEV-1 which has been restricted with EcoRI, and the ends filled in with Klenow (FIG. 4, pEVA). The N-terminus of the mature alpha chain is reconstructed by oligonucleotide directed-site specific mutagenesis. The sequence of the oligonucleotide will be 5' GAATTAATATGGTCCCTCAGAAAC-CTAAGGTCTCCTTG 3' (SEQ ID NO:2). Introduction of this sequence into the expression vector pEVA aligns the Methionine residue of the EV-1 vector next to Valine-26 (the predicted mature N-terminus of the alpha chain) followed by amino acid residues 27–204 (pEVHA, FIG. 4). Reconstruction of the soluble form $FC_\epsilon RI$ alpha is accomplished by oligonucleotide site-directed mutagenesis. The sequence of the oligonucleotide will be 5'- AAGTACTGGCTAT-GATTTTTTATCCCATTG - 3' (SEQ ID NO:3). Introduction of this sequence into the expression vector, terminates polypeptide synthesis just prior to the start of the transmembrane region. The protein thus encoded by expression vector pEVHAS, should faithfully direct the synthesis of a soluble form of the alpha chain, corresponding to amino acid residues 26–204. This expression vector is then transformed into suitable hosts.

EXAMPLE 4

Isolation and Sequence Analysis of Peptides of the Beta Subunit of $Fc_\epsilon RI$ Since repeated attempts to sequence intact β chains were unsuccessful, peptides were isolated from tryptic digests. Electroeluted β subunits from polyacrylamide gels were prepared as described (Alcaraz et al. (1987) *Biochemistry* 26:2569–2575). Tryptic peptides were separated by highpressure liquid chromatography and sequenced as before (Kinet et al. (1987) Biochemistry 26:4605–4610). A peptide (no. 1) isolated from an initial digest had the sequence (SEQ ID NO:4) Tyr-Glu-Glu-Leu-His-Val-Tyr-Ser-Pro-Ile-Tyr-Ser-Ala-Leu-Glu-Asp-Thr. The same peptide from later digests showed an additional leucine at the NH₂ terminus and an arginine at the COOH terminus. The sequences of three other peptides, each isolated in substantial yields, are indicated in a subsequent figure.

EXAMPLE 5

Cloning and Sequencing of cDNA clones of the Beta Subunit of Fe$_c$RI

Figure 5:
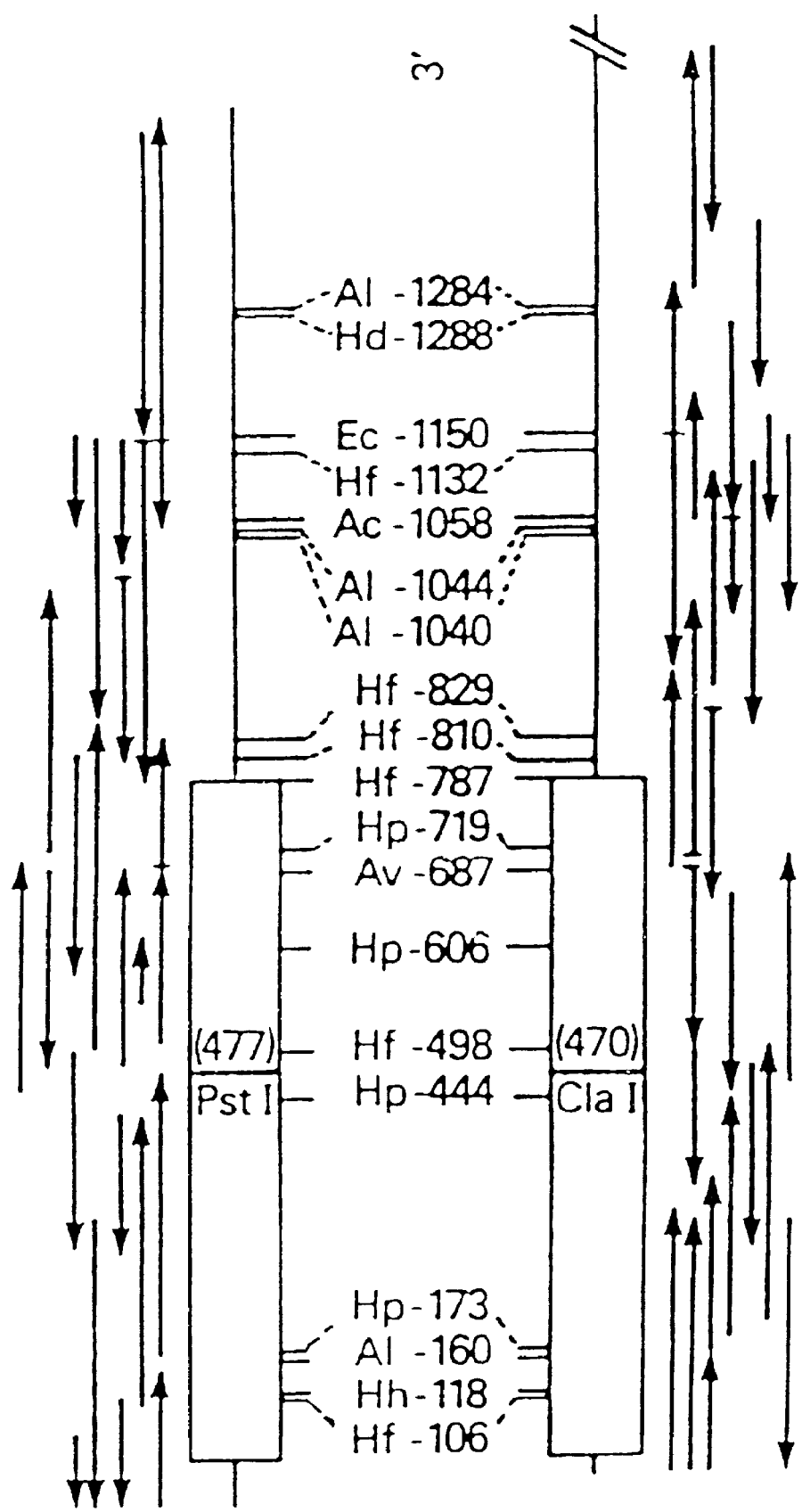
FIG. 5. Restriction maps for β cDNAs and strategy by which they were sequenced. The open rectangle indicates the sequence predicted to code for the β subunit; the lines indicate the 5' and 3' untranslated regions. The upper scheme shows the 1.5 kilobase (kb) clone containing a Pst I cleavage site. The lower scheme shows a 2.4-kb clone containing a ClaI cleavage site. The 3' region of the latter has been truncated as indicated by the slashes. Its untranslated portion was sequenced as completely as the rest of the clone. Restriction sites are indicated by vertical bars: Hf, Hinfl; Hh, Hha I; Al, Alu I; Hp, HphI; Av, Ava II; Ac, Acc I; Ec, EcoRI; Hd, HindIII. The horizontal arrows show the direction and extent of sequencing by the dideoxynucleotide chain-termination method.

RNA extracted from rat basophilic leukemia (RBL) cells by the guanidinium isothiocyanate method (Chirgwin et al. (1979) Biochemistry 18:5294–5299) was fractionated on an oligo(dT)- cellulose column (Maniatis et al. (1982) Molecular Cloning: A Laboratory Manual (Cold Spring Harbor Lab., Cold Spring Harbor, N.Y.) and used to construct a pUC-9 and a λgtll library (Maniatis et al. (1982) Molecular Cloning: A Laboratory Manual (Cold Spring Harbor Lab., Cold Spring Harbor, N.Y.; Young and Davies (1983) Proc. Natl. Acad. Sci. U.S.A. 80:1194–1198). The initial sequence obtained for peptide 1 was used to construct two 26-mer oligonucleotides of 32-fold degeneracy: 5'-GGIGA(A/G)TA(G/C) ACATGIA(A/G) (C/T) TC (C/T) TCATA-3' (SEQ ID NO:5) and 5'-GGICT(A/G)TA(G/C)ACATGIA(A/G)(C/T)TC(C/T)TCATA 3' (SEQ ID NO:6). A λgtll library constructed from mRNA of RBL cells was screened with 1:1 mixture of these 15 oligonucleotides. Colonies were screened as in Kinet et al. (1987) Biochemistry 26:4605–4610, using oligonucleotides prepared on a model 380A automated DNA synthesizer (Applied Biosystems, Foster City, Calif.). Six positive clones gave similar restriction patterns. cDNA inserts were subcloned into pGEM-4 or pGEM-3Z and the resulting double-stranded DNA was sequenced with the GemseqRT sequencing system according to the method recommended by the supplier (Promega Biotec, Madison, Wis.). Twenty-mer oligonucleotides, corresponding to previously sequenced regions by this method, were used as primers to generate overlapping sequences otherwise difficult to obtain. In some instances, DNA sequencing was performed using Sequenase as recommended by the supplier (United States Biochemical, Cleveland). The clone containing the longest insert was sequenced according to the strategy shown in the upper portion of FIG. 5. The sequence predicts possible starting codons at nucleotides 46–48 and 55–57, which would yield a polypeptide of 246 or 243 residues, respectively (FIG. 6A and SEQ ID NO:22). The predicted $M_r$ of about 27,000 is some 20% less than the apparent molecular weight of β subunits when analyzed on polyacrylamide gels (Holowka and Metzger (1982) Mol. Immunol. 19:219–227). In addition, no in-frame stop codon was apparent upstream of the start codon. To rule out the possibility that the true start codon was still further 5', the cDNA library was rescreened with a restriction fragment (nucleotides 7–474) and with a synthetic oligonucleotide probe (nucleotides 3–32). Twenty-eight additional clones were isolated and their restriction patterns were examined. Twenty were similar to the original clones. Only six additional nucleotides at the 5' end (nucleotides 1–6, FIG. 6A(1) were identified. Early termination was found in six clones, which otherwise had the same sequence through nucleotide 375 (FIG. 6B and SEQ ID NO:24). One 2.4-kb clone had cytidine 473 substituted with an adenine. This substitution abolishes the Pst I site and creates a new Cla I site at nucleotide 470. Also thereby, Ala-140 would become Asp-140 (FIG. 6A).

Finally, one clone extended ≈350 base pairs (bp) in the 5' direction. The junction with the sequence shown in FIG. 6A(1)–(6) was (SEQ ID NO:7) AATAAAACAAAAAAAAAAAAATG, the last two nucleotides of the newly generated ATG corresponding to nucleotides 8 and 9 of the previous sequence. It is likely that this clone simply resulted from the ligation of two independent cDNAs. Screening of the pUC-9 library revealed three clones. However, the sequence of none of these extended 5' beyond nucleotide 84.

EXAMPLE 6

RNA Transfer Blotting

RNA transfer blotting was performed under high stringency using a Pst I fragment probe (nucleotides 1–474). Thirty micrograms of total RNA was run on a 1% agarose gel containing 2% formaldehyde and blotted to nitrocellulose filters (Maniatis et al. (1982) Molecular Cloning: A Laboratory Manual (Cold Spring Harbor Lab., Cold Spring Harbor, N.Y.). The filters were hybridized with a restriction fragment of the β cDNA (nucleotides 1–474) as described (Maniatis et al. (1982) Molecular Cloning: A Laboratory Manual (Cold Spring Harbor Lab., Cold Spring Harbor, N.Y.) and washed with 15 mM NaCl/1.5 mM sodium citrate at 65° C. RBL cells yielded two major bands at ≈2.7kb and 1.75kb with the upper band having about twice the intensity of the lower one. A minor band 1.2kb was also noted. Negative results were obtained with a variety of cells that do not express high-affinity IgE receptors: the rat pituitary line GH3 (American Type Culture Collection no. CCL82.1), the rat glial cell line C6 (no. CCL107), the mouse Leydig cell line 1–10 (no. CCL83), and, notably, the mouse monocytic line J774 (no. T1B67) and the rat lymphoma "NTD" (Rivera et al. (1988) Mol. Immunol.)

EXAMPLE 7

In vitro transcriDtion and translation cDNAs corresponding to the β subunit and various mutated or truncated forms thereof were subcloned into either pGEM-4 or pGEM-3Z transcript ion vectors (Promega Biotec). The β clone containing the Pst I site was transcribed in vitro with T7 RNA polymerase. Unlabeled RNAs were synthesized using either SP6 or T7 polymerase as recommended by the supplier. Capping reactions were performed as reported (Contreras et al. (1982) Nucleic Acids Res. 10: 6353–6362). After digestion of the template with RNase-free DNase I, the RNAs were purified further by extraction with phenol/chloroform and three precipitations from ethanol. The RNA was then translated with a micrococcal nuclease-treated lysate of rabbit reticulocytes in the presence of [S³⁵] methionine as recommended by the supplier (Promega Biotec). The products of translation were diluted 1:1 with 20 mM detergent {3-[3-(cholamidopropyl) dimethylammonio)-1-propane sulfonate in borate-buffered saline (pH 8) containing 30 μl of aprotinin per ml, 175 μg of phenylmethyl-sulfonyl fluoride per ml, 10 μg of leupeptin per ml, and 5 μg of pepstatin per ml and immunoprecipitated with monoclonal antibodies as described (Rivera e al. (1988) Mol. Immunol.). The unfractionated translated material showed a major component at $M_r$ 32,000 compared to the control from which the RNA had been omitted or an alternative RNA (brome mosaic virus) had been substituted.

The isolation of antibodies was as follows: *Escherichia coli* transformed with an expression vector containing the desired restriction fragments (Crowl et al. (1985) Gene 38:31–38; Portnoy et al. (1986) J. Biol. Chem. 261:14697–14703) were cultured and induced, and the fraction enriched for the recombinant protein was prepared as described (Portnoy et al. (1986) J. Biol. Chem. 261:

14697–14703). After separation on polyacrylamide gels in sodium dodecyl sulfate (NaDodSO$_4$) the transformant-specific protein was eluted and used to immunize rabbits. Approximately 100 μg of protein was injected in complete Freund's adjuvant; this was followed by a booster injection of 25 μg of protein in incomplete adjuvant. The isolation and characterization of monoclonal anti-β antibodies mAbβ (JRX) and mAbβ(NB) (the latter, was obtained from David Halowka, Cornell University) have been described (Rivera et al. (1988) Mol. Immunol. 25:647–661).

Figure 7A:
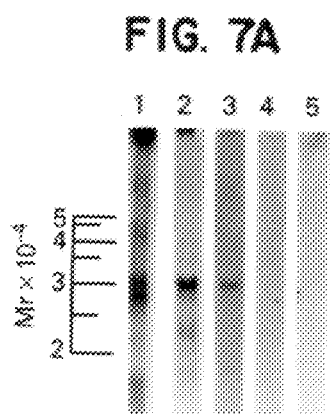
FIG. 7. Expression of cDNA coding for the β subunit. (A) Comparison of in vivo and in vitro translation products. RBL cells were grown in [$^{35}$S]cysteine containing medium. The detergent extract of the cells was precipitated with mAbβ(JRK) and, after vigorous washing, extracted with sample buffer and electrophoresed (lane 1). This experiment employed concentrations of detergent high enough to dissociate the receptor completely. A transcript from the β cDNA was treated in vitro in [$^{35}$S]methionine-containing medium (lanes 2, 3, and 5).
Figure 7B:
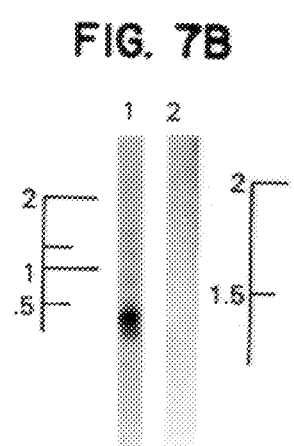

The monoclonal anti-β antibodies mAbβ(JRk) and mAbB (NB) (Rivera et al. (1988) Mol. Immunol.) (FIG. 7A, lanes 2 and 3) - but not an irrelevant antibody (lane 5)-precipitated radioactive material, which on polyacrylamide gels in NaDodSO$_4$ showed a major band at M$_4$ 32000. This band had the identical mobility as the upper band of the doublet precipitated by mAbβ(JRK) from an extract of labeled RBL cells (lane 1). Although not seen well in the reproduction, the autoradiogram showed that the material synthesized in vitro also contained the lower molecular weight component seen the in vivo synthesized 0 chains. The mobility of the in vitro synthesized protein was unaltered by reduction as has been previously observed with the β subunit. The clone containing the Cla I site (which lacks the first ATG codon) led to the synthesis of a protein whose mobility on gels was indistinguishable from that for the clone containing the Pst I site. On the other hand, an aberrant clone containing the newly generated ATG (above) induced the synthesis of a somewhat larger protein with an apparent M$_r$, of 33,500. In vitro translation of a transcript coding for the NH$_2$-terminal 21 amino acids of the β subunit led to a product precipitable by mAbβ(JRK) (FIG. 7B).

EXAMPLE 8

Expression of the Beta Subunit of Fc$_\epsilon$RI in *E. coli*

Figure 7C:
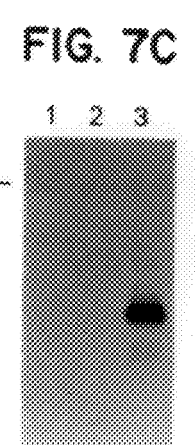
Figure 7D:
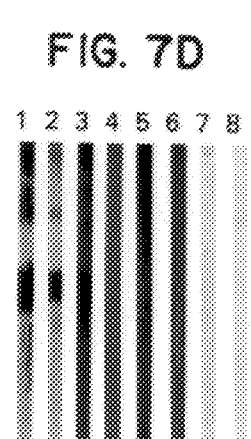

Two HinfI fragments (A, nucleotides 106–498; B, nucleotides 499–787) were individually subcloned into an *E. coli* expression vector, and extracts were prepared from the induced cultures. The results of one immunoblotting experiment are shown in FIG. 7C. The material extracted from the bacteria transformed with a vector containing the HinfI fragment B exhibited a M$_r$ 14,000 component reactive with mAbβ(NB) but not with mAbB(JRK) (FIG. 7C, lane 3). The extract from the transformants containing the more NH$_2$-terminal HinfI fragment A (residues 17–148) reacted with neither antibody (compare with above). Rabbit antibodies generated by fragment A reacted on immunoblots with purified receptors exactly at the position where the two monoclonal anti-β antibodies reacted (FIG. 7D, lanes 1–3) and quantitatively precipitated intact $^{125}$-labeled IgE-receptor complex from unfractionated detergent extracts of RBL cells.

EXAMPLE 9

Biosynthetic Incorporation

Biosynthetic incorporation of labeled amino acids and monosaccharides was as described (Perez-Montfort et al. (1983) Biochemistry 27:5722–5728). The purification and analysis on gels and by immunoblotting of the IgE-receptor complexes have also been described (Rivera et al. (1988) Mol. Immunol.).

By using biosynthetic incorporation of two different amino acids labeled distinguishably, their ratio in the subunits of the receptor (Table 1, right part) was determined. The ratios of four distinctive amino acids to each other was in satisfactory agreement with the ratios predicted from the β cDNA clone (Table 1, right part, columns 1–3). Because the cDNA for the β subunit predicts three potential glycosylation sites, a double-labelling experiment using ($^3$H] mannose and ($^{35}$S) cysteine was also performed. Based on the relative carbohydrate data reported for the α subunit (Kaneilopoulos et al. (1980) J. Biol. Chem. 255:9060–9066) and correcting them on the basis of the peptide molecular weight for this chain predicted from the cDNA, it was calculated that the α subunit contains ≈20 mol of mannose per mol. It was therefore possible to determine the mannose/cysteine ratio in the β subunit from the double-labeling experiment. The results showed only 0.05 mol/mol of cysteine or 0.3 mol/mol of the β subunit (Table 1, right part, column 4).

TABLE I

Amino Acid composition of β Subunits cDNA versus compositional analysis for the β subunit

| | Asx | Thr | Ser | Glx | Pro | Gly | Ala | Val | Met | Ile | Leu | Tyr | Phe | His | Lys | Arg | Cys | Trp |
|---|---|---|---|---|---|---|---|---|---|---|---|---|---|---|---|---|---|---|
| Deduced from β cDNA | 20 | 12 | 23 | 24 | 15 | 12 | 19 | 17 | 4 | 15 | 36 | 9 | 12 | 1 | 8 | 8 | 6 | 2 |
| Direct analysis* Double-labeling studies+ | 22 | 13 | 22 | 27 | 13 | 19 | 18 | 14 | 4 | 13 | 31 | 7 | 10 | 2 | 10 | 10 | 5 | ND | cDNA versus incorporation data

| | Met/His | Cys/His | Cys/Trp | Man/Cys |
|---|---|---|---|---|
| Deduced from β cDNA | 4 | 6 | 3 | — |
| Direct analysis* | | | | |
| Double-labeling studies+ | 4.2 | 5.1 | 2.5 | 0.05 |

*The mol % of each amino acid as reported by Alcaraz et al. ((1987) Biochemistry 26:2569–2575) was multiplied by 241 - the number of residues, excluding tryptophan - predicted from the cDNA. ND, not determined.
+IgE-receptor complexes were purified from RBL cells incubated with a mixture of two precursors labeled with differentiable radioisotopes. The subunits were separated on a polyacrylamide gel. The gel was sectioned into 2 mm slices, extracted, and assayed for radioactivity by scintillation spectroscopy. The ratio of cpm of $^{35}$S/$^3$H was individually calculated for α, β, and γ subunits. The ratio in the α, subunit is proportional to the known molar ratio of the $^{35}$S-labeled and $^3$H-labeled residues in the α subunit. Hence, the corresponding ratio in the β subunit (and the γ subunit) predicts the ratio of the same residues in the latter subunits.

EXAMPLE 10

Sequence Characteristics

There is ample evidence that the cDNAs that were isolated code for the β subunit. (i) In vitro transcription of the cDNA and translation of the derived MRNA produce a protein whose apparent molecular weight on gel electrophoresis is indistinguishable from that of authentic β chains (FIG. 7A). (ii) The cDNA accurately predicts the sequence of four peptides isolated from a tryptic digest of β chains (FIG. 6A and SEQ ID NO:22) and a composition that agrees well with direct analyses and biosynthetic incorporations (Table I). (iii) Two monoclonal antibodies reactive with discrete epitopes on the β subunit (Rivera et al. (1988) Mol. Immunol.) precipitate the protein synthesized in vitro from the cloned cDNA (FIG. 7A), and one of them reacts with a fragment of the protein expressed in E. coli (FIG. 7C). (iv) Polyclonal antibodies raised against a fragment of the β subunit synthesized by E. coli transformants react with β chains on immunoblots (FIG. 7D) and with IgE-receptor complex in solution.

The nucleotide sequence at the 5' end of the cloned CDNA (clone 1) does not in itself define the start of the open reading frame unambiguously. There is no leader sequence and no "in frame" stop codon preceding the presumptive start codon. In addition, the molecular weight deducted from the cDNA ($M_r$~27,000) is substantially lower than the one observed on $NaDodSO_4$ gels ($M_r$~32,000), although the β subunit is not glycosylated. Therefore, it was possible that the start codon had been missed. Nevertheless, the aggregate data provide strong evidence that the full coding sequence for the β subunit has been recovered. (i) Extensive attempts failed to reveal cDNAs in either of two separate libraries with a more extended 5' sequence. (ii) The major species generated by 5' extension studies terminated precisely at the point at which most of our clones started. (iii) The second ATG codon at the 5' end meets the consensus characteristics of known initiation sites (Kozak (1987) Nucleic Acids Res. 15:8125–8148). That it is preceded by a nearby 5' ATG codon is uncommon, but not rare (Kozak (1987) Nucleic Acids Res. 15: 8125–8148), and has been observed for the human α subunit (Shimizu et al. (1988) Proc. Natl. Acad. Sci. U.S.A. 85:1907–1911; Kochan et al. (1988) Nucleic Acids Res. 16:3584). (iv) As already noted, in vitro translation of an mRNA transcribed from the cDNA containing only the second ATG codon gives a polypeptide indistinguishable in length from the authentic β chains. An aberrant clone containing a start codon 48 nucleotides 5' to the presumed start codon directed the in vitro synthesis of a polypeptide with an apparent molecular weight appropriately greater than that of the β subunit. Therefore, the correspondence in apparent molecular weight between authentic β chains and the protein synthesized in vitro from clone 1 is meaningful. The RNA transfer blotting data show an mRNa of ≈2.7Kb, precisely what would be anticipated from the cDNA that was sequenced (FIG. 6), given a poly (A) tail of≈200 nucleotides. In the discussion that follows it is assumed that the β chain begins with the methionine residue coded for by the second ATG and is, therefore, 243 residues long.

Only a single clone containing the Cla I restriction site was observed among the 37 clones analyzed. This clone likely resulted from a single base mutation during the cloning and is unlikely to represent a normally occurring mRNA. Conversely, six clones showing the deleted sequence (FIG. 6B) were observed and likely reflected an authentic species of mRNA. If translated, it would code for a $M_r$~14,000 protein with only a single transmembrane segment.

The sequence of the β subunit contains potential sites for N-linked glycosylation at residues 5, 151, and 154. However, past and new incorporation data give no evidence for carbohydrate in the β subunit (Perez- Montfort et al. (1983) Biochemistry 27:5722–5728; Holowka and Metzger (1982) Mol. Immunol. 19:219–227; and Table I). The sequence shows no unusual features or homology to previously reported sequences, in particular to those associated with Fc receptors or with Fc binding factors.

A hydropathicity analysis suggests that the β subunit crosses the plasma membrane four times (FIG. 8). The hydrophilic $NH_2$ and COOH terminus would therefore be on the same side of the membrane. Expression of fragments of the β cDNA indicate that mAbβ-(NB) reacts within amino acids residues 149–243 (FIG. 7C) and that mAbβ(JRK) reacts with fragment containing residues 1–21 (FIG. 7B). Because neither antibody reacts appreciably with intact cells but both react strongly with cell sonicates, the combined results are consistent with the $NH_2$ and COOH terminus being on the cytoplasmic side of the plasma membrane.

Earlier studies had suggested that the β chain contained a $M_r$~20,000 "β," domain resistant to proteolysis while membrane bound (Holowka and Metzger (1982) Mol. Immunol. 19:219–227). This portion also contained those residues that were modified by an intrabilayer labeling reagent (Holowka and Metzger (1982) Mol. Immunol. 19:219–227; Holowka et al. (1981) Nature (London) 289:806–808) and became linked to the β and/or γ subunit when chemical crosslinking reagents were used (Holowka and Metzger (1982) Mol. Immunol. 19:219–227) and to the γ subunit when spontaneous disulfide linkage between the β and $γ_2$, subunits occurred (Kinet et al. (1983) Biochemistry 22:5729–5732). The remainder, "$β_2$,", appeared to contain the serine residues that became phosphorylated in situ (Perez-Montfort et al., (1983) Biochemistry 22:5733–5737; Quarto and Metzger (1986) Mol. Immunol. 23:1215–1223) but has never been positively identified as a discrete fragment. The sequence predicted by the cDNA for the β subunit suggests that part or all of either the $NH_2$-terminal 59 residues or the COOH-terminal 44 residues, or of both, is cleaved off to generate the β fragment.

EXAMPLE 11

Contransfection Experiments

The full-length coding sequences of the α and the 8 subunits were cotransfected in COS 7 cells by using a vector for transient expression. No IgE-binding sites were expressed at the surface of transfected cells.

Studies of the receptor with low affinity for IgE on macrophages revealed a component that could be chemically crosslinked to the IgE-binding portion and that had an apparent molecular weight similar to the β subunit of the high-affinity receptor (Finoloom and Metzger (1983) J. Immunol. 130:1489–1491). The peptides generated from this component by protease digestion appeared to differ from those released from 8 subunits, but it raised the possibility that other Fc receptors also contained β-like subunits that had heretofore escaped detection (Rivera et al. (1988) Mol. Immunol.). Evidence for this from RNA transfer blot experiments conducted at high stringency is not available. In particular, J774 cells are known to contain Fcγ receptors whose immunoglobul in-binding chain shows considerable homology to the α chain of the high-affinity receptor for IgE (Kinet et al. (1987) Biochemistry 26: 4605–4610). However, it was not possible to detect mRNA for β chains by the methods that were employed. Similarly, NTD lymphoma cells gave negative results even though they have Fcγ receptors and show a low molecular weight component that reacts with mAbβ(JRK) on immunoblots.

EXAMPLE 12

Isolation and Sequence Analysis of Peptides of the Gamma Subunit of Fc$_\epsilon$RI Fc$_\epsilon$RI was purified by affinity chromatography using TNP-lysine beads as described in G. Alcaraz et al., Biochemistry 26:2569–2575 (1987). The eluate was applied to sepharose 4B beads coupled by cyanogen bromide to monoclonal anti-β (JRK) (J. Rivera et al., Mol. Immunol. 25:647–661 (1988)). After washing the beads with 2 mM CHAPS in borate buffered saline at pH8, the bound material was eluted at 65° C. with 0.1% sodium dodecyl sulfate, phosphate buffered saline, pH 6.5. The subunits from Fc$_\epsilon$RI were then separated by HPLC size chromatography, the β and γ containing fractions recovered, reduced, alkylated and digested with trypsin (J.-P. Kinet et al., Biochemistry 26:4605–4610 (1987)). The resulting peptides were separated by HPLC reverse phase chromatography as in J.-P. kinet et al, Biochemistry 26:4605–4610 (1987). The chromatograms from the β and γ digests were compared and the non-overlapping q peptides were sequenced (J.-P. Kinet et al., Biochemistry 26: 4605–4610 (1987)).

EXAMPLE 13

Cloning and Sequencing of cDNA clones of the Gamma Subunit of FC$_\epsilon$RI Oligonucleotide probes were synthesized according to the sequences of peptide 3 (residues 41 to 47 SEQ ID No: 27) and of peptide 4 (residues 54 to 62). The sequences were GA(A/G)AA(A/G)TCIGA(T/C)GCTCTCTA and AA(T/C)CA(A/G) GA(A/G)ACITA(T/C)GA(A/G)ACI(T/C)TIAA (SEQ. ID No:9). The methods used to screen the λgt11 library, to purify, subclone and sequence the positive clones are known in the art (J.P. Kinet et al., Biochemistry 26:4605–4610 (1987)). Peptide 3 and peptide 4 were also synthesized using a peptide synthesizer ABI 431A. The purity of the synthetic peptides was assessed by HPLC reverse phase chromatography, amino acid composition and mass spectroscopy. The peptides were conjugated either to ovalbumin using m-Maleimidobenzoyl-N-hydroxysuccinimide ester (F.T. Liu et al, Biochemistry 18:690–697 (1979)) at a molar ratio of 5:1 or to sepharose 4B with cyanogen bromide. Rabbits were immunized with the ovalbumin-conjugated peptides, the antisera collected and the antipeptide antibodies purified by affinity chromatography using sepharose 4B conjugated peptides. The antipeptide antibodies were tested for reactivity with the γ subunit of Fc$_\epsilon$RI by Western blotting and for their ability to immunoprecipitate $^{125}$I-IgE receptor complexes (J. Rivera et al., Mol. Immunol. 25:647–661 (1988)). The nucleotide sequence of the γ subunit of rat Fc$_\epsilon$RI (SEQ ID No:26) obtained using the method of this invention, as well as the amino acid sequence (SEQ ID No:27) that it predicts, are shown in FIG. 9.

In order to isolate and characterize the cDNA for the γ subunit, cDNAs for the FC$_\epsilon$RI γ subunit were isolated from a λgt11 library prepared from rat basophilic leukemia (RBL) cells (J.P. Kinet et al., Biochemistry 26:4605–4610 (1987)) using oligonucleotide probes. Four peptide sequences were identified in a tryptic digest of the Fc$_\epsilon$RI γ subunits, and two of the peptides were used to synthesize two oligonucleotide probes (FIG. 9). The library was screened in duplicate with these two probes and overlapping plaques identified. Three discrete plaques were purified, subcloned and found to contain similar inserts of 0.6 to 0.7 kilobases (kb).

FIG. 9 shows the complete nucleotide sequence (SEQ ID No:26) of the γ cDNA, the deduced amino acid sequence (SEQ ID No:27) and the position in the sequence of the four original tryptic peptides. Analysis of the sequence (FIG. 10C) indicates an N- terminal hydrophobic signal peptide of 18 residues and a putative transmembrane domain separating a short extracellular portion of 5 residues from an intracytoplasmic domain. As predicted by earlier studies, the N-terminal processed ⁻subunit contains two cysteines, no methionine and no tryptophan residues (G. Alcaraz et al., Biochemistry 26:2569–2575 (1987)). Compositional analysis suggested that the γ subunit might contain one histidine residue (G. Alcaraz et al., Biochemistry 26:2569–2575 (1987)). However, biosynthetic dual labeling studies of the receptor using $^{35}$S methionine and $^3$H histidine, clearly indicated that no trace of histidine was incorporated into the receptor-associated γ subunit. Since the open reading frame derived from three independent clones, each predicts a histidine six residues from the C-terminal end, it is expected that the γ subunit undergoes a C-terminal processing which clips off the histidine-containing segment. Furthermore, because the peptide immediately preceding this histidine was recovered (FIG. 9 and SEQ ID No:26), the C-terminal segment must be cleaved after Lys 63. The predicted molecular weight of the fully processed γ would therefore be 7139 Da,in close agreement with values obtained for the purified reduced γ on sodium dodecyl sulfate - urea gels (G. Alcaraz et al, Biochemistry 26:2569–2575 (1987)).

Polyclonal antipeptide antibodies to a heptamer and to a nonamer peptide of the γ subunit (FIG. 9 and SEQ ID No:27) were prepared and tested for reactivity with IgE receptor complexes for RBL cells. Both purified antipeptide antibodies reacted in a Western blot assay with the unreduced dimer and the reduced monomer of partially purified γ subunits. In addition, both antibodies quantitatively precipitated receptor-bound $^{125}$I-IgE, either from an extract of RBL cells or from a preparation of partially purified receptors. Taken together, these results leave no doubt that the cDNAs isolated according to the present invention code for the γ subunit of Fc$_\epsilon$RI.

EXAMPLE 14

Expression of Receptor

In order to achieve expression of the receptor on the surface of COS 7 cells, the coding region of the α, β, and γ cDNAs were first subcloned separately into the SV 40 promoter-driven expression vector PSVL, prior to transfection into the COS-7 cells. The 810 bp EcoRI-Sty I restriction fragment of the α cDNA, the 965 bp EcoRI-EcoRV restriction fragment of the β cDNA and the 300 bp EcoRI-Dde I restriction fragment of the γ cDNA were subcloned separately into the Sma I site of the transient expression vector PSVL (Pharmacia, Uppsala, Sweden). These restriction fragments individually contained the entire coding sequence of the appropriate subunit and variable portions of untranslated sequences. The only foreign sequence was the starting EcoRI recognition sequence which belonged to the initial linker. Cultured COS7 monkey kidney cells were then transfected with 40 μl of DNA by the standard calcium phosphate precipitation technique (L. Davis et al, in Basic Methods in Molecular Biology, ed. L. Davis, Elsevier, New York (1986)). After 48 hrs, the transfected cells (panels A and a of FIG. 11), as well as RBL cells (panels C and D of FIG. 11), were examined for surface expression of IgE binding by an IgE rosetting assay. The cells (5×106 cells/ml) were incubated at room temperature with (panels B and D) or without (panels A and C) μg/ml of non-specific rat IgE for 30 min and then with 5 μg/ml of anti-DNP-IgE (F.T. Liu et al., J. Immunol. 124:2728–2736 (1980)). The cells were then rosetted with ox red blood cells that had been modified with 2,4,6-trinitrobenzene sulfonic acid according to a known method (M. Rittenberg et al., Proc. Soc. Exp. Biol. Med. 132:575–581 (1969)). The results are shown in FIG. 11. FIG. 11A shows IgE-binding activity expressed by cells cotransfected with the α, β and γ subunits. Virtually all RBL cells, used as a positive control, formed rosettes (FIG. llC). The rosettes were completely inhibited by preincubation of the cells with rat IgE (FIG. 11B and D) but not with human IgE (not shown). This coincides with the species specificity for the rat $Fc_\epsilon RI$ (A. Kulczycki et al., J. Exp. Ned. 139:600–616 (1974)).

In order to study the requirements for surface expression of IgE-binding activity, the cells were transfected with different combinations of the cDNAs for the three subunits, as shown in Table 2.

COS-7 cells were transfected with different combinations of cDNAs for the three subunits of $Fc_\epsilon RI$ (FIG. 11). The resetting assay was performed for each transfection shown in Table 2. The assessment of the mRNA by Northern blotting was performed one time only (on 2×10$^7$ cells). Inhibitor was added to the cells in the experiments marked by an asterisk in Table 2 (50 μg/ml of non-specific rat IgE was added to the cells 30 minutes prior to the addition of the specific mouse anti-DNP IgE).

TABLE 2

Transfection Experiments

| Cells | Transfections cDNA | No. | Expression Receptor mRNA | Ige Binding (rosettes/cells counted) |
|---|---|---|---|---|
| COS 7 | 0 | 9 | 0 | 0/12,948 |
| | α | 2 | α | 0/4,050 |
| | αβ | 2 | αβ | 0/3,504 |
| | α | 4 | α | 0/8,030 |
| | β | 1 | β | 0/2,069 |
| | αβ | 29 | αβ | 920/41,238 |
| | αβ | 4 | αβ | 0/7,542* |
| RBL | 0 | — | αβ | "100%" |

*Experiments where inhibitor was added.

Table 2 summarizes the data derived from all the transfection experiments performed as described up to here. The success rate of the transfection experiments has improved since that data was collected so that there is now routinely achieved 5±2% expression of IgE binding when α, β and γ are simultaneously cotransfected.

Successful transfection was achieved for all combinations, as assessed by Northern blotting, but rosette forming cells were only detected after cotransfection of the full set of the cDNAs. These results indicate that the β and γ subunits are required for surface-expression of the IgE-binding α subunit. It is further indicated that only the fully assembled receptor reaches the plasma membrane. This phenomenon has also been observed in other systems (M. McPhaul et al., Proc. Natl. Acad. Sci. U.S.A. 83:8863–8867 (1986); Y. Minami et al., Proc. Natl. Acad. Sci. U.S.A. 84:2688–2692 (1987)) and may be generally applicable to polymeric membrane proteins.

The easy dissociability of β and γ, from α (B. Rivnay et al, Biochemistry 21:6922–6927 (1982)) has raised persistent uncertainty about whether conceptually, $γ_2$, and β should be considered as subunits of FCεRI or as "receptor associated" proteins. (An example of the latter is the CD3 complex which associates with the antigen receptor on thymus-derived lymphocytes (H. Clevers et al., Ann. Rev. Immunol. 6:629–662 (1988)). The subunit model for FcεRI has been favored, for example, on the basis of the coordinate biosynthesis and catabolism of α, β and γ,(R. Quarto et al, Molec. Immunol. 22: 1045–1052 (1985)). The new data on transfected cells obtained by the present invention provides the strongest evidence yet obtained that αβγ2 is the minimal structure for $Fc_\epsilon RI$.

The present model for the tetrameric $Fc_\epsilon RI$ receptor is illustrated in FIG. 12 and SEQ ID NOS. 28–30. In this model each of the 589 amino acid residues of which the expressed receptor is composed is shown as a circle. In the diagram, the exterior of the cell would be at the top, the plasma membrane in which the receptor is embedded would be in the middle, and the interior of the cell towards the bottom. Each of the polypeptide chains (the α, SEQ ID NO:28, on the left, the β, SEQ ID NO:29, chain in the middle and the two γ, SEQ ID NO:30, chains on the right) contains one or more transmembrane segments.

The α (SEQ ID NO:28) chain is believed to contain two intrachain disulfide loops, and the sequences of these loops show considerable homology with immunoglobulins (J. P. Kinet et al., Biochemistry 26:4605 (1987); A. Shimizu et al, Proc. Natl. Acad. Sci. U.S.A. 85:1907 (1988); J. Kochan et al., Nucleic Acids Res. 16:3584 (1988)). Thus, the α subunit is another member of the immunoglobulin superfamily (A. Williams et al., Ann. Rev. Immunol. 6:381 (1988)). The extracellular and transmembrane segments of the α chain show considerable homology with the immunoglobulin binding chain of Fc receptors that bind IgG (J. Ravetch et al., Science 234:178 (1986)), but the intracellular cytoplasmic tail is quite different. The carbohydrate residues that are covalently attached to the extracellular portion of the a chain are not indicated in FIG. 12. There are seven potential sites for N-linked carbohydrates (J.P. Kinet et al., Biochemistry 26:4605 (1987); A. Shimizu et al., Proc. Natl. Acad. Sci. U.S.A. 85:1907 (1988)), but which of these that are actually used by the cell remains to be determined. Studies show that the carbohydrate is not essential for the binding of IgE by this chain (B. Hempstead et al, J. Biol. Chem. 256:10717 (1981)).

The β chain (SEQ ID NO:29) contains four transmembrane segments (J. P. Kinet et al, Proc. Natl. Acad. Sci. U.S.A. 85:6483 (1988)) and previous studies with monoclonal antibodies (J.P. Kinet et al., Proc. Natl. Acad. Sci. USA 85:6483 (1988); J. Rivera et al., Mol. Immunol. 25:647 (1988)) show that the amino- and carboxyltermini which are respectively 59 and 43 residues long, protrude from the cytoplasmic face of the plasma membrane. Similarly, the γ chains (SEQ ID NO:30) have an extensive intracellular extension but only very limited exposure to the exterior.

According to the general model, the putative transmembrane domains of the individual subunits are predicted from their respective hydropathicity plots (see FIG. 10, wherein a net free energy of >20 kcal/mol for transfer to water suggests a transmembrane segment or a leader peptide (D. Engelman et al, Ann. Rev. Biophys. Biophys. Chem. 15:321–353 (1986)). These plots suggest one, four and one hydrophobic domains for the α, β and each γ, respectively (i.e., seven transmembrane domains for the entire receptor). Members of a family of receptors interacting with G proteins also contain seven transmembrane domains (I. Herskowitz et al., Cell 50:995–996 (1987)). This family includes β and α adrenergic, muscarinic receptors and rhodopsin. Although no sequence homology between $Fc_\epsilon RI$ and these receptors is found, it is significant that an interaction between $Fc_\epsilon RI$ and G proteins has been postulated to explain at least some of the biochemical pathways activated by this receptor (S. Cockcroft et al., Nature 314:534–536 (1985)). The topology of the α and β subunits has been discussed in J. P. Kinet et al., Biochemistry 26:4605–4610 (1987) and A. Shimizu et al., Proc. Natl. Acad. Sci. U.S.A. 85:1907–1911 (1988), in particular, the cytoplasmic localization of the C- and N-terminal portions of the β subunit. Two pieces of evidence support the topology of the γ-dimer as shown in FIG. 12: The γ can be oxidatively iodinated on inverted vesicles but not on intact cells (D. Holowka et al.,; J. Biol. Chem. 259:3720–3728 (1984)) and, in vivo, γ becomes phosphorylated on threonine residues (R. Quarto et al., Mol. Immunol. 23:1215–1223 (1986)). None of the relevant residues are present in the small presumptive extracytoplasmic segment of γ but all are present on the presumptive cytoplasmic tail, i.e., two tyrosine and four threonine residues.

As a further means to examine the topology of the receptor, the putative extracellular and intracellular segments of the three subunits were analyzed for their relative content of basic residues, as suggested by G. von Heijne Biochim. Biophys. Acta 947:307–333 (1988). He found the ratio of basic/total residues varies as a function of the length of the segment studied, but in general was substantially higher in the non-translocated (intracellular) segments than in the translocated (extracellular) segments of membrane proteins. Table 3 below shows a good correspondence between the ratios calculated for the present model and the ratios expected on the basis of "known" membrane proteins (G. von Heijne, Biochim. Biophys. Acta 947:307–333 (1988)), thereby providing independent support for the topological model presented here.

22:5729–5732 (1983)). The likeliest candidates for this bond are γ-cys7 and β-cys80 which are predicted to be topologically close. This would then require that at least the γ-cys26 residues are disulfide-linked in the γ dimer. Preliminary data on the receptor biosynthesis suggest that α and β interact with each other.

The functional properties of $Fc_\epsilon RI$ are broadly similar to those of several $Fc_\gamma R$. $Fc_\gamma R$ appears to bind to homologous segments of the immunoglobulin's Fc region (B. Helm et al., Nature 331:180–183 (1988); A. Duncan et al., Nature 332:563–564 (1988)), and the binding site on the receptor is found on a homologous polypeptide having immunoglobulin-like domains (J. P. Kinet et al., Biochemistry 26:4605–4610 (1987); J. Ravetch et al., Science 234:718–725 (1986)). Both types of receptors need to be aggregated to initiate cell activation and, where studied, the latter appears to involve generation of broadly similar second messengers (H. Metzger et al., Ann. Rev. Immunol. 4:419–470 (1986); N. Hogg, Immunol. Today 9:185–187 (1988)). It is surprising, therefore, that whereas $Fc_\epsilon RI$ consists of four polypeptide chains, seven transmembrane segments and five cytoplasmic segments, $Fc_\epsilon RI$ appear to perform similar functions with a much simpler structure, i.e., an α-like subunit alone. The extreme case is that of $Fc_\gamma RIII$ which appears to lack even transmembrane and intracellular segments (P. Selvaray et al., Nature 333:565–567 (1988); D. Simmons et al., Nature 333:568–570 (1988); T. Huizinga et al., Nature 333:667–669 (1988)). It has been suggested that additional components of Fcγ receptors may have thus far been missed. Possibly such components are even more easily lost upon solubilization of the receptors than are the β and γ subunits of FRI (J. P. Kinet et Biochemistry 24:4117–4124 (1985)). A reasonable interpretation is that such hypothetical components would be homologous to β or γ or both. The availability of genetic probes for the latter components will now permit an in-depth exploration of this possibility.

The success in expression of IgE binding achieved according to the present invention has important therapeutic implications. Degranulation of mast cells and basophils

TABLE 3

Ratio Lys + Arg/total in Translocated and Untranslocated Segments of Receptor Subunits

| Polypeptide | | No. residues | Extracellular (translocated) Ratio | | | Not residues | Intracellular (untranslocated) Ratio | |
|---|---|---|---|---|---|---|---|---|
| | | | found | expected | | | found | expected |
| α | | 179 | 0.13 | 0.11 | | 22 | 0.31 | 0.19 |
| β | loop 1 | 17 | 0.06 | 0.04 | N-term | 59 | 0.10 | 0.10 |
| | loop 3 | 28 | 0.03 | 0.04 | loop 2 | 12 | 0.25 | 0.20 |
| | | | | | C-term | 43 | 0.12 | 0.18 |
| γ | | 5 | 0 | 0.08 | | 36 | 0.22 | 0.16 |
| αβγ$_2$ | | 234 | 0.045 | 0.02–0.06 | | 208 | 0.17 | 0.12–0.16 |

The expected values calculated from the data in FIG. 8 of G. von Heijne, Biochim. Biophys. Acta 947, 307–333 1988), in which the ratio found for the extra-membrane segments from "known" proteins has been plotted as a function of the segments' length.

The model clarifies several important features with respect to the organization of the subunits. The β and dimer of γ interact with each other; in detergent solutions they dissociate from 5the α as a unit before dissociating from each other (J. Rivera et al., Mol. Immunol. 25:647–661 (1988), and occasionally, β and the γ dimer are observed to be disulfide-linked to each other (J. P. Kinet, Biochemistry triggered by $Fc_{68}$ RI accounts for many of the symptoms of allergy. Given the high incidence of this disorder, the discovery of a specific inhibitor of IgE binding is expected to yield enormous therapeutic benefits. The development of such an inhibitor has been hampered by the lack of a practical in vitro assay for the binding of human IgE to the human receptors. For example, a recent assessment of IgE-derived peptides of their inhibitory capacity had to be determined by skintesting (B. Helm et al., Nature 331:180–183 (1988)), a cumbersome and potentially dangerous procedure.

That the present invention achieves the expression of the transfected rodent receptor indicates that human Fc$_\epsilon$RI can be similarly expressed. Alternatively, since at present only the cDNA coding for the human α subunit has been isolated (A. Shimizu et al, *Proc. Natl. Acad. Sci. USA* 85:1907–1911 (1988); J. Kochan et al, *Nucl. Acids Res.* 16:3584 (1988)), it is expected that it can be expressed in cotransfections with the cDNAs coding for the rodent β and γ chains.

A comparison between the human and rat α subunits is set forth in Table 4 below.

TABLE 4

Comparative Properties of Human and Rat Alpha Chains

| Domain | Species | | % Homology |
| --- | --- | --- | --- |
| | Human | Rat | |
| Extracellular | 180 | 181 | 49 |
| Transmembrane | 21 | 21 | 67+ |
| Intracellular | 31 | 20 | 23 |
| Total | 232 | 222 | 47* |

*Wt ave.
+ Human: (amino used residues 178–204 of SEQ ID NO: 13) WLQFFI-PLLVVILFAVDTGLFISTQQQ
Rat: (amino acid residues 179–205 of SEQ ID NO: 12) WLQLIFPSLAVIL-FAVDTGLWFSTHKQ It may be seen from the above Table that there is an overall homology between the human and rat alpha chains of about 47%, but an almost 70% homology in the presumed transmembrane domains. Indeed, when the transmembrane domains are examined closely, there is a stretch of 10 consecutive residues that are completely identical. This stretch of consecutive residues is underlined in Table 4.

Because the transmembrane segment is the region of the α chain that is most likely to interact with the β1 and γ chains, it was expected that the human a chain would be expressible, if transfected, along with the rat β and γ chains. This has proved to be the case as the present inventors have been able to express human IgE binding by COS cells transfected simultaneously with the human α and the rat β and γ subunits. It will be advantageous, of course, to have permanently transfected cell lines and for such lines, one will want to utilize combinations of the IgE receptor subunit. subunits disclosed herein.

EXAMPLE 15

The Beta Subunit of FC$_\epsilon$R Is Necessary for Expression in Mast Cells

FIGS. 20 and 21 present the results obtained from FACS analysis (IgE binding) of cells transfected with FIG. 20: represents KU812 cells (a basophil line).

FIG. 21: represents COS-7 transfected cells.

The clone of Ku812 cells used does express the mRNA for the three subunits alpha, beta and gamma but the receptor is not naturally expressed on the surface.

In FIG. 21, the transfection of human alpha and gamma in COS-7 cells is confirmed to be sufficient for expression of the alpha-gamma complex on the surface of the transfectants. These results also show that human beta and not rat beta associates efficiently with human alpha and that therefore, rat beta cannot replace human beta.

FIG. 20 illustrates that transfection of alpha-gamma in KU812 results in very little expression of receptors. The level of expression is similar to the level obtained after transfection of beta and gamma. Therefore this level may be attributable to the endogenous alpha (for beta and gamma transfection) or to the endogenous beta (for alpha and gamma transfection). By contrast the level of expression after co-transfection of the three cDNAs is very substantial.

From these results, it may be concluded that:

1. in mast cells and basophils, regulation of the level of expression of the receptor may be different than in fibroblasts.

2. in human mast cells and basophils, receptor expression requires the presence of alpha, beta and gamma; whereas in transfected fibroblasts, human alpha and gamma are sufficient.

EXAMPLE 16

Isolation, Mapping and Sequencing of the Human FceRI β Gene

Initial attempts to isolate human β cDNA clones were by screening a human mast cell cDNA library with full-length rat and mouse cDNA probes. These probes were radiolabeled and used to screen 7×10$^5$ colonies. Four clones were isolated, all of which contained a 153 bp insert with 73% homology to rat β cDNA. The sequence of this insert corresponded to a portion of β which includes the intracellular loop and the third transmembrane domain. These four identical clones are the likely result of library amplification of a single clone generated by recombinations. Two additional libraries were screened: another mast cell cDNA library and a cDNA library derived from basophil-enriched leukocytes. The latter library was also used to isolate human γ cDNA clones. A total of 107 independent cDNA clones were screened with a panel of murine probes and oligonucleotides and with the 153 bp human β probe. However no additional clones were isolated. 6×10$^5$ independent genomic clones from a human genomic leukocyte library with the radiolabeled 153 bp human probe were subsequently screened, and 10 clones with an average size insert of 25 kb were isolated. These clones all hybridized with two 20 meroligonucleotide probes corresponding to the beginning and the end of the rat β coding γ sequence. Four different restriction patterns could be generated from the 10 clones. However, southern blots with various oligonucleotide probes scanning different regions of the rat β coding sequence indicated that the four restricted patterns were not the product of different genes. Rather the clones showed differences in the lengths of the sequences flanking the β gene.

One clone containing a 25 kb insert was chosen for further characterization mapping and sequencing. A restriction map shown in FIG. 13 was constructed by complete and incomplete digestion with the restriction endonucleases Hind III, Pst I, BamH I, Xba I, Sma I and Kpn I. A 3.2 kb Hind III fragment was found to hybridize with oligonucleotide probes corresponding to the start codon, and transmembrane region I and II of rat β. A 2.8 kb Sma I fragment hybridized with rat β probes of transmembrane domain III and IV and a 4.5 kb Sma I fragment with probes of the stop codon region. The 3 fragments were subcloned into pGEM 3 zf (+) or (−) and sequenced in full (FIG. 14) and SEQ ID NO:31. The fragment corresponding to the 0.9 kb gap between the Hind III and 2.8 kb Sma I fragments was produced by PCR and sequenced. Analysis using PCR confirmed that the two Sma I fragments were adjacent to each other.

By comparing the sequences of the human β gene and the rat β cDNA (FIG. 15) seven homologous regions which were likely localized to correspond to seven different exons.

EXAMPLE 17

Synthesis of Human β cDNA Coding Sequence

In order to confirm the sequence of the exons and to define the intro-exon borders, human β cDNA was synthesized by reverse transcription of RNA purified from basophil-enriched leukocytes followed by an amplification of the reverse transcripts using the polymerase chain reaction (PCR) (described in Materials and Methods herein). This applied product extended from 2 nucleotides preceding the start codon to 32 nucleotides following the stop codon. The cDNA sequence was found to be identical to the corresponding sequence of the human β gene. This confirmed that the coding sequence of human β is contained in seven exons. Furthermore, the comparison of cDNA and gene sequences and the detection of consensus sequences for intron-exon borders in the human β gene allow for a precise determination of these borders. The 5' borders of the six intervening introns invariably start with GT and the 3' borders end with AG.

EXAMPLE 18

Analysis of Human B Transcripts

Figure 16C:
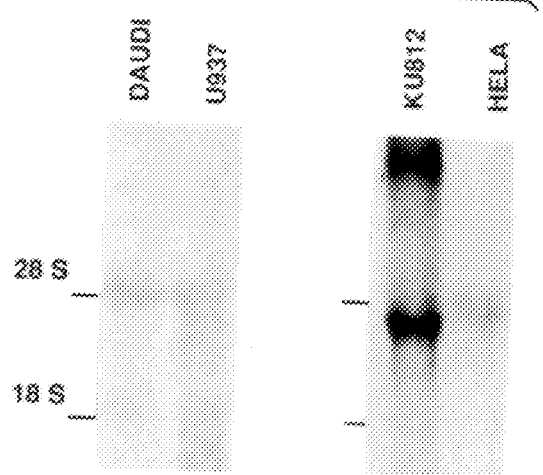
Figure 16B:
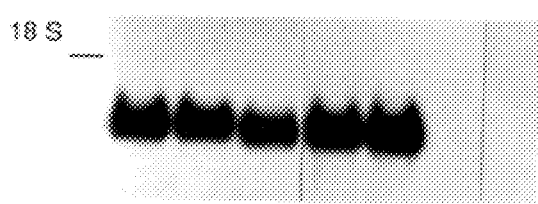

To evaluate the length of 5' and 3' untranslated sequences, the size of human β transcripts was analyzed. RNA from basophil-enriched leukocytes obtained from different individuals were hybridized by northern blotting with the radio-labeled 153 bp human β probe (FIG. 16A) Two transcripts around 3.9 kb were found in human basophils but not in COS-7 cells. The human transcripts are substantially longer than their rodent counterparts (2.7 and 1.75 kb) (Ra. 1989, Kinet, 1988) as detected in RBL cells by crosshybridization. This longer size may explain initial failures to isolate human β cDNAs from the three oligo-dT primed libraries. Similar results were obtained with a full-length cDNA probe of human β. Hybridization of the same RNAs with a human α cDNA probe revealed transcripts for α of the expected size (1.1 kb) (FIG. 16B). RNA from different cell lines were also hybridized with a full length human β cDNA probe (FIG. 16C). The message for human β is only detected in the basophil line KU812 but not in U937, Daudi and Hela cells. An additional band is seen in KU812 which could correspond to unspliced transcripts.

With an open reading frame of 732 bp and assuming 200 bp for the poly A tail, human β transcripts should contain about 3 kb of untranslated sequences. FIG. 15 shows that most of the untranslated sequences are in the seventh exon. The possibility that additional exons of 3' or 5' untranslated sequences had not yet been identified was also explored.

EXAMPLE 19

A. Characterization of the (A) 5' End and of the Transcription Initiation Site

The transcription start site was determined by sequencing directly a PCR amplified product of the reverse transcribed RNA as described in "Experimental Procedures". RNA from basophil-enriched leukocytes was reverse transcribed from a primer of the human β coding sequence. Poly-A tails were added to the reverse transcripts by treatment with terminal transferase and the resulting cDNAs were amplified by PCR. Single stranded DNAs (positive strands poly dT tailed) were then produced by asymmetric PCR and directly sequenced. The cDNA sequence of the negative strand corresponding to the 5' end of the RNA is shown in FIG. 5A and is compared to the relevant sequence of the β gene. The perfect match between the two sequences ends after GGGTT. Then the CDNA sequence reproducibly shows a C, which is not present in the gene, followed by the expected poly-A tail. This additional C may correspond to the G of the cap structure and indicate the location of the start site.

Experiments of 5' extension (FIG. 17B) confirmed that there is a major start site in this area (about 11 nucleotides 3' of the position described above). It is difficult, though, to exclude the possibility that the faint bands seen below and above the major start site correspond to minor start sits. However the presence of a TATAAA box found in the 5' sequence supports the existence of a unique start site. In addition the location of the TATAAA box (usually 25 nucleotides 5' of the start site) is more consistent with the precise localization of the start site as shown.

Figure 17A:
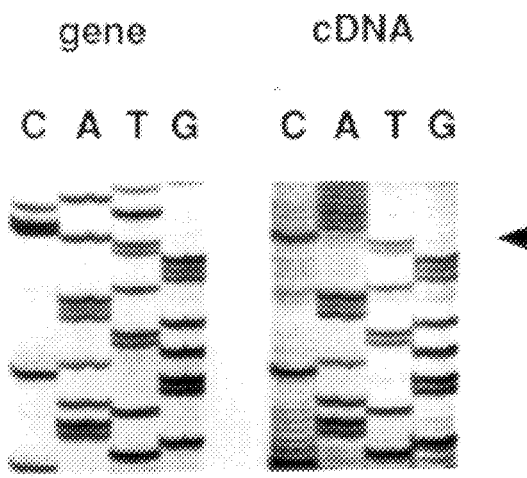
Figure 17B:
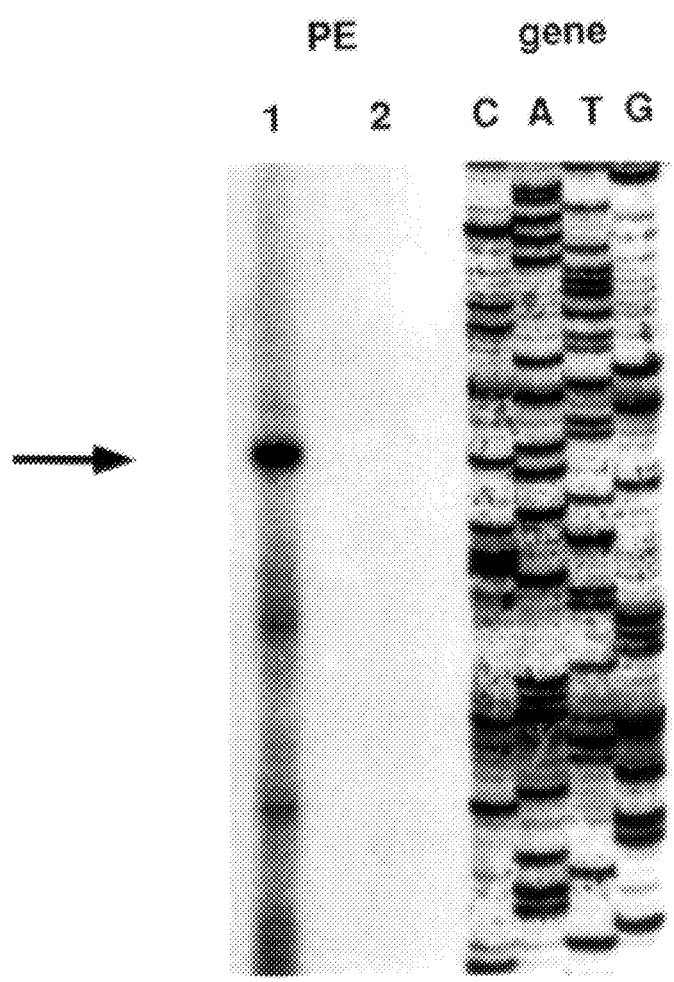

Indeed the TATAAA box is located between nucleotides 29 and 24 upstream of this start site as shown in FIG. 17A. Taken together the data indicate that the human β mRNA start with the sequence AACCC (see FIG. 14, SEQ ID NO:31, and FIG. 17A) and has 102 bp of 5' untranslated sequence.

B. Characterization of the 3' end

A comparison between the rat β cDNA and human β gene sequences FIG. 15) shows that the seventh exon of the β gene extends at least from nucleotides 6773 to at least nucleotide 8910. But an additional 3' untranslated sequence (about 800 bp) had to be found to fully account for the 3.9 kb transcripts. To analyze whether the missing sequence was part of the seventh exon or of other undetected exons, three probes from the β gene were prepared to test their reactivity with β transcripts. These transcripts hybridized in northern blots with both the NsiI-BamHl fragment (nucleotides 8460–9250) and the BamHI-SphI fragment (nucleotides 9250–9714) but not with the fragment 3' of the SphI site. Interestingly two polyadenylation signals AATAAA are found at nucleotides 9663 and 9758 (FIG. 14 and SEQ ID NO:31). Therefore this region is likely to correspond to the end of exon 7. It is likely that both polyadenylation signals could be used to create the apparent doublet of transcripts around 3.9 kb (see FIG. 16).

EXAMPLE 20

Organization of the Human β Gene

Taken together the data presented herein indicate that the human β gene contains seven exons and six introns and spans about 10 kb. Exon 1 codes for 102 bp of 5' untranslated sequence and the first 18 amino acid residues of the N-terminal cytoplasmic tail. Exon 2 encodes the remaining of the cytoplasmic tail and the first three residue of TM1. Exon 3 codes for the remaining of TM1, the first extracellular loop and the first half of TM2. Exon 4 encodes the second half of TM2 and a portion of the cytoplasmic loop. Exon 5 codes for the last three residue of the cytoplasmic loop, TM3 and most of the second extracellular loop. Exon 6 codes for the last two residues of the extracellular loop, TM4 and the first quarter of the C-terminal cytoplasmic tail. Finally, exon 7 codes for the remaining of the cytoplasmic tail and the long untranslated 3' sequence.

EXAMPLE 21

The Human β Protein

The human β protein comprises 244 amino-acid (aa) residues and has a molecular mass of 26,532 daltons (FIG.

18). Similar to rat (243 aa) and mouse β (236 aa), human β contains four hydrophobic segment suggestive of transmembrane domains (TM) but no leader peptide. FIG. 19 shows an alignment of the human sequence (SEQ ID NO:32) with the rat (SEQ ID NO:33) and mouse (SEQ ID NO:34) sequence. The consensus sequence for β (not shown) from the three species (rat, mouse and human) shows that 91.4% of the amino-acid residues are homologous while 68.7% are identical.

EXAMPLE 22

Transfection in COS-7 Cells: Expression of Human and Hybrid $Fc_\epsilon RI$ Receptors

TABLE 5

Functional expression of FcεRI after transfection of various subunit combinations

| Transfected cDNAs | | | n | % Fluorescent cells (FACS) Mean ± SD |
|---|---|---|---|---|
| Human α | — | — | 1 | 0.2 |
| Human α | Human β | — | 1 | 0.2 |
| Human α | — | Human γ | 7 | 10.4 ± 8.7 |
| Human α | Human β | Human γ | 7 | 8.3 ± 5.0 |
| Human α | Rat β | Human γ | 4 | 5.4 ± 3.4 |
| Rat α | Rat β | Rat γ | 8 | 18.0 ± 17.8 |
| Rat α | Human β | Rat γ | 10 | 2.4 ± 2.0 |
| Rat α | Human β | Human γ | 5 | 1.8 ± 1.3 |
| Mouse α | Mouse β | Mouse γ | 4 | 8.2 ± 5.6 |
| Mouse α | Human β | Mouse γ | 6 | 1.6 ± 1.2 |
| Mouse α | Human β | Human γ | 2 | 1.5 ± 0.8 |
| Human α | — | Rat $\gamma_{trunc}$ | 7 | 1.4 ± 1.0 |
| Human α | Rat β | Rat $\gamma_{trunc}$ | 5 | 3.2 ± 2.8 |
| Human α | Human β | Rat $\gamma_{trunc}$ | 7 | 7.4 ± 7.9 |
| Rat α | Rat β | Rat $\gamma_{trunc}$ | 2 | 9.3 ± 0.8 |
| Rat α | Human β | Rat $\gamma_{trunc}$ | 2 | 0.4 ± 0.5 |

It was found that co-transfection of α, β, and γ cDNAs is necessary to promote expression of rat or mouse $Fc_\epsilon RI$ on the surface of transfected COS-7 cells. By contrast, co-transfection of human α and β cDNAs results in the surface expression of αγ complexes without apparent need for γ. With the availability of human γ cDNAs, the question was explored whether human β would influence in any way the efficiency of surface expression of the human receptor complex. Table 5 shows that co-transfection of human α and γ cDNAs into COS-7 cells results in 10.4%±8.7 of the cells being fluorescent when analyzed by FACS after binding of fluoresceinated IgE. This level of expression is not significantly modified when human β cDNA is co-transfected with human α and γ cDNAs (8.3%±5.0). Thus, human β does not seem to influence the level of surface expression of human FcεRI in transfected COS-7 cells. Substituting rat β for human β reduces the level of expression (5.4%±3.4).

The effect of substituting human β for rat β was analyzed. Co-transfection of rat α, β, γ cDNAs result in much higher level of expression (18.0%±17.8) than co-transfection of rat α, γ with human γ (2.5%±2.0) (Student's t statistic=2.75; p≦0.014). Similarly co-transfection of mouse α, β, γ cDNAs is more efficient (8.2%±5.6) than co-transfection of mouse α, γ with human β (1.6%±1.2) (Student's t statistic:2.91; p≦0.019). Because replacing rat γ or mouse γ with human γ does not restore expression (compare 2.4% with 1.8%, and 1.6% with 1.5%), it is likely that the problem of expression resides in the human β-rat α or human β-mouse α interaction.

It is known that truncation of the cytoplasmic tail of rat γ prevents the surface expression of human α in transfectants (Varni-Blank, 1990). The question was whether human β could complement the surface expression of human α in these conditions. It was confirmed that co-transfection of human α with truncated rat γ permits only very poor surface expression of αγ complexes (1.4%±1.0). When human β is co-transfected with the latter combination there is an increase of expression (7.4%±7.3, n=7). However this increase does not become significant (p≦0.035) when one aberrant point is not included in the seven experiments. The same increase is not observed when rat β is substituted for human β (3.2%±2.8) suggesting again that there may be specific points of interaction between human α and β. In other experiments using the truncated rat γ, it was found that human β cannot be substituted for rat β in its interaction with rat α (compare 9.3%±0.6 with 0.4%±0.4; (t=13.0; p≦0.006).

Taken together these data indicate that there is a tendency for human β to interact more efficiently with human α than does rat β, but the species specificity is weak. By contrast, there is a strong species specificity in the interaction between rat β and rat α or between mouse β and mouse α.

Human αγ complexes may be expressed on the surface of transfected cells. Moreover co-transfection of human α and γ with rat β results in only 20% of the receptors being αβγ complexes, the remaining 80% being αγ complexes. Therefore, it is theoretically possible that αγ complexes occur naturally. However in view of the species specificity of interaction between human β and α (see above), previous results obtained from the co-transfection of human α and γ with rat β suggest the in vivo situation could be different.

These genetic results, of course, provides much more than an assay, as important as the latter may be. Through directed mutation it will, in addition, allow the development of further information regarding the critical binding regions. It is expected that, using this information, rational drug design will become possible. It is further expected that it will be possible to block the function of the receptor itself, i.e., it will be possible to interfere with the early biochemical signals that result from activation of the receptor.

EXAMPLE 23

Detection of a Candidate Inhibitor Substance

In still further embodiments, the present invention concerns a method for identifying new $Fc_\epsilon RI$ inhibitory compounds, which may be termed as "candidate substances." It is contemplated that this screening technique will prove useful in general identification of any compounds that will serv e the purpose of inhibiting the formation of $Fc_\epsilon RI$ as measured by various cell activation assays. (Mouse Interleukin-2 ELISA kit, Alberts et al., pp. 179–180, Adamczewski et al. (in press), Barones et al., 1991).

Thus, in these embodiments, the present invention is directed to a method for determining the ability of a candidate substance to inhibit the formation of the human $Fc_\epsilon RI$ complex, the method including generally the steps of:

(a) obtaining a composition comprising the human alpha, beta and gamma subunits of $Fc_\epsilon RI$ that are capable of complexing to form a functional and/or expressed receptor;

(b) admixing a candidate inhibitor substance with the composition; and (c) determining the functional or expressed ability of the admixture.

An important aspect of the candidate substance screening assay hereof is the ability to prepare a composition of alpha, beta and gamma subunits in a relative purified form, for example, in a manner discussed herein. An aspect of the candidate substance screening assay is that without at least a relatively purified preparation, one will not be able to assay specifically for $Fc_\epsilon RI$ inhibition, as opposed to the effects of the inhibition upon other substances in the extract which then might affect the receptor. In any event, the successful cloning and isolation of the beta subunit now allows for the first time the ability to identify new compounds which can be used for inhibiting the $Fc_\epsilon RI$ in specific ways, thereby inhibiting the effects of the $Fc_\epsilon RI$ when bound to IgE.

The candidate screening assay is quite simple to set up and perform, and is related in many ways to the assays discussed above for determining $Fc_\epsilon RI$ activity. After obtaining a relatively purified preparation of the alpha, beta and gamma subunits, one will desire to simply admix a candidate substance with the preparation, preferably under conditions which would allow the receptor to form but for inclusion of an inhibitory substance. Thus, for example, one will typically desire to use cell activation assays as indirect measures of the presence of a functional receptor, or receptor expression, or both.

Accordingly, one will desire to measure or otherwise determine the activity of the relatively purified receptor in the absence of the assayed candidate substance in order to assess the relative inhibitory capability of the candidate substance.

In still further embodiments, the present invention is concerned with a method of inhibiting receptor formation and/or function which include subjecting the subunits to an effective concentration of a candidate substance identified in accordance with the candidate screening assay embodiments. This is, of course, an important aspect of the invention in that it is believed that by inhibiting the receptor one will be enabled to treat or prevent various aspects of allergic reactions. It is believed that the use of such inhibitors to block the release of histamine by binding of IgE to $Fc_\epsilon RI$ and serve to treat or palliate the symptoms of an allergic response. Inhibitors may be useful by themselves or in conjunction with other therapies.

EXAMPLE 24

Identification and Use of $Fc_\epsilon RI$ Inhibitors

If the action of receptor of IgE is inhibited, the allergic reaction will not proceed. This inhibition may be either at the level of transcription, translation, or protein action. Interference with transcription would necessitate interference with mRNA formation on the DNA template. Preferably, interference with the translation would necessitate interfering with the synthesis of proteins on the mRNA template. Alternatively, the action of the receptor may itself be disrupted either by destroying the structure of the receptor, prohibiting its formation, or binding the receptor or components thereof irreversibly to inhibitors.

Specifically designed peptides which block the function of the receptor are extremely valuable in preventing and treating allergic diseases. Embodiments of these blockers (antagonists) include any substrate analogues or inhibitor, e.g., oligopeptides or their derivatives which contain the amino acid sequence of the IgE binding site. Methods for identifying suitable inhibitors form candidate substances are disclosed in Example 23.

EXAMPLE 25

Preparation of the Human β Polypeptide by Recombinant Techniques

It is an additional object of the present invention to provide a ready means for producing the human beta subunit for use in detecting inhibitors, to develop treatment modalities, to develop antibodies for detection of the subunit, and to develop inactive mutants of the human beta subunits, which may also be use to inhibit formation of the $Fc_\epsilon RI$. Such mutants may be introduced into transgenic animals, for example, to produce animals useful for β assays.

An exemplary embodiment for preparing the beta subunit protein is to prepare a nucleic acid segment which includes a nucleic acid sequence capable of encoding the desired protein or polypeptide. This segment may be that which encodes the entire subunit or only some portion of it, for example, the alpha or gamma binding domain of the subunit. The segment may be as small as that capable of triggering a positive signal with an antibody, thereby, identifying the presence of a beta subunit. Segments functionally equivalent to those shown in FIG. 14, may also be selected depending on the desired polypeptide to be produced. Functional equivalence may be determined by testing whether the segment can cause cell activation using techniques disclosed herein to detect inhibitors from among candidate substances.

The nucleic acid segment selected is transferred into an environment appropriate for expression of the segment as a polypeptide. This environment may be a vessel containing a mixture capable of inducing expression. Alternatively, the segment may be transferred to a host cell by transformation, transfection via a recombinant expression vector, electroporation, or a "gene gun." The host cell may be selected from CHO cells, T cells, KU812 cells, P815 cells, or the like.

The recombinant expression vector will generally include a promoter. Embodiments of promoters are the α4 promoter, or any other suitable prokaryotic or eukaryotic promoters.

EXAMPLE 26

Antibodies Against the Proteins of the Present Invention

In other embodiments, the invention concerns the preparation of antibodies to the beta subunit of $Fc_\epsilon RI$ and species derived therefrom, either recombinant or nonrecombinantly prepared.

Compositions which include monoclonal antibodies of the present invention may be prepared by first fusing spleen cells of a rodent with myeloma cells from the same rodent species, wherein the rodent providing the spleen cells have been immunized with the β subunit peptide, precursor, or related peptides. The rodent species utilized will generally be a mouse. Of course, where a beta subunits is prepared which incorporates structural variations over the ones disclosed herein, it will likely be able to successfully employ a hybridoma system according to the species of interest.

In addition, the present invention provides a method for isolating beta subunits from other species which may be found antigenically cross-reactive with that of the human or rodent subunit. This method includes preparing an immunoabsorbent material having attached thereto an antibody to the subunit. Numerous immunoabsorbent materials are known to those skilled in the art and include, for example, Affi-Gel, Cn-Sepharose, protein A=Sepharose, and numerous other well know immunoadsorbent techniques. All such techniques of the immuno cross-reactive species (for a more complete listing, see *Monoclonal Hybridoma Antibodies: Techniques and Applications,* John G. Hurrell, ed. CRC Press, 1982, incorporated herein by reference).

Materials and Methods
Screening of cDNA and genomic libraries

The human basophil cDNA library and the human leukocytes genomic library have been described before and are available (Kuster, 1990). The human lung CDNA library (Miller, 1989) and a human skin cDNA library were provided by L.B. Schwartz (Medical College of Virginia, Richmond).

The following probes were prepared for screening the various libraries: The EcoRI-EcoRV fragment of rat β (Kinet, 1988) and the EcoRI fragment of mouse β (Ra, 1989), both of which contain the entire coding sequence of β and part of the 3' untranslated region. Fragments of the coding region of rat β cDNA (bp 1–304) and mouse β cDNA (bp 433–708) were made by polymerase chain reaction (PCR). Multiple oligonucleotides corresponding to various regions of rat, mouse and human β were synthesized on a model 380A automated DNA synthesizer (Applied Biosystems, Foster City, Calif.). All double stranded DNA probes were radiolabeled by random primer labeling and the oligonucleotides by end labeling as described elsewhere (Davis, 1986).

Hybridization and washing conditions and procedures for plaque purification subcloning, sequencing and DNA analysis were as described previously (Kuster, 1990).

Southern blot analysis

Digestion of genomic DNA from five different individuals with BamH BgI II, Eco RI, Hind III, Msp I and Pvu II and hybridization of these digests with a human CDNA probe (from start to stop codon) supports the existence of a unique gene (FIG. 18). In addition the lengths of the restriction fragments detected on the southern blot are entirely consistent with the lengths predicted from the sequence of the gene. Three BamHI sites (nucleotide 156, 6908, 9250) are presenting the gene. As expected only one fragment (156–9250) is seen here because the other fragments should not hybridize with the cDNA probe. The two predicted Bgl II fragments (+334 to +1766 and +1766 to +7419) and the two predicted Hind III fragments (−454 to +2724 and +2724 to 100042) are readily detected. The results obtained after EcoRI and PvuII digestions are consistent the fact that none of these sites are found in the sequence of the gene. Finally the pattern observed after Msp I digestion is also consistent with predicted fragments of 2067 bp, 3870 bp and a larger 5' fragment extending from nucleotide 3622 to an undetermined Mspl site upstream of the gene.

cDNA synthesis by using the Polymerase Chain Reaction (PCR)

Basophils from 240 ml of blood were purified by double Percoll gradients as previously described (Warner, 1987) and basophil RNA extracted by the guanidium isothiocyanate method (Davis, 1986). Two μg of total RNA were reverse transcribed with Superscript reverse transcriptase using a random 9-mer primer as recommended by the manufacturer (Bethesda Research Laboratories, Gaithersburg Md.). One twentieth of the reaction product was amplified using the following primers: a 23-mer complementary to nucleotide −2 to +21 of the human β coding sequence and as backward primer a degenerated 21-mer of the mouse and rat β sequences starting 32 nucleotides after the stop codon. Temperature cycles were as follows: 1 cycle of 2 min. 95°/2 min. 94°/5 min. 37°/40 min. 72°, 4 cycles of 40 sec. 94°/1 min. 37°/4 min. 72°, and 36 cycles of 40 sec. 94°/1 min. 50°/4 min. 72° followed by a single 15 minute extension. One μl of this reaction was reamplified omitting cycles 2 to 5 and the amplification product subcloned into pCR1000 using the TA cloning kit (Invitrogen, San Diego, Calif.).

Direct sequencing of gene fragments obtained by PCR

Purified insert-containing phage DNA from the leukocyte genomic library was linearized with NotI and 100 ng amplified with primers flanking the region to be sequenced. DNA amplification was achieved using 40 of the following cycles: denaturation for 1 min. at 94° C., annealing or 2 min. at 45°–50° C. and extension for 3–6 min. at 72° C. Subsequently 1 μl of the amplified material was reamplified in three separate reactions (50 μl) Under identical conditions omitting one of the 2 primers in order to generate single stranded DNA. The three reactions were pooled, applied to an Ultrafree MC 30.000 spin column (Millipore, Bedford Mass.), and washed four times before being evaporated by vacuum. The single stranded DNA was sequenced by using the omitted primer or an internal primer. The comparison of sequences obtained by this method or by sequencing non amplified fragments being subcloned in pGEM vectors revealed no differences.

Sequencing the transcription start site

PCR was used to define the transcription start site. Procedures published elsewhere (Frohman, 1987) were modified as follows: 5 μg RNA were reverse transcribed as detailed above by using a primer corresponding to nucleotide +451 to 429 of the coding region. The resulting product was washed on a Centricon 100 column (Amicon, Beverly Mass.) and a poly-A tails were at both ends addedusing terminal transferase (Bethesda Research Laboratories, Gaithersburg Md.) as recommended by the manufacturer. One sixth of this reaction was amplified with the following 2 primers: a 33-mer consisting of the M13 primer sequence followed by 17 T's and for the 3' end a primer derived from nucleotide 331 to 308 of the human β coding region sequence. Subsequently an internal amplification was performed exchanging the 3' primer for one equivalent to nucleotide +189 to 169. Finally, single stranded DNA was produced for sequencing by using an oligonucleotide corresponding to nucleotide 54 to 33 as the only primer. For all PCR's the annealing temperature was 45° C., the extension time 3 min.

Analysis of the transcription start site by 5' extension

An end labeled oligonucleotide corresponding to the negative strand at nucleotide 54 to 33 after the start codon was hybridized overnight at 42° C. to either 10 μg total RNA from enriched basophils or 10 μg tRNA, followed by extension with Superscript reverse transcriptase (Bethesda Research Laboratories, Gaithersburg Md.) at 45° C. for 90 min. The primer-extended products were separated on a 5% polyacrylamide urea gel in parallel with the sequencing reactions of the genomic DNA.

Cell Line KU812

A new myeloid cell line (KU812) was established from a patient with blastic crisis of chronic myelogenous leukemia. His blasts were morphologically characteristic of immature basophils and basophil colonies were grown in agar culture of the blood mononuclear cells. Suspension culture of his blood cells was continue for more than 2.5 years. The KU812 cells morphologically showed a fine reticular nuclei with nucleoli, and some of them contained metachromatic granules with toluidine blue (TB) staining. These granules were positive for astra blue (AB) staining. Immunological marker studies revealed that there were no lymphoid characters except Fc receptors. The KU812 cells grew colonies in in vitro agar cultures, which were proved to be composed of basophils by TB staining and AB staining. Cytogenetic analysis showed marked aneuploidy and was positive for the Philadelphia chromosome ($Ph^1$). The cell lysate was proved to contain histamine. These data suggest that KU812 is a cell line from leukemic basophil precursors. This is the first human basophil cell line. KU812 is useful in clarifying the mechanism of basophilic differentiation of the stem cells. (Kishi, Leuk, Res, 1985, a: 381–390).

Other methods

Northern and Genomic Southern blots were performed as described elsewhere (Davis, 1986). The various cDNAs were subcloned into the eukaryotic expression vector pCDL-SR(α) for the transfection studies (Takebe, 1988). COS-7 cells were transfected by the standard DEAE-Dextran method (Maniatis, 1982), except that a 3 minute incubation of the transfected cells in 10% DMSO in media as added after the chloroquine treatment.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

REFERENCES

The references listed below are incorporated herein by reference to the extent that they supplement, explain, provide a background for, or teach methodology, techniques and/or compositions employed herein.

1. Adamczewski et al., Evidence for two distinct kinase/phosphatase pathways in the activation of receptors coupled to non-receptor-kinases, in press)
2. Alberts et al, Molecular Biology of the Cell, 1983, pp. 179–180.
3. Baranes and Razin, Blood, 78: 2354–2364 (1991), Collaborative Biomedical Products, Becton-Dickinson, Catalog No. 30032, lot 904092, Mouse Interleukin-2 ELISA kit.
4. Blank, U., Ra C., Miller, L., White, K., Metzger, H., and Kinet, J. P. (1989) Nature 337, 187–189.
5. Davis, L. G., Dibner, M. D., and Battey, J. F. (1986) Basic Methods in Molecular Biology, Elsevier Science Publishing Co., New York
6. Frohman, M. A., Dush, M. K., and Martin, G. R. (1988) Proc. Natl. Acad. Sci. 85, 8999–9002
7. Huppi, K., Siwarski, D., Mock, B. A., and Kinet, J. P. (1989) J. Immunol. 143, 3787–3791.
8. Huppi, J., Mock, B.A., Hilgers, J. Kochan, J., and Kinet, J. P. (1988) J. Immunol. 141, 2807–2810.
9. Kinet, J. P., Blank, U., Ra, C., White, K., Metzger, H., and Kochan, J. (1988) Proc. Natl. Acad. Sci. U.S.A. 85, 6483–6487.
10. Kinet, J. P. (1990) Curr. Opinion Immunology 2, 499–505.
11. Kinet, J. P., Metzger, H., Hakimi, J., and Kochan, J. (1987) Biochemistry 26, 4605–4610.
12. Kochan, J., Pettine, L. F., Hakimi, J., Kisshi, J., and Kinet, J. P. (1988) Nucleic Acids Res 16, 3584–3594
13. Kuster, H., Thompson, H., and Kinet, J. P. (1990) J. Biol. Chem. 265, 6448–6452.
14. Le Coniat, M., Kinet, J. P., and Berger, R. (1990) Immunogenetics 32, 183–186.
15. Letourneu, O., Kennedy, I. C. S., Brini, A. T., Ortaldo, J. R., O'Shea, J. J. and Kinet, J. P. (1991) J. Immunol. in press
16. Liu, F. T., Albrandt, K., and Robertson, M. W. (1988) Proc. Natl. Acad. Sci. U.S.A. 85, 5639–5643.
17. Maniatis, T., Fritsch, E. F., & Sambrook, J. (1982) Molecular Cloning, a Laboratory Manual, Cold Spring Harbor Laboratory, Cold Spring Harbor, N.Y.
18. Miller, J. S., Westin, E. H., and Schwartz, L. B. (1989) J. Clin. Invest. 84, 1188–1195
19. Miller, L., Blank, U., Metzger, H. and Kinet,J. P. (1989) Science 244, 334–337
20. Orloff, D. G., Ra. C., Frank, S. J., Klausner, R. D., and Kinet, J. P. (1990) Nature 347, 189–191.
21. Ra, C., Jouvin, M. H. E., and Kinet, J. P. (1989) J. Biol. Chem 264, 15323–15327.
22. Ra, C., Jouvin, M. H. E., Blank, U., and Kinet, J. P. (1989) Nature 341, 752–754
23. Ravetch J. V. and Kinet, J. P. (1991) Ann. Rev. Immunol. 9, 457–492.
24. Shimizu, A., Tepler, I., Benfey, P. N., Berenstein, E. H., Siraganian, R. P., and Leder, P. (1988) Proc. Natl. Acad. Sci. U.S.A. 85, 1907–1911.
25. Takebe, Y., Seiki, M., Fujisawa, J.-I., Hoy, P., Yokota, K., Arai, K.-I., Yoshida, M., Arai, N. (1988) Mol. Cell. Biol. 8, 466–472
26. Tepler, I., Shimizu, A., and Leder, P. (1989) J. Biol. Chem. 264, 5912–5915.
27. Varin-Blank, N., Metzger, H. (1990) Expression of mutated subunits of the high effinity Mast cell receptor for IgE. J. Biol. Chem.
28. Warner, J. A., Reshef, A., and MacGlashan, D. W. J. (1987) J. Immunol. Methods 105, 107–110

What is claimed is:

1. An isolated nucleic acid molecule encoding a human beta subunit of Fc$_\epsilon$RI, said beta subunit having an amino acid sequence as shown in Seq. I.D. No. 32.

2. The nucleic acid molecule of claim 1 wherein said molecule comprises a nucleotide sequence as shown in SEQ. I.D. No. 31.

3. A recombinant vector including a nucleic acid molecule according to claim 1.

4. A transgenic cell produced by introducing into a cell a vector according to claim 3.

5. A cell according to claim 4 wherein the cell is a bacterial cell.

6. A cell according to claim 4 wherein the cell is a eukaryotic cell.

7. A cell according to claim 6 wherein the cell is a mammalian cell.

8. A method of producing a human beta subunit of Fc$_\epsilon$RI, the method comprising growing a cell according to claim 4 under conditions whereby the nucleic acid molecule is expressed, resulting in the synthesis of said beta subunit in the cell.

9. The method of claim 8 further comprising purifying the beta subunit from the cell.

10. A method of expressing a functional human Fc$_\epsilon$RI in a host cell, comprising introducing into a host cell capable of expressing α and γ subunits of Fc$_\epsilon$RI, a nucleic acid molecule according to claim 1 and culturing the cell under conditions whereby a functional human Fc$_\epsilon$RI is expressed.

11. A method of expressing a functional human Fc$_\epsilon$RI in a host cell, comprising introducing into the host cell nucleic acid molecules encoding (a) the α subunit of human Fc$_\epsilon$RI;

(b) the β subunit of human Fc$_\epsilon$RI; and (c) the β subunit of human Fc$_\epsilon$RI wherein said β subunit is encoded by a nucleic acid molecule according to claim 1.

12. An isolated nucleic acid molecule including at least 14 contiguous nucleotides of the sequence shown in Seq. I.D. No. 2, or the complement of said sequence.

13. A recombinant vector including a nucleic acid molecule according to claim 12.

14. A transgenic cell produced by introducing into a cell a vector according to claim 13.

15. An isolated nucleic acid molecule including at least 22 contiguous nucleotides of the sequence shown in Seq. I.D. No. 2, or the complement of said sequence.

16. A recombinant vector including a nucleic acid molecule according to claim 15.

17. A transgenic cell produced by introducing into a cell a vector according to claim 16.

18. An isolated nucleic acid molecule encoding a human beta subunit of Fc$_\epsilon$RI, wherein said molecule comprises a human nucleotide sequence as shown in Seq. I.D. No. 31 or an allelic variant of said sequence.

19. A recombinant vector including a nucleic acid molecule according to claim 18.

20. A transgenic cell produced by introducing into a cell a vector according to claim 19.

* * * * *

UNITED STATES PATENT AND TRADEMARK OFFICE
CERTIFICATE OF CORRECTION

PATENT NO.    : 5,770,396
DATED         : June 23, 1996
INVENTOR(S)   : Kinet

It is certified that error appears in the above-identified patent and that said Letters Patent is hereby corrected as shown below:

Title page,
Item [56], References Cited, OTHER PUBLICATIONS,
Kurosaki, et al. publication: "75:447-451" should be -- 175:447-451 --

Column 1,
Line 46, "y gene" should be -- γ gene --

Column 6,
Line 23, "PHAII)" should be -- pHAII) --
Line 25, "The last sentence in Fig. 3 should be located at the end of the Fig. 4. paragraph. Fig. 3 should read as follows:
-- FIG. 3. A flow chart showing the construction of eukaryotic expression vectors which direct the synthesis of a complete biologically active FcϵRI alpha chain (pHAI, pHAII) or a soluble, secreted, biologically active FcϵRl alpha chain (pHASI, pHASII) is presented. The sequence shown in this Figure is also disclosed in SEQ ID NO:20. --
Line 27, the last sentence of Fig. 4 should read:
-- The sequences shown in the pEVA construct are also shown in SEQ ID NOs: 15-17; the sequences shown in the EVHA construct are also shown in SEQ ID NOs: 18 and 19; the sequences shown in the pEVHAS construct are also shown in SEQ ID NOs: 20 and 21. --
Line 27, "EVHA" should read -- pEVHA --

Column 7,
Line 19, "B subunit" should read -- β subunit --
Line 25, "mAbB" should read -- mABB --

Column 8,
Line 12, "resetting" should read -- ro setting --
Line 19, "a subunit" should read -- α subunit --

Column 9,
Line 61, "respectively or" should read -- respectively) or --

Column 10,
Line 7, "*E coli*" should read -- E. Coli --
Line 54, "222.778" should read -- 222,778 --
Line 63, "Fc$\epsilon$RI $_{alpha\ cDNA\ corresponding\ to\ nucleotides}$" should read -- FcϵRI alpha cDNA corresponding to nucleotides --

UNITED STATES PATENT AND TRADEMARK OFFICE
CERTIFICATE OF CORRECTION

PATENT NO.   : 5,770,396
DATED        : June 23, 1996
INVENTOR(S)  : Kinet

It is certified that error appears in the above-identified patent and that said Letters Patent is hereby corrected as shown below:

Column 11,
Line 11, "FIG. 1 SEQ ID NO:10." should read -- FIG. 1 and SEQ ID NO: 10. --
Line 18, "137.17" should read -- 137,17 --
Line 28, "(FIG. 2). SEQ ID NOs: 12-14." should read -- (FIG. 2 and SEQ ID NOs 12-14). --
Line 47, "152." should read -- 152, --

Column 12,
Line 11, "Enzymology." should read -- Enzymology, --
Line 25, "Prokarvotic" should read -- Prokaryotic --
Line 47, "FC∈RI" should read -- Fc∈RI --
Line 50, "(SEQ ID NO:3." should read -- (SEQ ID NO:3) --

Column 13,
Line 13, "Fe∈Rl" should read --Fc∈Rl --

Column 14,
Line 36, "transcriDtion" should read -- transcription --
Line 57, "e al." should read -- et al. --

Column 15,
Line 11, "(JRk)" should read -- (JRK) --
Line 11, "mAbB" should read -- mAbβ --
Lines 18 and 20, "in vitro" should read -- *in vitro* --
Line 20, "in vivo" should read -- *in vivo* --
Line 28, "In vitro" should read -- *In vitro* --

Column 16,
Line 3, "mAvB" should read -- mAbβ --
Line 9, "$^{125}$-labled" should read -- $^{125}$I-labeled --

Column 17,
Line 21, "CDNA" should be -- cDNA --

Column 18,
Line 42, " β fragment" should read -- β1 fragment --
Line 47, "the 8" should read -- the β --
Line 57, "from 8" should read -- from β --

UNITED STATES PATENT AND TRADEMARK OFFICE
CERTIFICATE OF CORRECTION

PATENT NO. : 5,770,396
DATED : June 23, 1996
INVENTOR(S) : Kinet

It is certified that error appears in the above-identified patent and that said Letters Patent is hereby corrected as shown below:

Column 19,
Line 35, "47 SEQ" should read -- 47 of SEQ --
Line 36, "62)." should read -- 62 of SEQ ID NO: 27). --
Line 37, "A and" should read -- A (SEQ ID NO: 8) and --
Line 38, "(A/G) GA" should read -- (A/G)GA --
Line 63, "FC∈RI" should read -- Fc∈RI --

Column 20,
Line 53, "PSVL" should read -- pSVL --
Line 59, "PSVL" should read -- pSVL --

Column 21,
Line 4, "5×106" should read -- $5 \times 10^6$ --
Line 19, "Ned." should read -- Med. --
Line 27, "resetting" should read -- rosetting --

Column 22,
Line 6, "FC$_\epsilon$RI" should read -- Fc$_\epsilon$RI- --
Line 10, "Fc∈RI" should read -- Fc$_\epsilon$RI --
Line 15, "$_\alpha\beta$y2" should read -- $_\alpha\beta y_2$ --
Line 28, "The $_\alpha$(SEQ ID NO:28) chain" should read -- The α chain (SEQ ID NO:28) --

Column 23,
Line 50, "Not" should read -- No. --

Column 24,
Line 8, "FcyRappears" should read --FcyR appears --
Line 64, "Fc$_{68}$RI" should read -- Fc$_\epsilon$RI --

Column 26,
Line 63, "(FIG. 14) and SEQ ID NO:31" should read -- FIG. 14 A-Q and SEQ ID NO:31).

Column 27,
Line 28, "B" should read -- β --

UNITED STATES PATENT AND TRADEMARK OFFICE
CERTIFICATE OF CORRECTION

PATENT NO. : 5,770,396
DATED : June 23, 1996
INVENTOR(S) : Kinet

It is certified that error appears in the above-identified patent and that said Letters Patent is hereby corrected as shown below:

Column 28,
Line 23, "FIG. 14, SEQ" should read -- FIG. 14 A-Q, SEQ --

Column 29,
Line 13, "FC$\epsilon$RI" should read -- Fc$\epsilon$RI --

Line 40, "$\beta$" should read -- y --
Line 42, "y" should read -- $\beta$ --
Line 42, "y" should read -- $\beta$ --

Column 33,
Line 5, "CDNA" should read -- cDNA --
Line 29, "CDNA" should read -- cDNA --

Column 80,
Line 9, "the $\beta$ subunit" should read -- the y subunit --
Line 15, "2" should read -- 31 --
Line 23, "2" should read -- 31 --

Signed and Sealed this

First Day of April, 2003

JAMES E. ROGAN
*Director of the United States Patent and Trademark Office*

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

AAGTACTGGC TATGATTTTT TATCCCATTG      30

( 2 ) INFORMATION FOR SEQ ID NO:2:

( i ) SEQUENCE CHARACTERISTICS:
      ( A ) LENGTH: 38 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:2:

GAATTAATAT GGTCCCTCAG AAACCTAAGG TCTCCTTG                                          38

( 2 ) INFORMATION FOR SEQ ID NO:3:

( i ) SEQUENCE CHARACTERISTICS:
      ( A ) LENGTH: 30 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:3:

AAGTACTGGC TATGATTTTT TATCCCATTG                                                   30

( 2 ) INFORMATION FOR SEQ ID NO:4:

( i ) SEQUENCE CHARACTERISTICS:
      ( A ) LENGTH: 17 amino acids
      ( B ) TYPE: amino acid
      ( D ) TOPOLOGY: linear ( x i ) SEQUENCE DESCRIPTION: SEQ ID NO:4:

Tyr Glu Glu Leu His Val Tyr Ser Pro Ile Tyr Ser Ala Leu Glu Asp
1               5                   10                  15

Thr ( 2 ) INFORMATION FOR SEQ ID NO:5:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i x ) FEATURE:
      ( A ) NAME/KEY: misc_feature
      ( B ) LOCATION: 3
      ( D ) OTHER INFORMATION: /note= "N in this sequence
            represents inosine"

( i x ) FEATURE:
      ( A ) NAME/KEY: misc_feature
      ( B ) LOCATION: 15
      ( D ) OTHER INFORMATION: /note= "N in this sequence
            represents inosine"

( x i ) SEQUENCE DESCRIPTION: SEQ ID NO:5:

GGNGARTASA CATGNARYTC YTCATA                                                       26

( 2 ) INFORMATION FOR SEQ ID NO:6:

( i ) SEQUENCE CHARACTERISTICS:
      ( A ) LENGTH: 26 base pairs
      ( B ) TYPE: nucleic acid
      ( C ) STRANDEDNESS: single
      ( D ) TOPOLOGY: linear ( i x ) FEATURE:
      ( A ) NAME/KEY: misc_feature
      ( B ) LOCATION: 3
      ( D ) OTHER INFORMATION: /note= "N in this sequence
            represents inosine"

-continued (ix) FEATURE:
　　　　(A) NAME/KEY: misc_feature
　　　　(B) LOCATION: 15
　　　　(D) OTHER INFORMATION: /note= "N in this sequence
　　　　　　represents inosine"

(xi) SEQUENCE DESCRIPTION: SEQ ID NO:6:

GGNCTRTASA CATGNARYTC YTCATA　　　　　　　　　　　　　　　　26

(2) INFORMATION FOR SEQ ID NO:7:

(i) SEQUENCE CHARACTERISTICS:
　　　　(A) LENGTH: 23 base pairs
　　　　(B) TYPE: nucleic acid
　　　　(C) STRANDEDNESS: single
　　　　(D) TOPOLOGY: linear (xi) SEQUENCE DESCRIPTION: SEQ ID NO:7:

AATAAAACAA AAAAAAAAA ATG　　　　　　　　　　　　　　　　　　23

(2) INFORMATION FOR SEQ ID NO:8:

(i) SEQUENCE CHARACTERISTICS:
　　　　(A) LENGTH: 20 base pairs
　　　　(B) TYPE: nucleic acid
　　　　(C) STRANDEDNESS: single
　　　　(D) TOPOLOGY: linear (ix) FEATURE:
　　　　(A) NAME/KEY: misc_feature
　　　　(B) LOCATION: 9
　　　　(D) OTHER INFORMATION: /note= "N in this sequence
　　　　　　represents inosine"

(xi) SEQUENCE DESCRIPTION: SEQ ID NO:8:

GARAARTCNG AYGCTCTCTA　　　　　　　　　　　　　　　　　　　20

(2) INFORMATION FOR SEQ ID NO:9:

(i) SEQUENCE CHARACTERISTICS:
　　　　(A) LENGTH: 26 base pairs
　　　　(B) TYPE: nucleic acid
　　　　(C) STRANDEDNESS: single
　　　　(D) TOPOLOGY: linear (ix) FEATURE:
　　　　(A) NAME/KEY: misc_feature
　　　　(B) LOCATION: 12
　　　　(D) OTHER INFORMATION: /note= "N in this sequence
　　　　　　represents inosine"

(ix) FEATURE:
　　　　(A) NAME/KEY: misc_feature
　　　　(B) LOCATION: 21
　　　　(D) OTHER INFORMATION: /note= "N in this sequence
　　　　　　represents inosine"

(ix) FEATURE:
　　　　(A) NAME/KEY: misc_feature
　　　　(B) LOCATION: 24
　　　　(D) OTHER INFORMATION: /note= "N in this sequence
　　　　　　represents inosine"

(xi) SEQUENCE DESCRIPTION: SEQ ID NO:9:

AAYCARGARA CNTAYGARAC NYTNAA　　　　　　　　　　　　　　　26

(2) INFORMATION FOR SEQ ID NO:10:

(i) SEQUENCE CHARACTERISTICS:
　　　　(A) LENGTH: 1174 base pairs
　　　　(B) TYPE: nucleic acid
　　　　(C) STRANDEDNESS: double ( D ) TOPOLOGY: linear ( i i ) MOLECULE TYPE: cDNA ( i x ) FEATURE:
    ( A ) NAME/KEY: CDS
    ( B ) LOCATION: 107..880

( x i ) SEQUENCE DESCRIPTION: SEQ ID NO:10:

```
TACTAAGAGT CTCCAGCATC CTCCACCTGT CTACCACCGA GCATGGGCCT ATATTTGAAG        60

CCTTAGATCT CTCCAGCACA GTAAGCACCA GGAGTCCATG AAGAAG ATG GCT CCT          115
                                                   Met Ala Pro
                                                    1

GCC ATG GAA TCC CCT ACT CTA CTG TGT GTA GCC TTA CTG TTC TTC GCT         163
Ala Met Glu Ser Pro Thr Leu Leu Cys Val Ala Leu Leu Phe Phe Ala
     5              10              15

CCA GAT GGC GTG TTA GCA GTC CCT CAG AAA CCT AAG GTC TCC TTG AAC         211
Pro Asp Gly Val Leu Ala Val Pro Gln Lys Pro Lys Val Ser Leu Asn
 20              25              30              35

CCT CCA TGG AAT AGA ATA TTT AAA GGA GAG AAT GTG ACT CTT ACA TGT         259
Pro Pro Trp Asn Arg Ile Phe Lys Gly Glu Asn Val Thr Leu Thr Cys
             40              45              50

AAT GGG AAC AAT TTC TTT GAA GTC AGT TCC ACC AAA TGG TTC CAC AAT         307
Asn Gly Asn Asn Phe Phe Glu Val Ser Ser Thr Lys Trp Phe His Asn
             55              60              65

GGC AGC CTT TCA GAA GAG ACA AAT TCA AGT TTG AAT ATT GTG AAT GCC         355
Gly Ser Leu Ser Glu Glu Thr Asn Ser Ser Leu Asn Ile Val Asn Ala
         70              75              80

AAA TTT GAA GAC AGT GGA GAA TAC AAA TGT CAG CAC CAA CAA GTT AAT         403
Lys Phe Glu Asp Ser Gly Glu Tyr Lys Cys Gln His Gln Gln Val Asn
     85              90              95

GAG AGT GAA CCT GTG TAC CTG GAA GTC TTC AGT GAC TGG CTG CTC CTT         451
Glu Ser Glu Pro Val Tyr Leu Glu Val Phe Ser Asp Trp Leu Leu Leu
100             105             110                             115

CAG GCC TCT GCT GAG GTG GTG ATG GAG GGC CAG CCC CTC TTC CTC AGG         499
Gln Ala Ser Ala Glu Val Val Met Glu Gly Gln Pro Leu Phe Leu Arg
             120             125                             130

TGC CAT GGT TGG AGG AAC TGG GAT GTG TAC AAG GTG ATC TAT TAT AAG         547
Cys His Gly Trp Arg Asn Trp Asp Val Tyr Lys Val Ile Tyr Tyr Lys
             135             140                 145

GAT GGT GAA GCT CTC AAG TAC TGG TAT GAG AAC CAC AAC ATC TCC ATT         595
Asp Gly Glu Ala Leu Lys Tyr Trp Tyr Glu Asn His Asn Ile Ser Ile
         150             155                 160

ACA AAT GCC ACA GTT GAA GAC AGT GGA ACC TAC TAC TGT ACG GGC AAA         643
Thr Asn Ala Thr Val Glu Asp Ser Gly Thr Tyr Tyr Cys Thr Gly Lys
     165             170                 175

GTG TGG CAG CTG GAC TAT GAG TCT GAG CCC CTC AAC ATT ACT GTA ATA         691
Val Trp Gln Leu Asp Tyr Glu Ser Glu Pro Leu Asn Ile Thr Val Ile
180             185                 190                         195

AAA GCT CCG CGT GAG AAG TAC TGG CTA CAA TTT TTT ATC CCA TTG TTG         739
Lys Ala Pro Arg Glu Lys Tyr Trp Leu Gln Phe Phe Ile Pro Leu Leu
             200             205                             210

GTG GTG ATT CTG TTT GCT GTG GAC ACA GGA TTA TTT ATC TCA ACT CAG         787
Val Val Ile Leu Phe Ala Val Asp Thr Gly Leu Phe Ile Ser Thr Gln
             215             220                 225

CAG CAG GTC ACA TTT CTC TTG AAG ATT AAG AGA ACC AGG AAA GGC TTC         835
Gln Gln Val Thr Phe Leu Leu Lys Ile Lys Arg Thr Arg Lys Gly Phe
         230             235                 240

AGA CTT CTG AAC CCA CAT CCT AAG CCA AAC CCC AAA AAC AAC TGATATAATT     887
Arg Leu Leu Asn Pro His Pro Lys Pro Asn Pro Lys Asn Asn
245                 250                 255
```

```
ACTCAAGAAA  TATTTGCAAC  ATTAGTTTTT  TTCCAGCATC  AGCAATTGCT  ACTCAATTGT        947

CAAACACAGC  TTGCAATATA  CATAGAAACG  TCTGTGCTCA  AGGATTTATA  GAAATGCTTC       1007

ATTAAACTGA  GTGAAACTGG  TTAAGTGGCA  TGTAATAGTA  AGTGCTCAAT  TAACATTGGT       1067

TGAATAAATG  AGAGAATGAA  TAGATTCATT  TATTAGCATT  GTAAAGAGA   TGTTCAATTT       1127

CAATAAAATA  AATATAAAAC  CATGTAAAAA  AAAAAAAAAA  AAAAAA                       1174
```

( 2 ) INFORMATION FOR SEQ ID NO:11:

( i ) SEQUENCE CHARACTERISTICS:
        ( A ) LENGTH: 257 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met  Ala  Pro  Ala  Met  Glu  Ser  Pro  Thr  Leu  Leu  Cys  Val  Ala  Leu  Leu
 1                    5                      10                      15

Phe  Phe  Ala  Pro  Asp  Gly  Val  Leu  Ala  Val  Pro  Gln  Lys  Pro  Lys  Val
               20                      25                      30

Ser  Leu  Asn  Pro  Pro  Trp  Asn  Arg  Ile  Phe  Lys  Gly  Glu  Asn  Val  Thr
          35                      40                      45

Leu  Thr  Cys  Asn  Gly  Asn  Asn  Phe  Phe  Glu  Val  Ser  Ser  Thr  Lys  Trp
     50                      55                      60

Phe  His  Asn  Gly  Ser  Leu  Ser  Glu  Glu  Thr  Asn  Ser  Ser  Leu  Asn  Ile
 65                      70                      75                      80

Val  Asn  Ala  Lys  Phe  Glu  Asp  Ser  Gly  Glu  Tyr  Lys  Cys  Gln  His  Gln
                    85                      90                      95

Gln  Val  Asn  Glu  Ser  Glu  Pro  Val  Tyr  Leu  Glu  Val  Phe  Ser  Asp  Trp
               100                     105                     110

Leu  Leu  Leu  Gln  Ala  Ser  Ala  Glu  Val  Val  Met  Glu  Gly  Gln  Pro  Leu
          115                     120                     125

Phe  Leu  Arg  Cys  His  Gly  Trp  Arg  Asn  Trp  Asp  Val  Tyr  Lys  Val  Ile
     130                     135                     140

Tyr  Tyr  Lys  Asp  Gly  Glu  Ala  Leu  Lys  Tyr  Trp  Tyr  Glu  Asn  His  Asn
145                      150                     155                     160

Ile  Ser  Ile  Thr  Asn  Ala  Thr  Val  Glu  Asp  Ser  Gly  Thr  Tyr  Tyr  Cys
                    165                     170                     175

Thr  Gly  Lys  Val  Trp  Gln  Leu  Asp  Tyr  Glu  Ser  Glu  Pro  Leu  Asn  Ile
               180                     185                     190

Thr  Val  Ile  Lys  Ala  Pro  Arg  Glu  Lys  Tyr  Trp  Leu  Gln  Phe  Phe  Ile
          195                     200                     205

Pro  Leu  Leu  Val  Val  Ile  Leu  Phe  Ala  Val  Asp  Thr  Gly  Leu  Phe  Ile
     210                     215                     220

Ser  Thr  Gln  Gln  Gln  Val  Thr  Phe  Leu  Leu  Lys  Ile  Lys  Arg  Thr  Arg
225                      230                     235                     240

Lys  Gly  Phe  Arg  Leu  Leu  Asn  Pro  His  Pro  Lys  Pro  Asn  Pro  Lys  Asn
                    245                     250                     255

Asn
```

( 2 ) INFORMATION FOR SEQ ID NO:12:

( i ) SEQUENCE CHARACTERISTICS:
        ( A ) LENGTH: 222 amino acids
        ( B ) TYPE: amino acid
        ( D ) TOPOLOGY: linear ( i i ) MOLECULE TYPE: protein ( v i ) ORIGINAL SOURCE:
    ( A ) ORGANISM: Rat
    ( B ) STRAIN: FcRI alpha subunit ( x i ) SEQUENCE DESCRIPTION: SEQ ID NO:12:

```
Ala Thr Gln Lys Ser Val Val Ser Leu Asp Pro Pro Trp Ile Arg Ile
 1               5                  10                  15

Leu Thr Gly Asp Lys Val Thr Leu Ile Cys Asn Gly Asn Asn Ser Ser
                20                  25                  30

Gln Met Asn Ser Thr Lys Trp Ile His Asn Asp Ser Ile Ser Asn Val
            35                  40                  45

Lys Ser Ser His Trp Val Ile Val Ser Ala Thr Ile Gln Asp Ser Gly
        50                  55                  60

Lys Tyr Ile Cys Gln Lys Gln Gly Phe Tyr Lys Ser Lys Pro Val Tyr
 65                  70                  75                  80

Leu Asn Val Met Gln Glu Trp Leu Leu Leu Gln Ser Ser Ala Asp Val
                85                  90                  95

Val Leu Asp Asn Gly Ser Phe Asp Ile Arg Cys Arg Ser Trp Lys Lys
            100                 105                 110

Trp Lys Val His Lys Val Ile Tyr Tyr Lys Asp Asp Ile Ala Phe Lys
        115                 120                 125

Tyr Ser Tyr Asp Ser Asn Asn Ile Ser Ile Arg Lys Ala Thr Phe Asn
    130                 135                 140

Asp Ser Gly Ser Tyr His Cys Thr Gly Tyr Leu Asn Lys Val Glu Cys
145                 150                 155                 160

Lys Ser Asp Lys Phe Ser Ile Ala Val Val Lys Asp Tyr Thr Ile Glu
                165                 170                 175

Tyr Arg Trp Leu Gln Leu Ile Phe Pro Ser Leu Ala Val Ile Leu Phe
            180                 185                 190

Ala Val Asp Thr Gly Leu Trp Phe Ser Thr His Lys Gln Phe Glu Ser
        195                 200                 205

Ile Leu Lys Ile Gln Lys Thr Gly Lys Gly Lys Lys Lys Gly
    210                 215                 220
```

( 2 ) INFORMATION FOR SEQ ID NO:13:

( i ) SEQUENCE CHARACTERISTICS:
        ( A ) LENGTH: 232 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: homo sapien
        ( B ) STRAIN: FcRI alpha subunit ( x i ) SEQUENCE DESCRIPTION: SEQ ID NO:13:

```
Val Pro Gln Lys Pro Lys Val Ser Leu Asn Pro Pro Trp Asn Arg Ile
 1               5                  10                  15

Phe Lys Gly Glu Asn Val Thr Leu Thr Cys Asn Gly Asn Asn Phe Phe
                20                  25                  30

Glu Val Ser Ser Thr Lys Trp Phe His Asn Gly Ser Leu Ser Glu Glu
            35                  40                  45

Thr Asn Ser Ser Leu Asn Ile Val Asn Ala Lys Phe Glu Asp Ser Gly
        50                  55                  60

Glu Tyr Lys Cys Gln His Gln Gln Val Asn Glu Ser Glu Pro Val Tyr
 65                  70                  75                  80
```

|     |     |     |     |     |     |     |     |     |     |     |     |     |     |     |     |
|-----|-----|-----|-----|-----|-----|-----|-----|-----|-----|-----|-----|-----|-----|-----|-----|
| Leu | Glu | Val | Phe | Ser<br>85 | Asp | Trp | Leu | Leu<br>90 | Gln | Ala | Ser | Ala | Glu<br>95 | Val |   |
| Val | Met | Glu | Gly<br>100 | Gln | Pro | Leu | Phe | Leu<br>105 | Arg | Cys | His | Gly | Trp<br>110 | Arg | Asn |
| Trp | Asp | Val<br>115 | Tyr | Lys | Val | Ile | Tyr<br>120 | Tyr | Lys | Asp | Gly | Glu<br>125 | Ala | Leu | Lys |
| Tyr | Trp<br>130 | Tyr | Glu | Asn | His | Asn<br>135 | Ile | Ser | Ile | Thr | Asn<br>140 | Ala | Thr | Val | Glu |
| Asp<br>145 | Ser | Gly | Thr | Tyr | Tyr<br>150 | Cys | Thr | Gly | Lys | Val<br>155 | Trp | Gln | Leu | Asp | Tyr<br>160 |
| Glu | Ser | Glu | Pro | Leu<br>165 | Asn | Ile | Thr | Val | Ile<br>170 | Lys | Ala | Pro | Arg | Glu<br>175 | Lys |
| Tyr | Trp | Leu | Gln<br>180 | Phe | Phe | Ile | Pro | Leu<br>185 | Leu | Val | Val | Ile | Leu<br>190 | Phe | Ala |
| Val | Asp | Thr<br>195 | Gly | Leu | Phe | Ile | Ser<br>200 | Thr | Gln | Gln | Gln | Val<br>205 | Thr | Phe | Leu |
| Leu | Lys<br>210 | Ile | Lys | Arg | Thr | Arg<br>215 | Lys | Gly | Phe | Arg | Leu<br>220 | Leu | Asn | Pro | His |
| Pro<br>225 | Lys | Pro | Asn | Pro | Lys<br>230 | Asn | Asn |   |   |   |   |   |   |   |   |

(2) INFORMATION FOR SEQ ID NO:14:

(i) SEQUENCE CHARACTERISTICS:
        (A) LENGTH: 227 amino acids
        (B) TYPE: amino acid
        (D) TOPOLOGY: linear (ii) MOLECULE TYPE: protein (vi) ORIGINAL SOURCE:
        (A) ORGANISM: mouse
        (B) STRAIN: FcRI alpha subunit (xi) SEQUENCE DESCRIPTION: SEQ ID NO:14:

|     |     |     |     |     |     |     |     |     |     |     |     |     |     |     |     |
|-----|-----|-----|-----|-----|-----|-----|-----|-----|-----|-----|-----|-----|-----|-----|-----|
| Ala<br>1 | Thr | Glu | Lys | Ser<br>5 | Val | Leu | Thr | Leu | Asp<br>10 | Pro | Pro | Trp | Ile | Arg<br>15 | Ile |
| Phe | Thr | Gly | Glu<br>20 | Lys | Val | Thr | Leu | Ser<br>25 | Cys | Tyr | Gly | Asn | Asn<br>30 | His | Leu |
| Gln | Met | Asn<br>35 | Ser | Thr | Thr | Lys | Trp<br>40 | Ile | His | Asn | Gly | Thr<br>45 | Val | Ser | Glu |
| Val | Asn<br>50 | Ser | Ser | His | Leu | Val<br>55 | Ile | Val | Ser | Ala | Thr<br>60 | Val | Gln | Asp | Ser |
| Gly<br>65 | Lys | Tyr | Ile | Cys | Gln<br>70 | Lys | Gln | Gly | Leu | Phe<br>75 | Lys | Ser | Lys | Pro | Val<br>80 |
| Tyr | Leu | Asn | Val | Thr<br>85 | Gln | Asp | Trp | Leu | Leu<br>90 | Leu | Gln | Thr | Ser | Ala<br>95 | Asp |
| Met | Ile | Leu | Val<br>100 | His | Gly | Ser | Phe | Asp<br>105 | Ile | Arg | Cys | His | Gly<br>110 | Trp | Lys |
| Asn | Trp | Asn<br>115 | Val | Arg | Lys | Val | Ile<br>120 | Tyr | Tyr | Arg | Asn | Asp<br>125 | His | Ala | Phe |
| Asn | Tyr<br>130 | Ser | Tyr | Glu | Ser | Pro<br>135 | Val | Ser | Ile | Arg | Glu<br>140 | Ala | Thr | Leu | Asn |
| Asp<br>145 | Ser | Gly | Thr | Tyr | His<br>150 | Cys | Lys | Gly | Tyr | Leu<br>155 | Arg | Gln | Val | Glu | Tyr<br>160 |
| Glu | Ser | Asp | Lys | Phe<br>165 | Arg | Ile | Ala | Val | Val<br>170 | Lys | Ala | Tyr | Lys | Cys<br>175 | Lys |

|  |  |  |  |  |  |  |  |  |  |  |  |  |  |  |
|---|---|---|---|---|---|---|---|---|---|---|---|---|---|---|
| Tyr | Tyr | Trp | Leu | Gln | Leu | Ile | Phe | Pro | Leu | Leu | Val | Ala | Ile | Leu | Phe |
|  |  |  | 180 |  |  |  |  | 185 |  |  |  |  | 190 |  |  |
| Ala | Val | Asp | Thr | Gly | Leu | Leu | Ser | Thr | Glu | Glu | Gln | Phe | Lys | Ser |
|  |  | 195 |  |  |  | 200 |  |  |  |  | 205 |  |  |  |
| Val | Leu | Glu | Ile | Gln | Lys | Thr | Gly | Lys | Tyr | Lys | Val | Glu | Thr | Glu |
|  | 210 |  |  |  |  | 215 |  |  |  |  | 220 |  |  |  |
| Leu | Leu | Thr |
| 225 |  |  |

(2) INFORMATION FOR SEQ ID NO:15:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 9..11

(ix) FEATURE:
        (A) NAME/KEY: CDS
        (B) LOCATION: 21..32

(xi) SEQUENCE DESCRIPTION: SEQ ID NO:15:

GAATTAAT ATG AATGAATTT AAG GTC TCC TTG    32
        Met           Lys Val Ser Leu
         1             1

(2) INFORMATION FOR SEQ ID NO:16:

(i) SEQUENCE CHARACTERISTICS:
        (A) LENGTH: 1 amino acids
        (B) TYPE: amino acid
        (D) TOPOLOGY: linear (ii) MOLECULE TYPE: protein (xi) SEQUENCE DESCRIPTION: SEQ ID NO:16:

Met
1

(2) INFORMATION FOR SEQ ID NO:17:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:17:

Lys Val Ser Leu
1

(2) INFORMATION FOR SEQ ID NO:18:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 9..38

(xi) SEQUENCE DESCRIPTION: SEQ ID NO:18:

```
GAATTAAT ATG GTC CCT CAG AAA CCT AAG GTC TCC TTG                                    38
         Met Val Pro Gln Lys Pro Lys Val Ser Leu
          1           5                    10
```

( 2 ) INFORMATION FOR SEQ ID NO:19:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met Val Pro Gln Lys Pro Lys Val Ser Leu
 1           5                    10
```

( 2 ) INFORMATION FOR SEQ ID NO:20:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i x ) FEATURE:
        ( A ) NAME/KEY: CDS
        ( B ) LOCATION: 1..15

( x i ) SEQUENCE DESCRIPTION: SEQ ID NO:20:

```
AAG TAC TGG CTA TGATTTTTA TCCCATTG                                                  30
Lys Tyr Trp Leu
 1           5
```

( 2 ) INFORMATION FOR SEQ ID NO:21:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Lys Tyr Trp Leu
 1
```

( 2 ) INFORMATION FOR SEQ ID NO:22:

( i ) SEQUENCE CHARACTERISTICS:
        ( A ) LENGTH: 2545 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 46..786

( i x ) FEATURE:
        ( A ) NAME/KEY: sig_peptide
        ( B ) LOCATION: 46..54

( i x ) FEATURE:
        ( A ) NAME/KEY: mat_peptide
        ( B ) LOCATION: 55..786

( x i ) SEQUENCE DESCRIPTION: SEQ ID NO:22:

```
ACGTTTCTGT GTAACAATAT CTTTTATTCC TGGATAGTCC AATTA ATG AAA AAA                       54
```

```
                                                          Met Lys Lys
                                                            -3

ATG GAC ACA GAA AAT AAG AGC AGA GCA GAT CTT GCT CTC CCA AAC CCA        102
Met Asp Thr Glu Asn Lys Ser Arg Ala Asp Leu Ala Leu Pro Asn Pro
 1           5                   10                  15

CAA GAA TCC CCC AGC GCA CCT GAC ATT GAA CTC TTG GAA GCG TCC CCT        150
Gln Glu Ser Pro Ser Ala Pro Asp Ile Glu Leu Leu Glu Ala Ser Pro
             20                  25                  30

CCT GCA AAA GCT CTA CCA GAG AAG CCA GCC TCA CCC CCA CAG CAG            198
Pro Ala Lys Ala Leu Pro Glu Lys Pro Ala Ser Pro Pro Gln Gln
         35                  40                  45

ACA TGG CAG TCA TTT TTG AAG AAA GAG TTG GAG TTC CTG GGC GTA ACC        246
Thr Trp Gln Ser Phe Leu Lys Lys Glu Leu Glu Phe Leu Gly Val Thr
     50                  55                  60

CAA GTT CTG GTT GGT TTG ATA TGC CTT TGT TTT GGA ACA GTT GTC TGC        294
Gln Val Leu Val Gly Leu Ile Cys Leu Cys Phe Gly Thr Val Val Cys
 65                  70                  75                  80

TCC ACA CTC CAG ACT TCA GAC TTT GAC GAC GAA GTG CTT TTA TTA TAT        342
Ser Thr Leu Gln Thr Ser Asp Phe Asp Asp Glu Val Leu Leu Leu Tyr
                 85                  90                  95

AGA GCA GGC TAC CCA TTC TGG GGT GCA GTG CTG TTT GTT TTG TCT GGA        390
Arg Ala Gly Tyr Pro Phe Trp Gly Ala Val Leu Phe Val Leu Ser Gly
             100                 105                 110

TTT TTG TCA ATT ATG TCC GAA AGG AAA AAC ACA CTG TAT CTG GTG AGA        438
Phe Leu Ser Ile Met Ser Glu Arg Lys Asn Thr Leu Tyr Leu Val Arg
         115                 120                 125

GGC AGC CTG GGA GCA AAC ATT GTC AGC AGC ATC GCT GCA GGC TTG GGG        486
Gly Ser Leu Gly Ala Asn Ile Val Ser Ser Ile Ala Ala Gly Leu Gly
     130                 135                 140

ATC GCC ATA TTG ATT CTC AAT CTG AGC AAC AAC TCC GCT TAT ATG AAC        534
Ile Ala Ile Leu Ile Leu Asn Leu Ser Asn Asn Ser Ala Tyr Met Asn
 145                 150                 155                 160

TAC TGC AAG GAT ATA ACC GAA GAC GAT GGT TGC TTC GTG ACT TCT TTC        582
Tyr Cys Lys Asp Ile Thr Glu Asp Asp Gly Cys Phe Val Thr Ser Phe
                 165                 170                 175

ATC ACA GAA CTG GTG TTG ATG TTG CTG TTT CTC ACC ATC CTG GCC TTT        630
Ile Thr Glu Leu Val Leu Met Leu Leu Phe Leu Thr Ile Leu Ala Phe
             180                 185                 190

TGC AGT GCC GTG CTG CTC ATT ATC TAT AGG ATT GGA CAA GAA TTT GAG        678
Cys Ser Ala Val Leu Leu Ile Ile Tyr Arg Ile Gly Gln Glu Phe Glu
         195                 200                 205

CGT AGT AAG GTC CCC GAT GAC CGT CTC TAT GAA GAA TTA CAT GTG TAT        726
Arg Ser Lys Val Pro Asp Asp Arg Leu Tyr Glu Glu Leu His Val Tyr
     210                 215                 220

TCA CCA ATT TAC AGT GCG TTG GAA GAC ACA AGG GAA GCG TCC GCA CCA        774
Ser Pro Ile Tyr Ser Ala Leu Glu Asp Thr Arg Glu Ala Ser Ala Pro
 225                 230                 235                 240

GTG GTT TCA TAAGAATCAA GGGGCCAGGA CAATCTGATT CCAGTCTAGT                823
Val Val Ser
CTTGAGAGTC GATCTTTTTG CAACATTATG CAACATTTC TGTTTCCTCC GCACTCTATC        883

AACTTTTCAA TTGGATTGTT CTGTAGATAC CCCTGTTTCA GTTATGATGC CTCTGGTCTT        943

TAATTATCTC CCTTTTTGTG GATATCGTTC AATCCAGTTT TCTTGTTTTG TGTCACAGTC       1003

TCACATACAA CCTTTCTGGA AAGTCATCAA AAACAAGCTA GCTTTTATTG CATGTCTACT       1063

TTCATGAACA AAAGGAAGGA GGAGTTATTT TGAGAGTTTA ACTAAACTTA GATAATCAGG       1123

TAATATTTGA CTCTTAGTTC ATTTTAGAAT TCTCAACAAT ACTTGTGCAT GATATATGCC       1183

CACCATATCA AGCCTTCTAT ATATATTTAA TATGGTATTT ACTTTTCTAT GTAGATAGAT       1243

TTTCCACCCT CAATAATAAT GGGTTTTTCA GAGACATAAA GCTTTATGAA AAGACACATA       1303
```

```
TTATCTAATT  CATGGGTATA  TTCACTAATA  CAGTTGTTGC  TCAGTGGTGT  TTACTACTTG   1363
GTGGGTAGTA  GGTAATAGAG  AACATTATTA  AATCATTCAG  TGTAGTGAGA  TGCATAGGTA   1423
AAATCAGGGA  CACTGTGAGT  GTGTATATCT  TTTGGTAAGA  CATGTGTGAA  AATGAAGAAT   1483
AAACTGATGA  AGACTTGAGC  TGGAAAGTAG  TCAATGGGAA  TGACAAGAAA  TGATTGTGTA   1543
TAACACTTGT  AGATAAATAA  CTACCAACAA  TTGGTAGAGA  TTGCCATGTA  TGCCTAAAAT   1603
CTCCCAGCCC  AAGGCCAGCC  TCTGTTACAC  AGTGAGTTAG  AGGCCAGTCT  GGGCTACACA   1663
AGATCATACA  TCAAAGGACG  AAAGAAGATG  TTGGTTCAAA  CTGTTAACAC  AGTAAGGGAT   1723
ATTTAAACAA  ACAGAAGTTT  GACTGATATA  TTGAGTGCTT  GAGTTTTTAA  TAAAACTGAA   1783
TGAATAACAT  TGCGGGGGAG  GGGAGCAGTG  ATGCAGAAGT  CTGGATGATG  GAGGAGTAGC   1843
AGAATCAGAT  GAAACATTGA  AACGTATTTC  CAGACTTTTG  TTCTGAGATG  GTTATAAGAG   1903
CAATCACCAT  TAAATGAAGA  AGGTCAAGAC  ACCAAAAGAA  TTATTTTGAG  ATAGAATTAA   1963
GACAGTCAAA  ATCCACATGC  CTATACTTAG  AAGGTGAAGT  AAGGATCAAA  AGTAGAAAGC   2023
CTAACGATTA  GTTGGAAAAG  CATATTACGT  TAGGCAGCAG  ATGTCTATAG  TGGAGAAAAG   2083
TTAAACAAGG  AGAAATAATG  AACCACCAGA  GACTCTACAT  GTTGGTTTGG  GAAATAAGAG   2143
AAAATAGCAA  TTCTAAACGA  ATGCAAACTC  TGAAGAAGCA  TTTCCCAAAG  GGTGTGGGCA   2203
GAGGACCAGA  ACATTTGCAA  ATGTACCTAG  AGAGCAAACC  TGAATAGGAG  GTAAAATGGG   2263
GGAAAAGCAG  CTAAGAAAAT  GATTTGTTG   CTGTTATTTA  GATTTAAAA   GAAACAAAAA   2323
GAGTCATTAA  AAATCTGTTT  GCTGGGATCA  GTTATTGTGT  TCTCTGTGTA  TGTCCAAAGT   2383
ACAGGTAACT  TTTCTAAATC  TTCCTGTAAG  GCTCACCTCA  TATGTCTCTT  CACATAGCCA   2443
CACCCTTGAT  TCACAGTTAC  TCTACCACAG  TAGTAAACTG  TGCTTGTGGT  CTCCCTTATG   2503
TATCTTCACT  AGTGTTTATA  AAATAAATCA  GAATTATTTA  AA                      2545
```

(2) INFORMATION FOR SEQ ID NO:23:

(i) SEQUENCE CHARACTERISTICS:
        (A) LENGTH: 246 amino acids
        (B) TYPE: amino acid
        (D) TOPOLOGY: linear (ii) MOLECULE TYPE: protein (xi) SEQUENCE DESCRIPTION: SEQ ID NO:23:

```
Met  Lys  Lys  Met  Asp  Thr  Glu  Asn  Lys  Ser  Arg  Ala  Asp  Leu  Ala  Leu
 -3            1              5                        10
Pro  Asn  Pro  Gln  Glu  Ser  Pro  Ser  Ala  Pro  Asp  Ile  Glu  Leu  Leu  Glu
          15             20                       25
Ala  Ser  Pro  Pro  Ala  Lys  Ala  Leu  Pro  Glu  Lys  Pro  Ala  Ser  Pro  Pro
 30                 35                       40                            45
Pro  Gln  Gln  Thr  Trp  Gln  Ser  Phe  Leu  Lys  Lys  Glu  Leu  Glu  Phe  Leu
                    50                       55                      60
Gly  Val  Thr  Gln  Val  Leu  Val  Gly  Leu  Ile  Cys  Leu  Cys  Phe  Gly  Thr
                65                       70                  75
Val  Val  Cys  Ser  Thr  Leu  Gln  Thr  Ser  Asp  Phe  Asp  Asp  Glu  Val  Leu
                80                       85                  90
Leu  Leu  Tyr  Arg  Ala  Gly  Tyr  Pro  Phe  Trp  Gly  Ala  Val  Leu  Phe  Val
           95                  100                      105
Leu  Ser  Gly  Phe  Leu  Ser  Ile  Met  Ser  Glu  Arg  Lys  Asn  Thr  Leu  Tyr
110                       115                      120                    125
Leu  Val  Arg  Gly  Ser  Leu  Gly  Ala  Asn  Ile  Val  Ser  Ser  Ile  Ala  Ala
```

|       |       |       |       |       | 130   |       |       |       | 135   |       |       |       | 140   |       |
|-------|-------|-------|-------|-------|-------|-------|-------|-------|-------|-------|-------|-------|-------|-------|
| Gly   | Leu   | Gly   | Ile   | Ala   | Ile   | Leu   | Ile   | Leu   | Asn   | Leu   | Ser   | Asn   | Asn   | Ser   | Ala
|       |       |       | 145   |       |       |       |       | 150   |       |       |       | 155   |       |       |
| Tyr   | Met   | Asn   | Tyr   | Cys   | Lys   | Asp   | Ile   | Thr   | Glu   | Asp   | Asp   | Gly   | Cys   | Phe   | Val
|       |       | 160   |       |       |       |       | 165   |       |       |       |       | 170   |       |       |
| Thr   | Ser   | Phe   | Ile   | Thr   | Glu   | Leu   | Val   | Leu   | Met   | Leu   | Leu   | Phe   | Leu   | Thr   | Ile
|       | 175   |       |       |       |       | 180   |       |       |       |       | 185   |       |       |       |
| Leu   | Ala   | Phe   | Cys   | Ser   | Ala   | Val   | Leu   | Leu   | Ile   | Ile   | Tyr   | Arg   | Ile   | Gly   | Gln
| 190   |       |       |       |       | 195   |       |       |       |       | 200   |       |       |       |       | 205
| Glu   | Phe   | Glu   | Arg   | Ser   | Lys   | Val   | Pro   | Asp   | Asp   | Arg   | Leu   | Tyr   | Glu   | Glu   | Leu
|       |       |       |       | 210   |       |       |       |       | 215   |       |       |       |       | 220   |
| His   | Val   | Tyr   | Ser   | Pro   | Ile   | Tyr   | Ser   | Ala   | Leu   | Glu   | Asp   | Thr   | Arg   | Glu   | Ala
|       |       |       | 225   |       |       |       |       | 230   |       |       |       | 235   |       |       |
| Ser   | Ala   | Pro   | Val   | Val   | Ser   |
|       |       | 240   |       |       |       |

(2) INFORMATION FOR SEQ ID NO:24:

(i) SEQUENCE CHARACTERISTICS:
        (A) LENGTH: 286 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..18

(xi) SEQUENCE DESCRIPTION: SEQ ID NO:24:

```
GTG AGA ACA TAT CTG TAATTGTTTC TGAAATGATG CTAACCAGAG ATTTTATTTT      55
Val Arg Thr Tyr Leu
 1           5
AATCAAAGAC AACTAATTTT CTTTTAATCA AGTGCTTATC TCTAGCCTTT CAATAATATC   115
TACAGTTCTT CATTTATATG CACATAGCCA TCTATAAATG TAGTTTCCAA AGCACTCTCT   175
ACATATACTC ATTAACAAGA GCAAATACAC TCACCACAGT TAACTATGGT TTAACCCATT   235
ACTATACTTT TATTGACTGA AAACCTTGAG ACTGTACAAA AAAAAAAAA A             286
```

(2) INFORMATION FOR SEQ ID NO:25:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:25:

```
Val Arg Thr Tyr Leu
 1           5
```

(2) INFORMATION FOR SEQ ID NO:26:

(i) SEQUENCE CHARACTERISTICS:
        (A) LENGTH: 586 base pairs
        (B) TYPE: nucleic acid
        (C) STRANDEDNESS: double
        (D) TOPOLOGY: linear (vi) ORIGINAL SOURCE:
        (A) ORGANISM: rat
        (B) STRAIN: FcRI gamma subunit (ix) FEATURE:
 (A) NAME/KEY: sig_peptide
 (B) LOCATION: 23..76

(ix) FEATURE:
 (A) NAME/KEY: mat_peptide
 (B) LOCATION: 77..283

(ix) FEATURE:
 (A) NAME/KEY: CDS
 (B) LOCATION: 23..283

(xi) SEQUENCE DESCRIPTION: SEQ ID NO:26:

```
AGCGCTGCAG  CCCCCGCCCA  GG ATG ATC CCA GCG GTG ATC TTG TTC TTG CTC          52
                          Met Ile Pro Ala Val Ile Leu Phe Leu Leu
                          -18         -15                 -10

CTT TTG GTG GAA GAA GCA GCT GCC CTA GGA GAG CCG CAG CTC TGC TAT            100
Leu Leu Val Glu Glu Ala Ala Ala Leu Gly Glu Pro Gln Leu Cys Tyr
            -5                   1                   5

ATC CTG GAT GCC ATC CTG TTT TTG TAT GGT ATT GTC CTT ACC CTG CTC            148
Ile Leu Asp Ala Ile Leu Phe Leu Tyr Gly Ile Val Leu Thr Leu Leu
        10                  15                  20

TAC TGT CGA CTC AAG ATC CAG GTC CGA AAG GCA GAC ATA GCC AGC CGT            196
Tyr Cys Arg Leu Lys Ile Gln Val Arg Lys Ala Asp Ile Ala Ser Arg
25              30                  35                      40

GAG AAA TCA GAT GCT GTC TAC ACG GGC CTG AAC ACC CGG AAC CAG GAG            244
Glu Lys Ser Asp Ala Val Tyr Thr Gly Leu Asn Thr Arg Asn Gln Glu
                45                  50                  55

ACA TAT GAG ACT CTG AAA CAT GAG AAA CCA CCC CAA TAGCTTTACA                 290
Thr Tyr Glu Thr Leu Lys His Glu Lys Pro Pro Gln
            60                  65

ACACGTGTTC  TCAGCTGCAT  TCCTTTTCCG  CTTTTAATTC  TCTCCTCGCC  CTCATGATTG     350

ACGTGGCTGT  GCTACCTCCG  TGCTTCTGGA  ACTAGCTGAC  CTTATTCCCA  GAACCATGCT     410

AGGCTCTAAA  TCAATGTCCC  CATATCCACC  AAAGACTTAC  TCACTGACAT  TTCTCTTCTC     470

CCATCCTCCT  TTGCTTCATT  CCTCTTTCCT  TCCCTGATCC  TCTGTGCTCA  CTAAACAATG     530

GGAAGGGATT  ACCCCCCAAT  AAAGCTGCCA  GAGATCACGC  TCAAAAAAAA  AAAAAA         586
```

(2) INFORMATION FOR SEQ ID NO:27:

(i) SEQUENCE CHARACTERISTICS:
  (A) LENGTH: 86 amino acids
  (B) TYPE: amino acid
  (D) TOPOLOGY: linear (ii) MOLECULE TYPE: protein (xi) SEQUENCE DESCRIPTION: SEQ ID NO:27:

```
Met Ile Pro Ala Val Ile Leu Phe Leu Leu Leu Val Glu Glu Ala
-18         -15                 -10                 -5

Ala Ala Leu Gly Glu Pro Gln Leu Cys Tyr Ile Leu Asp Ala Ile Leu
        1                   5                   10

Phe Leu Tyr Gly Ile Val Leu Thr Leu Leu Tyr Cys Arg Leu Lys Ile
15                  20                  25                  30

Gln Val Arg Lys Ala Asp Ile Ala Ser Arg Glu Lys Ser Asp Ala Val
                35                  40                  45

Tyr Thr Gly Leu Asn Thr Arg Asn Gln Glu Thr Tyr Glu Thr Leu Lys
            50                  55                  60

His Glu Lys Pro Pro Gln
            65
```

(2) INFORMATION FOR SEQ ID NO:28:

(i) SEQUENCE CHARACTERISTICS:
    (A) LENGTH: 222 amino acids
    (B) TYPE: amino acid
    (D) TOPOLOGY: linear (ii) MOLECULE TYPE: protein (vi) ORIGINAL SOURCE:
    (B) STRAIN: alpha subunit (xi) SEQUENCE DESCRIPTION: SEQ ID NO:28:

| Ala | Thr | Gln | Lys | Ser | Val | Val | Ser | Leu | Asp | Pro | Pro | Trp | Ile | Arg | Ile |
|---|---|---|---|---|---|---|---|---|---|---|---|---|---|---|---|
| 1 | | | | 5 | | | | | 10 | | | | | 15 | |
| Leu | Thr | Gly | Asp | Lys | Val | Thr | Leu | Ile | Cys | Asn | Gly | Asn | Asn | Ser | Ser |
| | | | 20 | | | | 25 | | | | | 30 | | | |
| Gln | Met | Asn | Ser | Thr | Lys | Trp | Ile | His | Asn | Asp | Ser | Ile | Ser | Asn | Val |
| | | 35 | | | | | 40 | | | | | 45 | | | |
| Lys | Ser | Ser | His | Trp | Val | Ile | Val | Ser | Ala | Thr | Ile | Gln | Asp | Ser | Gly |
| 50 | | | | | | 55 | | | | | 60 | | | | |
| Lys | Tyr | Ile | Cys | Gln | Lys | Gln | Gly | Phe | Tyr | Lys | Ser | Lys | Pro | Val | Tyr |
| 65 | | | | | 70 | | | | 75 | | | | | 80 | |
| Leu | Asn | Val | Met | Gln | Glu | Trp | Leu | Leu | Leu | Gln | Ser | Ser | Ala | Asp | Val |
| | | | | 85 | | | | | 90 | | | | | 95 | |
| Val | Leu | Asp | Asn | Gly | Ser | Phe | Asp | Ile | Arg | Cys | Arg | Ser | Trp | Lys | Lys |
| | | | 100 | | | | | 105 | | | | | 110 | | |
| Trp | Lys | Val | His | Lys | Val | Ile | Tyr | Tyr | Lys | Asp | Asp | Ile | Ala | Phe | Lys |
| | | 115 | | | | | 120 | | | | | 125 | | | |
| Tyr | Ser | Tyr | Asp | Ser | Asn | Asn | Ile | Ser | Ile | Arg | Lys | Ala | Thr | Phe | Asn |
| | 130 | | | | | 135 | | | | | 140 | | | | |
| Asp | Ser | Gly | Ser | Tyr | His | Cys | Thr | Gly | Tyr | Leu | Asn | Lys | Val | Glu | Cys |
| 145 | | | | | 150 | | | | | 155 | | | | | 160 |
| Lys | Ser | Asp | Lys | Phe | Ser | Ile | Ala | Val | Val | Lys | Asp | Tyr | Thr | Ile | Glu |
| | | | | 165 | | | | | 170 | | | | | 175 | |
| Tyr | Arg | Trp | Leu | Gln | Leu | Ile | Phe | Pro | Ser | Leu | Ala | Val | Ile | Leu | Phe |
| | | | 180 | | | | | 185 | | | | | 190 | | |
| Ala | Val | Asp | Thr | Gly | Leu | Trp | Phe | Ser | Thr | His | Lys | Gln | Phe | Glu | Ser |
| | | 195 | | | | | 200 | | | | | 205 | | | |
| Ile | Leu | Lys | Ile | Gln | Lys | Thr | Gly | Lys | Gly | Lys | Lys | Lys | Gly | | |
| | 210 | | | | | 215 | | | | | 220 | | | | |

(2) INFORMATION FOR SEQ ID NO:29:

(i) SEQUENCE CHARACTERISTICS:
    (A) LENGTH: 243 amino acids
    (B) TYPE: amino acid
    (D) TOPOLOGY: linear (ii) MOLECULE TYPE: protein (vi) ORIGINAL SOURCE:
    (B) STRAIN: beta subunit (xi) SEQUENCE DESCRIPTION: SEQ ID NO:29:

| Met | Asp | Thr | Glu | Asn | Lys | Ser | Arg | Ala | Asp | Leu | Ala | Leu | Pro | Asn | Pro |
|---|---|---|---|---|---|---|---|---|---|---|---|---|---|---|---|
| 1 | | | | 5 | | | | | 10 | | | | | 15 | |
| Gln | Glu | Ser | Pro | Ser | Ala | Pro | Asp | Ile | Glu | Leu | Leu | Glu | Ala | Ser | Pro |
| | | | 20 | | | | | 25 | | | | | 30 | | |
| Pro | Ala | Lys | Ala | Leu | Pro | Glu | Lys | Pro | Ala | Ser | Pro | Pro | Gln | Gln |
| | | | 35 | | | | 40 | | | | | 45 | | | |
| Thr | Trp | Gln | Ser | Phe | Leu | Lys | Lys | Glu | Leu | Glu | Phe | Leu | Gly | Val | Thr |

|  | 50 |  |  |  | 55 |  |  |  | 60 |  |  |  |
|---|---|---|---|---|---|---|---|---|---|---|---|---|

Gln Val Leu Val Gly Leu Ile Cys Leu Cys Phe Gly Thr Val Val Cys
65                     70                  75                  80

Ser Thr Leu Gln Thr Ser Asp Phe Asp Asp Glu Val Leu Leu Leu Tyr
                85                  90                  95

Arg Ala Gly Tyr Pro Phe Trp Gly Ala Val Leu Phe Val Leu Ser Gly
            100                 105                 110

Phe Leu Ser Ile Met Ser Glu Arg Lys Asn Thr Leu Tyr Leu Val Arg
        115                 120                 125

Gly Ser Leu Gly Ala Asn Ile Val Ser Ser Ile Ala Ala Gly Leu Gly
    130                 135                 140

Ile Ala Ile Leu Ile Leu Asn Leu Ser Asn Ser Ala Tyr Met Asn
145                 150                 155                 160

Tyr Cys Lys Asp Ile Thr Glu Asp Asp Gly Cys Phe Val Thr Ser Phe
                165                 170                 175

Ile Thr Glu Leu Val Leu Met Leu Leu Phe Leu Thr Ile Leu Ala Phe
            180                 185                 190

Cys Ser Ala Val Leu Leu Ile Ile Tyr Arg Ile Gly Gln Glu Phe Glu
        195                 200                 205

Arg Ser Lys Val Pro Asp Asp Arg Leu Tyr Glu Glu Leu His Val Tyr
    210                 215                 220

Ser Pro Ile Tyr Ser Ala Leu Glu Asp Thr Arg Glu Ala Ser Ala Pro
225                 230                 235                 240

Val Val Ser ( 2 ) INFORMATION FOR SEQ ID NO:30:

( i ) SEQUENCE CHARACTERISTICS:
        ( A ) LENGTH: 62 amino acids
        ( B ) TYPE: amino acid
        ( D ) TOPOLOGY: linear ( i i ) MOLECULE TYPE: protein ( v i ) ORIGINAL SOURCE:
        ( B ) STRAIN: gamma subunit ( x i ) SEQUENCE DESCRIPTION: SEQ ID NO:30:

Leu Gly Glu Pro Gln Leu Cys Tyr Ile Leu Asp Ala Ile Leu Phe Leu
1               5                   10                  15

Tyr Gly Ile Val Leu Thr Leu Leu Tyr Cys Arg Leu Lys Ile Gln Val
            20                  25                  30

Arg Lys Ala Asp Ile Ala Ser Arg Glu Lys Ser Asp Ala Val Tyr Thr
        35                  40                  45

Gly Leu Asn Thr Arg Asn Gln Glu Thr Tyr Glu Thr Leu Lys
    50                  55                  60

( 2 ) INFORMATION FOR SEQ ID NO:31:

( i ) SEQUENCE CHARACTERISTICS:
        ( A ) LENGTH: 11298 base pairs
        ( B ) TYPE: nucleic acid
        ( C ) STRANDEDNESS: single
        ( D ) TOPOLOGY: linear ( v i ) ORIGINAL SOURCE:
        ( A ) ORGANISM: homo sapien
        ( B ) STRAIN: FcRI beta ( x i ) SEQUENCE DESCRIPTION: SEQ ID NO:31:

AAGCTTTTCA AAGGTGCAAT TGGATAACTT CTGCCATGAG AAATGGCTGA ATTGGGACAC    60

| | | | | | |
|---|---|---|---|---|---|
| AAGTGGGGAC | AATTCCAGAA | GAAGGGCACA | TCTCTTTCTT | TTCTGCAGTT | CTTTCTCACC | 120 |
| TTCTCAACTC | CTACTAAAAT | GTCTCATTTT | CAGGTTCTGT | AAATCCTGCT | AGTCTCAGGC | 180 |
| AAAATTATGC | TCCAGGAGTC | TCAAATTTTC | TTATTTCATA | TTAGTCTTTA | TTTAGTAGAC | 240 |
| TTCTCAATTT | TTCTATTCAT | CACAAGTAAA | AGCCTGTTGA | TCTTAATCAG | CCAAGAAACT | 300 |
| TATCTGTCTG | GCAAATGACT | TATGTATAAA | GAGAATCATC | AATGTCATGA | GGTAACCCAT | 360 |
| TTCAACTGCC | TATTCAGAGC | ATGCAGTAAG | AGGAAATCCA | CCAAGTCTCA | ATATAATAAT | 420 |
| ATTCTTTATT | CCTGGACAGC | TCGGTTAATG | AAAAAATGGA | CACAGAAAGT | AATAGGAGAG | 480 |
| CAAATCTTGC | TCTCCCACAG | GAGCCTTCCA | GGTAGGTACA | AGGTATTATT | TTTTCTACC | 540 |
| CTCAGTCACT | TGTGGCAGGG | GAAGTCATAG | TCACGGTGCT | TAGGAGATGA | AACTTTATTG | 600 |
| ATTTAGGCAT | GGATCCATCT | AGTTTAATTA | ATATATTGGG | TATGAGGAAG | CTACTTGCTG | 660 |
| TACTTTCCAT | GTGGTTCTCT | CTCCCTGGAG | AGGAACATTT | TACTCAGCT | TGCAAACTGG | 720 |
| AAATAGATTT | TCTCACATTA | GAAGCTCATT | TTCTGGGTAT | GAGACAGGAG | AGTTCATACT | 780 |
| GTGTATGTAG | ATCTCTGGCT | TCTGGGTCTG | ACATGTGCTG | AGGGACACAT | ATCCTTCACA | 840 |
| CATGCTTTTA | TAAATACTTG | ATAAAGTAAC | CTGCTTCTTG | ATTGGTCTTT | ATAATCCATA | 900 |
| AGCTGTGGGA | TGCTTCTCTG | AAGATGAAAA | TAGTAATAGA | GTCCCATCTA | GCTATTCAAA | 960 |
| GCCATTCCTT | CATTGTATTC | TGTGCACATG | AAGTTGGGGT | TTGTTACTGA | CAAAATATAT | 1020 |
| TCAGATACAT | TTCTATGTTA | AAAGGATTGT | GAGATGCATA | GGTAAATGTG | TTTATTTTCA | 1080 |
| GTTTTACTTG | TCAACATAGA | TGAATGAGAA | AGAACTTGAA | AGTAACACTG | GATTAAGAAT | 1140 |
| AGGAAAATTT | GGCATGGATT | TTGCTCCATT | TTGTCCCATC | TAATCACTTG | GATAGTGTTC | 1200 |
| AGGTGTTCTT | GGTCAGTTAC | TTGGATGCTC | TGAGCTTTAG | TTTCTTGGTG | ATTACAATGA | 1260 |
| AGATTTGAAT | TACAGGATGG | CTTTGAAAAA | ATAAACAAAA | CTCCCCTTTC | TGTCTGTCGA | 1320 |
| GAATGTTGCA | CAGGGAGTTA | CAGAATGTTC | TCATGACTGA | ATTGCTTTTA | AATTTCACAG | 1380 |
| TGTGCCTGCA | TTTGAAGTCT | TGGAAATATC | TCCCCAGGAA | GTATCTTCAG | GCAGACTATT | 1440 |
| GAAGTCGGCC | TCATCCCCAC | CACTGCATAC | ATGGCTGACA | GTTTGAAAA | AAGAGCAGGA | 1500 |
| GTTCCTGGGG | GTGAGTGAGC | CTCCTCCAAC | TTTGACTAGA | GTAAGGGTTG | GGTCTAGAAA | 1560 |
| AGAATATTGA | GTTGCATCAA | CTGTTTTCCC | ACTTGGATTC | ATGAGAGGTG | TTAGGTCCTT | 1620 |
| TAAAAAACAT | GGTAGATAAA | GAGTTGACAC | TAACTGGGTC | CTTTTGGGAA | GAGCCAGAAG | 1680 |
| CATTTCCTCA | TAAAGACTTT | AAATTGCTAG | GACGAGAATG | GCCAACAGGA | GTGAAGGATT | 1740 |
| CATAACTTTA | TCTTTACTTA | GATGTAAAGA | ACAATTACTG | ATGTTCAACA | TGACTACATA | 1800 |
| CATAAAGGCG | CATGGAGAAA | AGTATTGGCC | TTCCATGCAT | TAGGTAGTGC | TTGTATCAAT | 1860 |
| TCTTATAGTG | GCTAGGGTAT | CCTGGAAAAT | CTTACGTGTG | GATCATTTCT | CAGGACAGTC | 1920 |
| TAGGACACTA | ACGCAGTTTC | TCATGTTTGG | CTTCTATTAT | TAAAAAATGA | TACAATCTCG | 1980 |
| GGAAAATTTT | TTTGATTTTC | ATGAAATTCA | TGTGTTTTTC | TATAGGTAAC | ACAAATTCTG | 2040 |
| ACTGCTATGA | TATGCCTTTG | TTTTGGAACA | GTTGTCTGCT | CTGTACTTGA | TATTTCACAC | 2100 |
| ATTGAGGGAG | ACATTTTTTC | ATCATTTAAA | GCAGGTTATC | CATTCTGGGG | AGCCATATTT | 2160 |
| GTGAGTATAT | ATCTATAATT | GTTTCTGAAA | TAACACTGAA | CATAGGTTTT | TCTCTTTCTC | 2220 |
| AGATCTAACC | AGTTGTTTAT | TCCCAGTATT | AAGATGATAT | TTATAATTCT | TAATTATAAA | 2280 |
| TATATGTGAG | CATATATAAC | ATAGATATGC | TCATTAACAA | CAACAAAAGA | TTCTTTTTAC | 2340 |
| AATTAACGGT | GGGTTAAACA | TTTAGCCCAC | AGTTTATCC | CATGAGAAAC | CTGAATCTAA | 2400 |
| TACAAGTTAA | ATGACTTGCC | TAAGGGCCAC | TTGACTAATA | GTAATTGAAC | CTAAACTTTC | 2460 |

```
AGAATCCAAC TCCAGGAACA TACTTCTAGC ACTATTCATC AATAAAGTTA TATGATAAAT    2520
ACATACAACT TTATCTGTCA ACTAAAAATA ACAACAGAGG CTGGGCATGG TGGCTCACAC    2580
CCGTAATCCC AGCACTTTGG GAGGCTGAGG CAGGTGGATC ACCTGAGGTC AGGAGTTTGA    2640
GACCAGCCTG ACCAACATGG TGAAACCTCA TCTCTACTAA ATATAAAAAA TTAGCTGAGT    2700
GTGATAGTGC ATACCTGTAA TCCAGCTACT TAAGAGGCTG AGGCAGGAGG CTTGTTTGAA    2760
CCTGGAAGGC AGAGGTTGCA GTGAGCTGAG ATTGTGCCAT TGCACTCCAG CCTGGGCAAT    2820
AAGTGCGAAC TCTGTCTCAA AATAATAATA ATAATAATAG AAAATAAAGT TGTCTTCATG    2880
AAAAATGAGG AAAGAGATTG CTGGGGTGAG AAACATTAAG ATCAATGGGC ATATGGTGAC    2940
CTTCTATGCC CTAGAAACTC TTTTANGGTA TTTTCTCCTG GTATCTCTTT TACNCATCGT    3000
TCTATCTGGA AAAATAGGTG GATGAGTGAG ATAATAACGG TATATACTTT TTAAAGGTCT    3060
AATTGACATA TATAAATTGC AAGTATTTCA GATGTCAATT TGCTAACCTT GACACACATA    3120
GACACACATG AAAACATCAC CACATTAATA CAATGTATGT ATCCATCATT CCAAAAGCTT    3180
CCCTGTGTAT CTTTGTAACT CTTTCTTCCT CCCTCCACTC CTTGTCCTCT CGTTCCCAAG    3240
AAAACATTGA TCTGCTTCCT GTGAATATAA ATTAACTTAC ATTTTTAGA GCTTTATATA     3300
AGTATGTTCT CTTTACTGTT TGTCTTCCTT CGCTGCACAG TTATTTTGAG ATTCTTCAAG    3360
TTTTTTCTTT ATATCGATAC TTCATTCACA AGAATATATT TTAATTCTAG ACTATGTCAC    3420
ATTGACTTTG TCGTCTGCTA AATCCTTAGT GCTCAGATGA CTTGTTCAGG ACTCTCCTTG    3480
AACCTGTACC TCTGTTANAT TGAAACTTGT CTCTACTGTC TTTTTATTTC AAACACAGCT    3540
TATTAGGTGT CTCTCAACCC ATCAAACNCA CAATCTGAGT CTTTAGGAGA TTGCTTTGAA    3600
TTTGTGCTAT TGACTTATAT NTATATNAAA TNTGTAAATG TTTGGTAAAA ATATCATCAT    3660
GTACNTTTTC ATAATTACGC TATNTNCACA TGATATATGT CAGACTCTGG AAATATGCAT    3720
GCCACAGACA CGTGTTTCTT GCCTAAAGGG GCTGATGGAA GACNCACATA CNAATAGACG    3780
ATTGCAGTAG AATGAGAGTG GTGGTCTAAN CAGTACATGT CCTGATGTTG CTCGGACAGT    3840
TACTACNCCA AGAGTACCCC CTGCATTGTC AGGGTTAGCA TCTCCTGGAA GCCTCATGTA    3900
AATGAAGAAT TCATGCTCC ATCCAGGACC TAATGAATAA GAATCTGCAT TTTAGCAAGA     3960
CCCTCATATG ATTCATATAC ACTTTTTTTT TTTTTTTTA GATGGAGTCT CACTCTTGTC     4020
GCCCAGGCTG GAGTGCAATG GCATGATCTT GGCTCACTGC AACCTCTGCC TCCCGGGTTC    4080
AAGTGATTCT CCTGTCTCAG CCTCCCTAGT AGCTGGGACT ACAGGTGCAT GCCACAGTGG    4140
CTGGCTAATT TTTGTATTTT TAGTAGAGAC AGGGTTTCAC CATTTTGGTC AGGCTGGTCT    4200
TGAACTCATG ACCTCCGGTG ATTCCCCGC CTCGGCTTCC CAAAGTGCTG GGATTACAGA     4260
CATGAGCCAC CACACCCGCC TTATTCGTAT ACNCATTTAA TTCTGAGAAG CACTCTATAG    4320
AAAATAAGAA TAAGAAAATA TTGGGCTCAC AGGTGACATT AATAAGTAAC TTTATCGAGT    4380
ACCCCAAATT TTACCTATGT TTGGAAGATG GGGTTAAAAG GACACATTGA AAACAAGAAC    4440
TCATTGTGGC TTTTTTTTCC TCCTTTTTGA ACAGTTTTCT ATTTCTGGAA TGTTGTCAAT    4500
TATATCTGAA AGGAGAAATG CAACATATCT GGTGAGTTGC CCGTTTCTGT CTTTGTCCAT    4560
CCTTGAAAAG ATAAGAAGAA CAGAGTTTTA AGAGTCTTAA GGGAAACACA TCTTTGTCTC    4620
CTATATTACT TGTGAATGTG GATATATGAT TTTGTTTCAA TCTATTTTGT GTCCTAAGGC    4680
TTTTTGCAAC AGAAGTTGGA TATATCATTA GAAACATAAA TTGTACCATT TAACATACAT    4740
GAAGTTTATG TTTACCTTGA CGTTCTTCTA AAAAGTGTCC TACACCGGCA TTGTCCTTGT    4800
AGGCATATTC ACATGATCAA ATAAAATAAT TAGTTTTCAA TTAAGGAGAA TATTTGAGGA    4860
```

```
AAGACCGTAC GTGTTCATGT GGTTCCTGAA GGCAGTCCAG TGAGAAAGTA ATATATGCTT    4920
CATTAAACAA TGCGGACATT TTCAGGGTTT CCCTTTTTAA CCAAAATTTG GAAGCAATGT    4980
GGAATTTACT GGATGCATCC AGCCCTGAAA TGAAGATAGG TTTATTGAAT GTGCCAGCAA    5040
GTGCAGGCCC AGGTCTGAGT GTTCTTCATT ATTATCAGGT GAGAGGAAGC CTGGGAGCAA    5100
ACACTGCCAG CAGCATAGCT GGGGGAACGG GAATTACCAT CCTGATCATC AACCTGAAGA    5160
AGAGCTTGGC CTATATCCAC ATCCACAGTT GCCAGAAATT TTTTGAGACC AAGTGCTTTA    5220
TGGCTTCCTT TTCCACTGTA TGTATTTTTT TTTGTGTGGG AAGACTAAGA TTCTGGGTCC    5280
TAATGTAAGT AAGAAGCCCT CTTCTCCTGT TCCATGAACA CCATCCTTTT CTGTAACTTC    5340
TATTACACAG TATAGTGGTT CTGTAAGTTC ACACAGCCCA GGGAGATGCT GGCTGCCCAC    5400
TCCCCTCAAC CCAGGCAAAT TCCTCGGGGT TAAAGTTATC TACTGCAAGT GACGATCTCT    5460
GGGTTTTTCT GTGCCTGTGT TTGTGTGTGT GTGTGTGTGT GTGTGTGTGT GTATGTGTCA    5520
CTTTAAAAGG ACTGGTCAGA TGGTAGGGAG ATGAAAACAG GAGATGCTAT AAGAAAATAA    5580
ACTTTTGGGG CGAATACCAA TGTGACTCTT TTTGTTTGTC ATTTGTTGCT GTTCAATAGG    5640
AAATTGTAGT GATGATGCTG TTTCTCACCA TTCTGGGACT TGGTAGTGCT GTGTCACTCA    5700
CAATCTGTGG AGCTGGGGAA GAACTCAAAG GAAACAAGGT AGATAGAAGC CCGATATAAA    5760
ATCTTGAATG ACAGGTAAC GAATTGGAGC TTTATTCCTT AAAATATGGC CTGGGTTTTC    5820
TGAAACATTT CTTCCAGAAA ATAGTTTCTC CAAGTTTTAT TACTTTGGTT TACAAATCTC    5880
ACATTTAAAT CACATTTTAT ACCATAAGTA GCACACATTT CATAATATTC CTCTGAATGA    5940
GGGTTGGGAT AATAGGACTG ATATGTTAGA AATGCCTTAA AGTGTGTGGA GCATGAGAGA    6000
TGGATGTACA GAAGGCTTGT GAGGAAACCA CCCAGGTATC TGGCCTTGTT TTCTGCCCCA    6060
GAACTAGCCG CCTATTCCTG TTTCTGTTTT ATTCCTTTGT TTCTTGACTT TTCCTTTCCA    6120
ACTTGCTCTA AAACCTCAGT TTTCTTTCCT TTCTGATTCA TGACTACCAA ATGTTTTCAC    6180
TTGCCTCACC CGTCCATTAC ACCTTTGATA AGAACCACCA GACCTTGTGC TCATGTACTT    6240
GCCCATGTCT GATGGAAGAA ACATACTCTC TCCATCTGTC CACTTTCCTG AGGCATTCAA    6300
GTCTAGCCAC CTTTTAAAAT CACTCTCCTC CAGGCTGGGC ACGGTGTCAC GCCTGTAATC    6360
TCAGCACTTT GTGAGGCTGA GGAGGGCGGA TCACTTGAAG TCAGGAGTTC AAAACCAGCC    6420
TGGCCAAATG GCAAAACCAA ATCTTCTTCA ATTATAACCA AATCTTAAAC CAAATCTCTA    6480
CTAAAAAATA CAACAAAACA AAACAACAAC AACAAAAACA GAAAAGGAAA CATTAGCCCA    6540
GCGTGGTGGC AGGTACCTGA GGTTCCAGAT ACTTGGGAGG CTGAAGCAGG AGAATCGCTT    6600
GAGCCCAAGA GATGGAGGTT GCAGTGAGCC GAGATCATGC CACTGCACCA CAGCCAGGGT    6660
GACAGAGCCA TACTTCCCAG CACATTGGGA GGCCAAAGCT GAAGAATAAT TTGAGGTGAG    6720
GATTGGAGA CCAGCCTGGC CAACATGGTG AAACTCCGTC TGTACTAAAA ATATAAAACT    6780
TAGTGGGGCA TGGGGGCACA CACCTGTAAT TTCAGCTACT TAGGAGGCTG AGGCAGGAGA    6840
ATTGCTTGAA CCCGGGAGGC GGAAGTTGCA GTGAGCCAAG ATCGTGGCCA CTGCACTCCA    6900
GCCTGGGTGA CATAGTGAGA TTCTGTCTCA AAAAAAATAA AAGAAATTTA AAAATCACT    6960
CTCTTCCAAA GATAGATAAA TAAGACAGCA GATATACTAA GGAATAACCT CACCAACTTG    7020
TCATTGACTG ACATGATTTC TTTTGGCCCA CTTGGCCAGC TAGTCTGGTT TGGTTTTCTG    7080
GAAATGAAAG AAATAATCAG AGTTTAATGA CAGAGAGCGT GAGACCCAGA AAGACAAAAG    7140
TAGATGAGGT AAGTCTCTTG AGCGAGACTT CTAGGGATGG GAAATTTGTG GTGATTGATA    7200
TGAAATGATT TTTCCCTTAT CAGGTTCCAG AGGATCGTGT TTATGAAGAA TTAAACATAT    7260
```

```
ATTCAGCTAC   TTACAGTGAG   TTGGAAGACC   CAGGGGAAAT   GTCTCCTCCC   ATTGATTTAT   7320
AAGAATCACG   TGTCCAGAAC   ACTCTGATTC   ACAGCCAAGG   ATCCAGAAGG   CCAAGGTTTT   7380
GTTAAGGGGC   TACTGGAAAA   ATTTCTATTC   TCTCCACAGC   CTGCTGGTTT   TACATTAGAT   7440
TTATTCGCCT   GATAAGAATA   TTTTGTTTCT   GCTGCTTCTG   TCCACCTTAA   TATGCTCCTT   7500
CTATTTGTAG   ATATGATAGA   CTCCTATTTT   TCTTGTTTTA   TATTATGACC   ACACACATCT   7560
CTGCTGGAAA   GTCAACATGT   AGTAAGCAAG   ATTTAACTGT   TTGATTATAA   CTGTGCAAAT   7620
ACAGAAAAAA   AGAAGGCTGG   CTGAAAGTTG   AGTTAAACTT   TGACAGTTTG   ATAATATTTG   7680
GTTCTTAGGG   TTTTTTTTTT   TTTTAGCATT   CTTAATAGTT   ACAGTTGGGC   ATGATTTGTA   7740
CCATCCACCC   ATACCCACAC   AGTCACAGTC   ACACACACAT   ATGTATTACT   TACACTATAT   7800
ATAACTTCCT   ATGCAAATAT   TTTACCACCA   GTCAATAATA   CATTTTTGCC   AAGACATGAA   7860
GTTTTATAAA   GATCTGTATA   ATTGCCTGAA   TCACCAGCAC   ATTCACTGAC   ATGATATTAT   7920
TTGCAGATTG   ACAAGTAGGA   AGTGGGGAAC   TTTTATTAAG   TTACTCGTTG   TCTGGGGAGG   7980
TAAATAGGTT   AAAAACAGGG   AAATTATAAG   TGCAGAGATT   AACATTTCAC   AAATGTTTAG   8040
TGAAACATTT   GTGAAAAAAG   AAGACTAAAT   TAAGACCTGA   GCTGAAATAA   AGTGACGTGG   8100
AAATGGAAAT   AATGGTTATA   TCTAAAACAT   GTAGAAAAAG   AGTAACTGGT   AGATTTTGTT   8160
AACAAATTAA   AGAATAAAGT   TAGACAAGCA   ACTGGTTGAC   TAATACATTA   AGCGTTTGAG   8220
TCTAAGATGA   AAGGAGAACA   CTGGTTATGT   TGATAGAATG   ATAAAAGGG   TCGGGCGCGG   8280
AGGCTCACGC   CTGTAATCCC   AGCCCTTTGG   GAGGCCGAGG   TGGGCAGATC   ACGAAGTCAG   8340
TAGTTTGAGA   CCAGCCTGGC   CAACATAGTG   AAACCCCGTC   TCTACTAAAA   ATACAAAAAA   8400
AAAATTAGCT   GGGTGTGGTG   GCAGTCACCT   GTAGTCCCAG   CTACTTGGGA   GGATGAGGCA   8460
GGAGAATCGC   TTGAACCTGG   GAGGCGGAGG   TTGCAGTGAG   CCGAGATCGC   ACCAGTGCAC   8520
TCCAGCCTTG   GTGACAATGG   GAGACTCCAT   CTCAAAAAAA   AAAAAAAAA   AAAAAAGATA   8580
AAAAGTCAGA   AATCTGAAAA   GTGGAGGAAG   AGTACAAATA   GACCTAAATT   AAGTCTCATT   8640
TTTTGGCTTT   GATTTTGGGG   AGACAAAGGG   AAATGCAGCC   ATAGAGGGCC   TGATGACATC   8700
CAATACATGA   GTTCTGGTAA   AGATAAAATT   TGATACACGG   TTTGGTGTCA   TTATAAGAGA   8760
AATCATTATT   AAATGAAGCA   AGTTAACACT   CTAAGAGAAT   TATTTTGAGA   TAGAAGTGAA   8820
GCTAAGCTAA   ACTTCACATG   CCTATAATTG   GAGGGAAAAA   CTAAGGATAA   AATCTAGCCT   8880
AGAAGATACA   ATAATTAGTC   ATAAACATGC   ATTGTGAAAC   TGTAGAGAGC   AGGTAGCCCA   8940
AAATAGAGAA   AGATTAGATA   AAGAGAAAAT   AAGTATCCAT   CAGAGACAGT   ATCTCTAGGC   9000
TTGGGCAAGA   GAAAAGTCCA   CAGTGATAAG   CAACTCCACC   TAAGGCATGA   ATATGCGGCA   9060
GAGAAAACAG   CAATAGTGAA   TGAATGCAAA   AGGTGCTGAG   CAAATTCCAC   ACATGAGTAT   9120
TGTGCATGAG   TAAATGAATA   AAACATTTGC   AAAGACCTTT   AGAGAAAGAG   AATGGGAGCA   9180
TATGTGCGAA   ATAAGATAGT   TGATTATGAA   TAGAAGGTAG   TGAAGAAAAG   CAAGCTAAGA   9240
AAAAATTCTG   TTTATAAAAG   AAGGAAAAGA   TAGTTTATGT   TTTTAGCCTA   AGTATAAGAG   9300
TCCTACAGAT   GGACTGAAAA   AAATCAGTCT   GAGAGTATTA   GTCACAATTA   ATGAAATAAT   9360
TACATTTTAT   GTATTGAGGA   TGCCAAGATT   AAAAGGTGAC   AGGTAGATGT   TAATTTCCCT   9420
AGATTGTGAA   AGTGATCACG   ACAATCACAC   AACAAATAAT   TAAGTGACTT   GGTATGCTTT   9480
ATTTAATTGT   AGGGCCTGAG   GTTTTCCATT   CTCATTTTTC   TAAAATACAA   TTTTGTTTCT   9540
CCAAATTTGA   CAGCAGAATA   AAAACCCTAC   CCTTTCACTG   TGTATCATGC   TAAGCTGCAT   9600
CTCTACTCTT   GATCATCTGT   AGGTATTAAT   CACATCACTT   CCATGGCATG   GATGTTCACA   9660
```

| | | | | | |
|---|---|---|---|---|---|
| TACAGACTCT | TAACCCTGGT | TTACCAGGAC | CTCTAGGAGT | GGATCCAATC | TATATCTTTA | 9720 |
| CAGTTGTATA | GTATATGATA | TCTCTTTTAT | TTCACTCAAT | TTATATTTTC | ATCATTGACT | 9780 |
| ACATATTTCT | TATACACAAC | ACACAATTTA | TGAATTTTTT | CTCAAGATCA | TTCTGAGAGT | 9840 |
| TGCCCCACCC | TACCTGCCTT | TTATAGTACG | CCCACCTCAG | GCAGACACAG | AGCACAATGC | 9900 |
| TGGGGTTCTC | TTCACACTAT | CACTGCCCCA | AATTGTCTTT | CTAAATTTCA | ACTTCAATGT | 9960 |
| CATCTTCTCC | ATGAAGACCA | CTGAATGAAC | ACCTTTTCAT | CCAGCCTTAA | TTTCTTGCTC | 10020 |
| CATAACTACT | CTATCCCACG | ATGCAGTATT | GTATCATTAA | TTATTAGTGT | GCTTGTGACC | 10080 |
| TCCTTATGTA | TTCTCAATTA | CCTGTATTTG | TGCAATAAAT | TGGAATAATG | TAACTTGATT | 10140 |
| TCTTATCTGT | GTTTGTGTTG | GCATGCAAGA | TTTAGGTACT | TATCAAGATA | ATGGGGAATT | 10200 |
| AAGGCATCAA | TAAAATGATG | CCAAAGACCA | AGAGCAGTTT | CTGAAGTCCT | CCTTTTCATC | 10260 |
| AGCTCTTTAT | CAAACAGAAC | ACTCTATAAA | CAACCCATAG | CCAGAAAACA | GGATGTAGGA | 10320 |
| ACAATCACCA | GCACACTCTA | TAAACAACCC | ATAGCCAGAA | AACAGAATGT | AAGGACAATC | 10380 |
| ACCAGCCATC | TTTTGTCAAT | AATTGATGGA | ATAGAGTTGA | AAGGAACTGG | AGCATGAGTC | 10440 |
| ATATTTGACC | AGTCAGTCCT | CACTCTTATT | TACTTGCTAT | GTAAACTTGA | GAAAGCTTTT | 10500 |
| TTCTCTTTGT | GAACCTCAGG | TTTTACATCT | GAAAATGAGA | AATTTGGAAC | AAAAGATTCC | 10560 |
| TAACTGGTCT | TTCTGTTCCC | ATATTCTGTG | ATTTTTCAAT | ATTTAGGATT | TTTGGTAATC | 10620 |
| ACAATTACTT | AGTTTGTGGT | TGAGATAGCA | ACACGAATCA | GAACTATTTG | GTGGACATAT | 10680 |
| TTTCAAAGGA | GTAGCTCTCC | ACTTTGGGTA | AAGAAGTGAT | GCNGGTCGTG | GTGGCTCACG | 10740 |
| CCTGTAATCC | CAGCACTTTA | GGGAGGCCAA | GGCGGGTGGA | TCACGAGGTC | AGGAGATCGA | 10800 |
| GACCATCCTG | GCTAACACGG | TGAAACCCCG | TCTCTACTAA | AAATACAAA | AAATTAGCCA | 10860 |
| GGCGTGGTGG | CGGGCGCCTG | TAGTCCCACG | TACTCGGGAG | GCTGAGGCAG | GAGAATGGCA | 10920 |
| TGAACCAGGG | AGGCGGAGCT | TGCCGTGAGC | CGAGATAGCG | CCACTGCAGT | CCCTCCTGGG | 10980 |
| CAAAAGAGCA | AGACTGCGTC | TCAAAAAAAA | AAAAAAAAA | AAAAAAGAA | GTGTGTGGAG | 11040 |
| TAGCAGGACA | CCTGCAACAA | TAATATTTTT | CTAAATCCCT | CTGAAAAATG | CTAATCAAAG | 11100 |
| GGTTTTTTTC | CTAAAAATTG | TCTTAGAAAT | AAAATTTCCC | CTTTGGGAGA | CCGAGGCTGG | 11160 |
| CAGATCACGA | GGTCAGGAGA | TAGAGACCAC | GGTGAAACCC | CGTCTCTACT | AAAAATACTA | 11220 |
| AAAATTAGCC | GGGGNGTGGT | GGTGGGTACA | CCTGTAGTCC | CAGCTACTTG | GAGGCTGAGG | 11280 |
| CTGGAGAATC | ACGTGAAC | | | | | 11298 |

( 2 ) INFORMATION FOR SEQ ID NO:32:

( i ) SEQUENCE CHARACTERISTICS:
        ( A ) LENGTH: 244 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: homo sapien
        ( B ) STRAIN: FcRI beta subunit ( x i ) SEQUENCE DESCRIPTION: SEQ ID NO:32:

```
Met  Asp  Thr  Glu  Ser  Asn  Arg  Arg  Ala  Asn  Leu  Ala  Leu  Pro  Gln  Glu
 1                  5                        10                         15

Pro  Ser  Ser  Val  Pro  Ala  Phe  Glu  Val  Leu  Glu  Ile  Ser  Pro  Gln  Glu
              20                       25                       30

Val  Ser  Ser  Gly  Arg  Leu  Leu  Lys  Ser  Ala  Ser  Ser  Pro  Pro  Leu  His
```

|     |     |     |     | 35  |     |     |     |     | 40  |     |     |     |     | 45  |     |     |     |
|-----|-----|-----|-----|-----|-----|-----|-----|-----|-----|-----|-----|-----|-----|-----|-----|-----|-----|

Thr Trp Leu Thr Val Leu Lys Lys Glu Gln Glu Phe Leu Gly Val Thr
        50                      55                      60

Gln Ile Leu Thr Ala Met Ile Cys Leu Cys Phe Gly Thr Val Val Cys
 65                      70                      75                      80

Ser Val Leu Asp Ile Ser His Ile Glu Gly Asp Ile Phe Ser Ser Phe
                85                      90                      95

Lys Ala Gly Tyr Pro Phe Trp Gly Ala Ile Phe Phe Ser Ile Ser Gly
                100                     105                     110

Met Leu Ser Ile Ile Ser Glu Arg Arg Asn Ala Thr Tyr Leu Val Arg
        115                     120                     125

Gly Ser Leu Gly Ala Asn Thr Ala Ser Ser Ile Ala Gly Gly Thr Gly
        130                     135                     140

Ile Thr Ile Leu Ile Ile Asn Leu Lys Lys Ser Leu Ala Tyr Ile His
145                     150                     155                     160

Ile His Ser Cys Gln Lys Phe Phe Glu Thr Lys Cys Phe Met Ala Ser
                165                     170                     175

Phe Ser Thr Glu Ile Val Val Met Met Leu Phe Leu Thr Ile Leu Gly
                180                     185                     190

Leu Gly Ser Ala Val Ser Leu Thr Ile Cys Gly Ala Gly Glu Glu Leu
        195                     200                     205

Lys Gly Asn Lys Val Pro Glu Asp Arg Val Tyr Glu Leu Asn Ile
        210                     215                     220

Tyr Ser Ala Thr Tyr Ser Glu Leu Glu Asp Pro Gly Glu Met Ser Pro
225                     230                     235                     240

Pro Ile Asp Leu ( 2 ) INFORMATION FOR SEQ ID NO:33:

( i ) SEQUENCE CHARACTERISTICS:
        ( A ) LENGTH: 243 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: rat
        ( B ) STRAIN: FcRI beta subunit ( x i ) SEQUENCE DESCRIPTION: SEQ ID NO:33:

Met Asp Thr Glu Asn Lys Ser Arg Ala Asp Leu Ala Leu Pro Asn Pro
 1                       5                      10                      15

Gln Glu Ser Pro Ser Ala Pro Asp Ile Glu Leu Leu Glu Ala Ser Pro
                20                      25                      30

Pro Ala Lys Ala Leu Pro Glu Lys Pro Ala Ser Pro Pro Gln Gln
        35                      40                      45

Thr Trp Gln Ser Phe Leu Lys Lys Glu Leu Glu Phe Leu Gly Val Thr
        50                      55                      60

Gln Val Leu Val Gly Leu Ile Cys Leu Cys Phe Gly Thr Val Val Cys
 65                      70                      75                      80

Ser Thr Leu Gln Thr Ser Asp Phe Asp Asp Glu Val Leu Leu Leu Tyr
                85                      90                      95

Arg Ala Gly Tyr Pro Phe Trp Gly Ala Val Leu Phe Val Leu Ser Gly
                100                     105                     110

Phe Leu Ser Ile Met Ser Glu Arg Lys Asn Thr Leu Tyr Leu Val Arg
        115                     120                     125

| | | | | | | | | | | | | | | |
|---|---|---|---|---|---|---|---|---|---|---|---|---|---|---|
| Gly | Ser | Leu | Gly | Ala | Asn | Ile | Val | Ser | Ser | Ile | Ala | Ala | Gly | Leu | Gly |
| | 130 | | | | | 135 | | | | 140 | | | | | |
| Ile | Ala | Ile | Leu | Ile | Leu | Asn | Leu | Ser | Asn | Asn | Ser | Ala | Tyr | Met | Asn |
| 145 | | | | | 150 | | | | | 155 | | | | | 160 |
| Tyr | Cys | Lys | Asp | Ile | Thr | Glu | Asp | Asp | Gly | Cys | Phe | Val | Thr | Ser | Phe |
| | | | | 165 | | | | | 170 | | | | | 175 | |
| Ile | Thr | Glu | Leu | Val | Leu | Met | Leu | Leu | Phe | Leu | Thr | Ile | Leu | Ala | Phe |
| | | | 180 | | | | | 185 | | | | | 190 | | |
| Cys | Ser | Ala | Val | Leu | Leu | Ile | Ile | Tyr | Arg | Ile | Gly | Gln | Glu | Phe | Glu |
| | | 195 | | | | | 200 | | | | | 205 | | | |
| Arg | Ser | Lys | Val | Pro | Asp | Asp | Arg | Leu | Tyr | Glu | Glu | Leu | His | Val | Tyr |
| | 210 | | | | | 215 | | | | | 220 | | | | |
| Ser | Pro | Ile | Tyr | Ser | Ala | Leu | Glu | Asp | Thr | Arg | Glu | Ala | Ser | Ala | Pro |
| 225 | | | | | 230 | | | | | 235 | | | | | 240 |
| Val | Val | Ser | | | | | | | | | | | | | |

( 2 ) INFORMATION FOR SEQ ID NO:34:

( i ) SEQUENCE CHARACTERISTICS:
    ( A ) LENGTH: 235 amino acids
    ( B ) TYPE: amino acid
    ( D ) TOPOLOGY: linear ( i i ) MOLECULE TYPE: protein ( v i ) ORIGINAL SOURCE:
    ( A ) ORGANISM: mouse
    ( B ) STRAIN: FcRI beta subunit ( x i ) SEQUENCE DESCRIPTION: SEQ ID NO:34:

| | | | | | | | | | | | | | | | |
|---|---|---|---|---|---|---|---|---|---|---|---|---|---|---|---|
| Met | Asp | Thr | Glu | Asn | Arg | Ser | Arg | Ala | Asp | Leu | Ala | Leu | Pro | Asn | Pro |
| 1 | | | | 5 | | | | | 10 | | | | | 15 | |
| Gln | Glu | Ser | Ser | Ser | Ala | Pro | Asp | Ile | Glu | Leu | Leu | Glu | Ala | Ser | Pro |
| | | | 20 | | | | | 25 | | | | | 30 | | |
| Ala | Lys | Ala | Ala | Pro | Pro | Lys | Gln | Thr | Trp | Arg | Thr | Phe | Leu | Lys | Lys |
| | | | 35 | | | | 40 | | | | | 45 | | | |
| Glu | Leu | Glu | Phe | Leu | Gly | Ala | Thr | Gln | Ile | Leu | Val | Gly | Leu | Ile | Cys |
| | | 50 | | | | | 55 | | | | | 60 | | | |
| Leu | Cys | Phe | Gly | Thr | Ile | Val | Cys | Ser | Val | Leu | Tyr | Val | Ser | Asp | Phe |
| 65 | | | | | 70 | | | | | 75 | | | | | 80 |
| Asp | Glu | Glu | Val | Leu | Leu | Leu | Tyr | Lys | Leu | Gly | Tyr | Pro | Phe | Trp | Gly |
| | | | | 85 | | | | | 90 | | | | | 95 | |
| Ala | Val | Leu | Phe | Val | Leu | Ser | Gly | Phe | Leu | Ser | Ile | Ile | Ser | Glu | Arg |
| | | | 100 | | | | | 105 | | | | | 110 | | |
| Lys | Asn | Thr | Leu | Tyr | Leu | Val | Arg | Gly | Ser | Leu | Gly | Ala | Asn | Ile | Val |
| | | 115 | | | | | 120 | | | | | 125 | | | |
| Ser | Ser | Ile | Ala | Ala | Gly | Thr | Gly | Ile | Ala | Met | Leu | Ile | Leu | Asn | Leu |
| | 130 | | | | | 135 | | | | | 140 | | | | |
| Thr | Asn | Asn | Phe | Ala | Tyr | Met | Asn | Asn | Cys | Lys | Asn | Val | Thr | Glu | Asp |
| 145 | | | | | 150 | | | | | 155 | | | | | 160 |
| Asp | Gly | Cys | Phe | Val | Ala | Ser | Phe | Thr | Thr | Glu | Leu | Val | Leu | Met | Met |
| | | | | 165 | | | | | 170 | | | | | 175 | |
| Leu | Phe | Leu | Thr | Ile | Leu | Ala | Phe | Cys | Ser | Ala | Val | Leu | Phe | Thr | Ile |
| | | | 180 | | | | | 185 | | | | | 190 | | |
| Tyr | Arg | Ile | Gly | Gln | Glu | Leu | Glu | Ser | Lys | Lys | Val | Pro | Asp | Asp | Arg |
| | | 195 | | | | | 200 | | | | | 205 | | | |
| Leu | Tyr | Glu | Glu | Leu | Asn | Val | Tyr | Ser | Pro | Ile | Tyr | Ser | Glu | Leu | Glu |
| | 210 | | | | | 215 | | | | | 220 | | | | |

| Asp | Lys | Gly | Glu | Thr | Ser | Ser | Pro | Val | Asp | Ser |
|-----|-----|-----|-----|-----|-----|-----|-----|-----|-----|-----|
| 225 |     |     |     | 230 |     |     |     |     | 235 |     |